United States Patent [19]

Audia et al.

[11] Patent Number: 5,708,008
[45] Date of Patent: Jan. 13, 1998

[54] 5-SUBSTITUTED-3-(1,2,3,6-TETRAHYDROPYRIDIN-4-YL)-AND 3-(PIPERIDIN-4-YL)-1H-INDOLES: NEW 5-$HT_{1F}$ AGONISTS

[75] Inventors: James Edmund Audia; Bruce Anthony Dressman; James Joseph Droste, all of Indianapolis; James Erwin Fritz, Greenwood; Stephen Warren Kaldor, Indianapolis; Daniel James Koch, Indianapolis; Joseph Herman Krushinski, Jr., Indianapolis; Jeffrey Scott Nissen, Indianapolis; Vincent Patrick Rocco, Indianapolis; John Mehnert Schaus, Zionsville; Dennis Charles Thompson, Indianapolis, all of Ind.

[73] Assignee: Eli Lilly and Company, Indianapolis, Ind.

[21] Appl. No.: 619,783

[22] Filed: Mar. 20, 1996

Related U.S. Application Data

[63] Continuation-in-part of Ser. No. 407,553, Mar. 20, 1995, abandoned.

[51] Int. Cl.$^6$ .................... A61K 31/445; C07D 401/04
[52] U.S. Cl. ............. 514/323; 514/228.2; 514/235.2; 514/255; 514/316; 514/318; 514/339; 544/62; 544/129; 544/124; 544/360; 544/373; 546/187; 546/193; 546/201; 546/277.4
[58] Field of Search .................... 546/201, 145, 546/187, 193, 169, 277.4; 544/62, 129, 238, 333, 361, 360, 373, 124; 514/228.2, 235.2, 255, 316, 318, 323, 339

[56] References Cited

U.S. PATENT DOCUMENTS

| | | | |
|---|---|---|---|
| 3,850,938 | 11/1974 | Derible et al. | 546/201 |
| 4,278,677 | 7/1981 | Nedelec et al. | 514/339 |
| 4,359,468 | 11/1982 | Freter et al. | 514/322 |
| 4,530,932 | 7/1985 | Clemence et al. | 514/318 |
| 4,710,500 | 12/1987 | Perregaard | 514/254 |
| 4,742,057 | 5/1988 | Ueda et al. | 514/235.2 |
| 4,997,841 | 3/1991 | Oxford et al. | 514/323 |
| 5,001,135 | 3/1991 | Oxford et al. | 514/323 |
| 5,017,703 | 5/1991 | Matsuo et al. | 546/201 |
| 5,036,078 | 7/1991 | Coates | 514/323 |
| 5,066,660 | 11/1991 | Oxford et al. | 514/323 |
| 5,118,691 | 6/1992 | Jaen et al. | 514/314 |
| 5,187,280 | 2/1993 | Jaen et al. | 546/256 |
| 5,216,001 | 6/1993 | Perregaard et al. | 514/323 |
| 5,298,520 | 3/1994 | Baker et al. | 514/383 |
| 5,317,025 | 5/1994 | Bru-Magniez et al. | 514/323 |
| 5,322,851 | 6/1994 | Perregaard et al. | 514/323 |
| 5,545,644 | 8/1996 | Moor et al. | 514/323 |

FOREIGN PATENT DOCUMENTS

| | | |
|---|---|---|
| 378255 | 7/1990 | European Pat. Off. . |
| 438230 | 7/1991 | European Pat. Off. . |
| 91/18897 | 12/1991 | WIPO . |
| 92/06973 | 4/1992 | WIPO . |
| 93/13856 | 8/1992 | WIPO . |
| WO 93/11106 | 6/1993 | WIPO . |
| 94/03446 | 2/1994 | WIPO . |
| 94/10171 | 5/1994 | WIPO . |
| WO 94/14770 | 7/1994 | WIPO . |
| WO 94/24127 | 10/1994 | WIPO . |

OTHER PUBLICATIONS

Moskowitz, M.A. et al, J. Neurology, 1991, 238 Suppl. 1, pp. S18–22, ref: 29. Online Abstract relied upon.
Hansch, Corwin, and Caldwell, Jonathan; *Journal Computer-Aided molecular Design*, 5, 441–453 (1991).
Taylor, et al., *Molecular Pharmacology*, 34, 42–52 (1988).
Agarwal, et al., *J. Med. Chem.*, 36, 4006–4014 (1993).
Macor, John, Presentation: "Serotonin in Neuroscience", Philadelphia, Sep. 27–29, (1994).
M.A. Moskowitz, et al., *Journal of Neurology*, (1991), 258:S18–S22.
Taylor, et al., *Molecular Pharmacology*, vol. 34, No. 1, (Jul. 1988), pp. 42–54.

*Primary Examiner*—C. Warren Ivy
*Assistant Examiner*—Garth Danlen
*Attorney, Agent, or Firm*—Robert D. Titus; David E. Boone

[57] ABSTRACT

This invention provides novel 5-$HT_{1F}$ agonists of Formula I

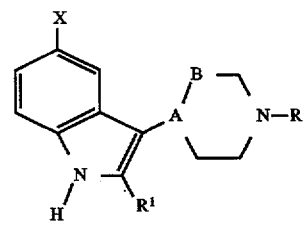

where A—B, R, $R^1$ and X are as defined in the specification, which are useful for the treatment of migraine and associated disorders.

28 Claims, No Drawings

5-SUBSTITUTED-3-(1,2,3,6-TETRAHYDROPYRIDIN-4-YL)-AND 3-(PIPERIDIN-4-YL)-1H-INDOLES: NEW 5-HT$_{1F}$ AGONISTS

CROSS-REFERENCE

This application is a continuation-in-part of application U.S. Ser. No. 08/407,553, filed Mar. 20, 1995 now abandoned.

BACKGROUND OF THE INVENTION

Theories regarding the pathophysiology of migraine have been dominated since 1938 by the work of Graham and Wolff (*Arch. Neurol. Psychiatry*, 39, 737–63 (1938)). They proposed that the cause of migraine headache was vasodilatation of extracranial vessels. This view was supported by knowledge that ergot alkaloids and sumatriptan, a hydrophilic 5-HT$_1$ agonist which does not cross the blood-brain barrier, contract cephalic vascular smooth muscle and are effective in the treatment of migraine. (Humphrey, et al., *Ann. NY Acad. Sci.*, 600, 587–600 (1990)). Recent work by Moskowitz has shown, however, that the occurrence of migraine headaches is independent of changes in vessel diameter (*Cephalalgia*, 12, 5–7, (1992)).

Moskowitz has proposed that currently unknown triggers for pain stimulate trigeminal ganglia which innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers (*Neurology*, 43(suppl. 3), S16–S20 (1993)).

Serotonin (5-HT) exhibits diverse physiological activity mediated by at least seven receptor classes, the most heterogeneous of which appears to be 5-HT$_1$. A human gene which expresses one of these 5-HT$_1$ receptor subtypes, named 5-HT$_{1F}$, was isolated by Kao and coworkers (*Proc. Natl. Acad. Sci. USA*, 90, 408–412 (1993)). This 5-HT$_{1F}$ receptor exhibits a pharmacological profile distinct from any serotonergic receptor yet described. The high affinity of sumatriptan at this subtype, $K_i$=23 nM, suggests a role of the 5-HT$_{1F}$ receptor in migraine.

This invention provides novel 5-HT$_{1F}$ agonists which inhibit peptide extravasation due to stimulation of the trigeminal ganglia, and are therefore useful for the treatment of migraine and associated disorders.

SUMMARY OF THE INVENTION

The present invention provides novel 5-substituted-3-1,2,3,6-tetrahydropyridin-4-yl)-1H-indoles and 5-substituted-3-(piperidin-4-yl)-1H-indoles of Formula I:

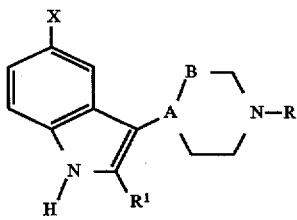

I in which

A—B is —CH—CH$_2$— or —C=CH—;

R is H or C$_1$–C$_6$ alkyl;

R$^1$ is H or C$_1$–C$_4$ alkyl;

X is —S—R$^2$, —C(O)R$^3$, —C(O)NR$^4$R$^{15}$, —NR$^5$R$^6$, —NR$^7$SO$_2$R$^8$, —NHC(Q)NR$^{10}$R$^{11}$, —NHC(O)OR$^{12}$ or —NR$^{13}$C(O)R$^{14}$; where Q is O, or S;

R$^2$ is phenyl, substituted phenyl, phenyl(C$_1$–C$_4$ alkylene), phenyl(C$_1$–C$_4$ alkylene) substituted in the phenyl ring, or pyridinyl;

R$^3$ is C$_1$–C$_6$ alkyl, phenyl(C$_1$–C$_4$ alkylene), phenyl (C$_1$–C$_4$ alkylene) substituted in the phenyl ring, naphthyl, N-methyl-N-methoxyamino, heteroaryl, substituted heteroaryl, heteroaryl(C$_1$–C$_4$ alkyl), or substituted heteroaryl(C$_1$–C$_4$ alkyl);

R$^4$ is heteroaryl, substituted heteroaryl, heteroaryl(C$_1$–C$_4$ alkyl), or substituted heteroaryl(C$_1$–C$_4$ alkyl);

R$^4$ and R$^{15}$ taken together with the nitrogen atom form a pyrrolidine, piperidine, substituted piperidine, piperazine, 4-substituted piperazine, morpholine or thiomorpholine ring;

R$^5$ and R$^6$ are both trifluoromethanesulfonyl;

R$^7$ is H or C$_1$–C$_4$ alkyl;

R$^8$ is C$_1$–C$_4$ alkyl, phenyl, substituted phenyl, or di(C$_1$–C$_4$ alkyl)amino;

R$^{10}$ and R$^{11}$ are independently selected from the group consisting of C$_1$–C$_6$ alkyl, C$_3$–C$_6$ alkenyl, C$_3$–C$_8$ cycloalkyl, phenyl, substituted phenyl, phenyl(C$_1$–C$_4$ alkylene), phenyl(C$_1$–C$_4$ alkylene) substituted in the phenyl ring, ((C$_1$–C$_4$ alkyl or C$_1$–C$_4$ alkoxycarbonyl substituted)C$_1$–C$_4$ alkyl)phenyl, C$_1$–C$_4$ alkyl α-substituted with C$_1$–C$_4$ alkoxycarbonyl; or R$^{10}$ and R$^{11}$ taken together with the nitrogen atom form a pyrrolidine, piperidine, piperazine, 4-substituted piperazine, morpholine or thiomorpholine ring;

R$^{12}$ is C$_1$–C$_6$ alkyl, C$_3$–C$_6$ alkenyl, phenyl, substituted phenyl, C$_3$–C$_8$ cycloalkyl, C$_1$–C$_4$ alkyl ω-substituted with C$_1$–C$_4$ alkoxy;

R$^{13}$ is H or C$_1$–C$_4$ alkyl;

R$^{14}$ is C$_1$–C$_{10}$ alkyl substituted with up to three substituents selected from the group consisting of hydroxy, C$_1$–C$_4$ alkoxy, halo, aryloxy, C$_1$–C$_4$ alkoxycarbonyl and heteroaryloxy, C$_2$–C$_{10}$ alkenyl, C$_2$–C$_{10}$ alkynyl, C$_3$–C$_8$ cycloalkyl, phenyl, substituted phenyl, naphthyl, phenyl(C$_1$–C$_4$ alkylene), phenyl(C$_1$–C$_4$ alkylene) substituted on the phenyl ring, 2-phenylethylen-1-yl, diphenylmethyl, benzofused C$_4$–C$_8$ cycloalkyl, C$_1$–C$_4$ alkylene ω-substituted with C$_3$–C$_6$ cycloalkyl, or a heterocycle;

R$^{15}$ is H or C$_1$–C$_6$ alkyl;

subject to the proviso that when R$^7$ is H, R$^8$ is not C$_1$–C$_4$ alkyl; and pharmaceutically acceptable acid addition salts and solvates thereof. This invention also provides a pharmaceutical formulation which comprises, in association with a pharmaceutically acceptable carrier, diluent or excipient, a compound of Formula I.

A further embodiment of this invention is a method for increasing activation of the 5-HT$_{1F}$ receptor for treating a variety of disorders which have been linked to decreased neurotransmission of serotonin in mammals. Included among these disorders are depression, migraine pain, bulimia, premenstrual syndrome or late luteal phase syndrome, alcoholism, tobacco abuse, panic disorder, anxiety, general pain, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, mutism, trichotillomania, trigeminal neuralgia, dental pain or temperomandibular joint dysfunction pain. The compounds of this invention are also useful as a prophylactic treatment for migraine. Any of these methods employ a compound of Formula I.

The use of a compound of Formula I for the activation of the 5-HT$_{1F}$ receptor, for the inhibition of peptide extravasation in general or due to stimulation of the trigeminal ganglia specifically, and for the treatment of any of the disorders described supra, are all embodiments of the present invention.

DETAILED DESCRIPTION OF THE INVENTION

The general chemical terms used in the formulae above have their usual meanings. For example, the terms "alkyl, alkoxy and alkylthio" include such groups as methyl, ethyl, n-propyl, isopropyl, n-butyl, isobutyl, sec-butyl, tert-butyl, pentyl, 2-pentyl-, 3-pentyl-, neopentyl, hexyl, heptyl, octyl and the like. The term "alkenyl" includes vinyl, allyl, 1-buten-4-yl, 2-buten-4-yl, 1-penten-5-yl, 2-penten-5-yl, 3-penten-5-yl, 1-hexen-6-yl, 2-hexen-6-yl, 3-hexen-6-yl, 4-hexen-6-yl and the like. The term "alkynyl" includes acetylenyl, propynyl, 2-butyn-4-yl, 1-butyn-4-yl, 1-pentyn-5-yl, 2-pentyn-5-yl and the like. The term "acyl" includes, for example, formyl, acetyl, propanoyl, butanoyl, and 2-methylpropanoyl. The term "cycloalkyl" includes such groups as cyclopropyl, cyclobutyl, cyclopentyl, cyclohexyl, cycloheptyl and cyclooctyl. The term "phenyl($C_1$–$C_4$ alkylene)" includes such groups as benzyl, phenethyl, phenpropyl and phenbutyl. The term "($C_1$–$C_4$ alkyl)sulfonyl" includes methanesulfonyl, ethanesulfonyl propanesulfonyl, isopropanesulfonyl, butanesulfonyl and the like. The term "halo" includes fluoro, chloro, bromo and iodo.

The term "substituted phenyl" or "phenyl($C_1$–$C_4$ alkylene) substituted in the phenyl ring" is taken to mean the phenyl moiety may be substituted with one substituent selected from the group consisting of halo, $C_1$–$C_4$ alkyl, $C_1$–$C_8$ alkoxy, $C_1$–$C_4$ alkylthio, nitro, cyano, di($C_1$–$C_4$ alkyl)amino, trifluoromethyl, trifluoromethoxy, phenyl, $C_1$–$C_4$ acyl, benzoyl or ($C_1$–$C_4$ alkyl)sulfonyl, or two to three substituents independently selected from the group consisting of halo, nitro, $C_1$–$C_4$ alkyl, or $C_1$–$C_4$ alkoxy.

The term "heterocycle" is taken to mean stable aromatic and non-aromatic 5- and 6-membered rings containing from 1 to 3 heteroatoms selected from the group consisting of nitrogen, oxygen and sulfur, said rings being optionally benzofused. All of these rings may be substituted with up to three substituents independently selected from the group consisting of halo, $C_1$–$C_4$ alkoxy, $C_1$–$C_4$ alkyl, cyano, nitro, hydroxy, —S(O)$_n$-($C_1$–$C_4$ alkyl) and —S(O)$_n$-phenyl where n is 0, 1 or 2. Non-aromatic rings include, for example, pyrrolidinyl, piperidinyl, piperazinyl, tetrahydrofuryl, oxazolidinyl, dioxanyl, pyranyl, and the like. Benzofused non-aromatic rings include indolinyl, 1,2,3,4-tetrahydroquinolinyl, 1,2,3,4-tetrahydroisoquinolinyl and the like. Aromatic rings include furyl, thienyl, pyridinyl, pyrrolyl, N-methylpyrrolyl, oxazolyl, isoxazolyl, pyrazolyl, imidazolyl, triazolyl, oxadiazolyl, thiadiazolyl, thiazolyl, pyrimidinyl, pyyazinyl, pyridazinyl, and the like. Benzofused aromatic rings include isoquinolinyl, benzoxazolyl, benzthiazolyl, quinolinyl, benzofuranyl, thionaphthyl, indolyl and the like.

The term "heteroaryl" is taken to mean an aromatic or benzolused aromatic heterocycle as defined in the previous paragraph. The term "substituted heteroaryl" is taken to mean an aromatic or benzofused aromatic heterocycle as defined in the previous paragraph substituted with up to three substituents independently selected from the group consisting of halo, $C_1$–$C_4$ alkoxy, $C_1$–$C_4$ alkyl, cyano, nitro, hydroxy, —S(O)$_n$-($C_1$–$C_4$ alkyl) and —S(O)$_n$-phenyl where n is 0, 1 or 2. The term "heteroaryl($C_1$–$C_4$ alkyl) is taken to mean a branched or linear alkyl chain of 1 to 4 carbon atoms substituted at some point with an aromatic or benzofused aromatic heterocycle moiety. The term "substituted heteroaryl($C_1$–$C_4$ alkyl)" is taken to mean a branched or linear alkyl chain of 1 to 4 carbon atoms substituted at some point with an aromatic or benzofused aromatic heterocycle moiety which is substituted with up to three substituents independently selected from the group consisting of halo, $C_1$–$C_4$ alkoxy, $C_1$–$C_4$ alkyl, cyano, nitro, hydroxy, —S(O)$_n$-($C_1$–$C_4$ alkyl) and —S(O)$_n$-phenyl where n is 0, 1 or 2.

The term "heteroaryloxy" is taken to mean a heteroaryl or substituted heteroaryl group, as defined in the previous paragraph, bonded to an oxygen atom.

The term "aryloxy" is taken to mean a phenyl or substituted phenyl group bonded to an oxygen atom.

The term "4-substituted piperazine" is taken to mean a piperazine ring substituted at the 4-position with a substituent selected from the group consisting of $C_1$–$C_6$ alkyl, $C_1$–$C_4$ alkoxy substituted $C_1$–$C_6$ alkyl, phenyl, substituted phenyl, phenyl($C_1$–$C_4$ alkylene), phenyl($C_1$–$C_4$ alkylene) substituted in the phenyl ring, heteroaryl, and heteroaryl ($C_1$–$C_4$ alkylene).

The term "substituted piperidine" is taken to mean a piperidine ring optionally substituted with a substituent selected from the group consisting of hydroxy, hydroxymethyl, and N,N-di($C_1$–$C_4$ alkyl)carboxamido.

The term "benzolused $C_4$–$C_8$ cycloalkyl" is taken to mean a $C_4$–$C_8$ cycloalkyl group fused to a phenyl ring. Examples of these groups include benzocyclobutyl, indanyl, 1,2,3,4-tetrahydronaphthyl, and the like.

While all of the compounds of this invention are useful as 5-HT$_{1F}$ agonists, certain classes are preferred. The following paragraphs describe such preferred classes.

aa) A—B is —C=CH—;
ab) A—B is —CH—CH$_2$—;
ac) R is H;
ad) R is $C_1$–$C_4$ alkyl;
ae) R is methyl;
af) R$^1$ is methyl;
ag) R$^1$ is H;
ah) X is —S—R$_2$;
ai) X is —C(O)R$^3$;
aj) X is —C(O)NR$^4$R$^{15}$;
ak) X is —NR$^5$R$^6$;
al) X is —NR$^7$SO$_2$R$^8$;
am) X is —NHC(Q)NR$^{10}$R$^{11}$;
an) X is —NHC(O)OR$^{12}$;
ao) X is —NR$^{13}$C(O)R$^{14}$;
ap) Q is O;
aq) R$^2$ is phenyl monosubstituted with halo;
ar) R$^2$ is 4-chlorophenyl;
as) R$^2$ is phenyl($C_1$–$C_4$ alkylene);

at) $R^2$ is benzyl;
au) $R^2$ is pyridinyl;
av) $R^2$ is 2-pyridinyl;
aw) $R^3$ is $C_1$–$C_4$ alkyl;
ax) $R^3$ is methyl;
ay) $R^3$ is butyl;
az) $R^3$ is phenyl($C_1$–$C_4$ alkylene);
ba) $R^3$ is benzyl;
bb) $R^3$ is phenyl;
bc) $R^3$ is heteroaryl;
bd) $R^4$ is heteroaryl or substituted heteroaryl;
be) $R^4$ is heteroaryl($C_1$–$C_4$ alkyl) or substituted heteroaryl ($C_1$–$C_4$ alkyl);
bf) $R^7$ is $C_1$–$C_4$ alkyl;
bg) $R^7$ is methyl;
bh) $R^7$ is H;
bi) $R^8$ is $C_1$–$C_4$ alkyl;
bj) $R^8$ is methyl;
bk) $R^8$ is ethyl;
bl) $R^8$ is phenyl;
bm) $R^8$ is di($C_1$–$C_4$ alkyl)amino;
bn) $R^8$ is dimethylamino;
bo) $R^{10}$ is H;
bp) $R^{11}$ is $C_1$–$C_4$ alkyl;
bq) $R^{11}$ is methyl;
br) $R^{11}$ is ethyl;
bs) $R^{11}$ is propyl;
bt) $R^{11}$ is isopropyl;
bu) $R^{11}$ is phenyl;
bv) $R^{11}$ is $C_3$–$C_8$ alkenyl;
bw) $R^{11}$ is allyl;
bx) $R^{11}$ is phenyl monosubstituted with halo;
by) $R^{11}$ is 4-fluorophenyl;
bz) $R^{11}$ is 4-chlorophenyl;
ca) $R^{11}$ is phenyl($C_1$–$C_4$ alkylene)
cb) $R^{11}$ is benzyl;
cc) $R^{11}$ is phenethyl;
cd) $R^{10}$ and $R^{11}$ taken together with nitrogen form a morpholine ring;
ce) $R^{10}$ and $R^{11}$ taken together with nitrogen form a thiomorpholine ring;
cf) $R^{10}$ and $R^{11}$ taken together with nitrogen form a pyrrolidine ring;
cg) $R^{10}$ and $R^{11}$ taken together with nitrogen form a piperidine ring;
ch) $R^{10}$ and $R^{11}$ taken together with nitrogen form a pyrrolidine ring;
ci) $R^{10}$ and $R^{11}$ taken together with nitrogen form a piperazine ring;
cj) $R^{10}$ and $R^{11}$ taken together with nitrogen form a 4-substituted piperazine ring;
ck) $R^{12}$ is $C_1$–$C_4$ alkyl;
cl) $R^{12}$ is methyl;
cm) $R^{12}$ is ethyl;
cn) $R^{12}$ is propyl;
co) $R^{12}$ is $C_3$–$C_6$ alkenyl;
cp) $R^{12}$ is allyl;
cq) $R^{12}$ is $C_3$–$C_8$ cycloalkyl;
cr) $R^{12}$ is cyclopentyl;
cs) $R^{12}$ is phenyl monosubstituted with $C_1$–$C_4$ alkoxy;
ct) $R^{12}$ is 4-methoxyphenyl;
cu) $R^{13}$ is H;
cv) $R^{13}$ is $C_1$–$C_4$ alkyl;
cw) $R^{14}$ is $C_3$–$C_6$ alkenyl;
cx) $R^{14}$ is allyl;
cy) $R^{14}$ is $C_3$–$C_6$ cycloalkyl;
cz) $R^{14}$ is cyclopropyl;
da) $R^{14}$ is cyclobutyl;
db) $R^{14}$ is phenyl($C_1$–$C_4$ alkylene);
dc) $R^{14}$ is $C_1$–$C_4$ alkyl ω-substituted with phenoxy;
dd) $R^{14}$ is $C_1$–$C_4$ alkyl ω-substituted with $C_1$–$C_4$ alkoxy;
de) $R^{14}$ is methoxymethyl;
df) $R^{14}$ is ethoxymethyl;
dg) $R^{14}$ is phenyl;
dh) $R^{14}$ is 2-phenylethylen-1yl;
di) $R^{14}$ is phenyl monosubstituted with halo;
dj) $R^{14}$ is phenyl monosubstituted with chloro;
dk) $R^{14}$ is phenyl monosubstituted with fluoro;
dl) $R^{14}$ is 4-fluorophenyl;
dm) $R^{14}$ is 2-chlorophenyl;
dn) $R^{14}$ is phenyl monosubstituted with $C_1$–$C_4$ alkoxy;
do) $R^{14}$ is phenyl monosubstituted with methoxy;
dp) $R^{14}$ is 4-methoxyphenyl;
dq) $R^{14}$ is phenyl monosubstituted with $C_1$–$C_4$ alkyl;
dr) $R^{14}$ is phenyl monosubstituted with methyl;
ds) $R^{14}$ is phenyl monosubstituted with trifluoromethyl, $C_1$–$C_4$ alkylthio, cyano, nitro, phenyl, $C_1$–$C_4$ acyl or benzoyl;
dt) $R^{14}$ is 4-cyanophenyl;
du) $R^{14}$ is 4-nitrophenyl;
dv) $R^{14}$ is 4-phenylphenyl;
dw) $R^{14}$ is phenyl disubstituted with substitutents selected from halo, $C_1$–$C_4$ alkyl, $C_1$–$C_4$ alkoxy and nitro;
dx) $R^{14}$ is phenyl disubstituted with halo;
dy) $R^{14}$ is 2,4-dichlorophenyl;
dz) $R^{14}$ is a heterocycle;
ea) $R^{14}$ is furyl optionally substituted with $C_1$–$C_4$ alkyl, $C_1$–$C_4$ alkoxy, or halo;
eb) $R^{14}$ is 2-furyl;
ec) $R^{14}$ is 3-furyl;
ed) $R^{14}$ is thienyl optionally substituted with halo, $C_1$–$C_4$ alkyl or $C_1$–$C_4$ alkoxy;
ef) $R^{14}$ is 2-thienyl;
eg) $R^{14}$ is 3-thienyl;
eh) $R^{14}$ is 3-methyl-2-thienyl;
ei) $R^{14}$ is 5-methyl-2-thienyl;
ej) $R^{14}$ is pyridinyl optionally substituted with halo, $C_1$–$C_4$ alkyl or $C_1$–$C_4$ alkoxy;
ek) $R^{14}$ is 3-pyridinyl;
el) $R^{14}$ is 4-pyridinyl;
em) $R^{14}$ is 6-halo-3-pyridinyl;
en) $R^{14}$ is pyrazinyl;
eo) $R^{14}$ is isoxazolyl;
ep) $R^{14}$ is 2-benzofuranyl;
eq) $R^{15}$ is hydrogen;

er) $R^{15}$ is $C_1$–$C_6$ alkyl;
es) $R^{15}$ is methyl;
et) $R^{15}$ is butyl;
eu) $R^{15}$ is isopropyl;
ev) $R^4$ and $R^{15}$ taken together with the nitrogen atom form a pyrrolidine ring;
ew) $R^4$ and $R^{15}$ taken together with the nitrogen atom form a piperidine ring;
ex) $R^4$ and $R^{15}$ taken together with the nitrogen atom form a substituted piperidine ring;
ey) $R^4$ and $R^{15}$ taken together with the nitrogen atom form a piperazine ring;
ez) $R^4$ and $R^{15}$ taken together with the nitrogen atom form a 4-substituted piperazine ring;
fa) $R^4$ and $R^{15}$ taken together with the nitrogen atom form a morpholine ring;
fb) $R^4$ and $R^{15}$ taken together with the nitrogen atom form a thiomorpholine ring;
fc) The compound is a free base;
fd) The compound is a salt;
re) The compound is the hydrochloride salt;
ff) The compound is the fumarate salt;
fg) The compound is the oxalate salt.

It will be understood that the above classes may be combined to form additional preferred classes.

The compounds of this invention are useful in a method for increasing activation of the 5-HT$_{1F}$ receptor for treating a variety of disorders which have been linked to decreased neurotransmission of serotonin in mammals. It is preferred that the mammal to be treated by the administration of compounds of this invention is human.

Since the compounds of this invention are amines, they are basic in nature and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluene-sulfonic acid, methanesulfonic acid, oxalic acid, p-bromo-phenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propion-ate, decanoate, caprylate, acrylate, formate, isobutyrate, caproate, heptanoate, propiolate, oxalate, malonate, suc-cinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, b-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid, oxalic acid or fumaric acid.

The following group is illustrative of compounds contemplated within the scope of this invention:

5-(4-fluorophenyl thio-3-(1,2,3,6-tetrahydropyridin-4-yl)-1H-indole
5-(3-chlorophenyl)thio-3-(1-(pent-2-yl)-1,2,3,6-tetrahydropyridin-4-yl)-2-methyl-1H-indole
5-(2-bromophenyl)thio-3-(1-pentyl-1,2,3,6-tetrahydropyridin-4-yl)-1H-indole
5-(2-iodophenyl)thio-3-(1-isobutyl-1,2,3,6-tetrahydropyridin-4-yl)-1H-indole
5-(3-methoxyphenyl)thio-3-(1-(sec-butyl)-1,2,3,6-tetrahydropyridin-4-yl)-1H-indole
5-(4-iodophenyl)thio-3-(1-(pent-2-yl)-1,2,3,6-tetrahydropyridin-4-yl)-1H-indole
5-(2-ethoxyphenyl)thio-3-(1-(tert-butyl)-1,2,3,6-tetrahydropyridin-4-yl)-1H-indole
5-(4-ethoxyphenyl)thio-3-(1-isopropyl-1,2,3,6-tetrahydropyridin-4-yl)-1H-indole
5-(3-propoxyphenyl)thio-3-(1-butyl-1,2,3,6-tetrahydropyridin-4-yl)-1H-indole hydrochloride
5-(2-isopropoxyphenyl)thio-3-(1-ethyl-1,2,3,6-tetrahydropyridin-4-yl)-1H-indole
5-(4-isopropoxyphenyl)thio-3-(1-(isobutyl)-1,2,3,6-tetrahydropyridin-4-yl)-1H-indole hydrobromide
5-(3-butoxyphenyl)thio-3-(1-butyl-1,2,3,6-tetrahydropyridin-4-yl)-1H-indole hydroiodide
5-(2-isobutoxyphenyl)thio-3-(1-isobutyl-1,2,3,6-tetrahydropyridin-4-yl)-1H-indole
5-(4-isobutoxyphenyl)thio-3-(1-(tert-butyl)-1,2,3,6-tetrahydropyridin-4-yl)-1H-indole acetate
5-(3-sec-butoxyphenyl)thio-3-(1-butyl-1,2,3,6-tetrahydropyridin-4-yl)-1H-indole
5-(2-tert-butoxyphenyl)thio-3-(1-ethyl-1,2,3,6-tetrahydropyridin-4-yl)-1H-indole propionate
5-(4-tert-butoxyphenyl)thio-3-(1-isobutyl-1,2,3,6-tetrahydropyridin-4-yl)-1H-indole
5-(2-pyridinyl)thio-3-(1-(tert-butyl)-1,2,3,6-tetrahydropyridin-4-yl)-1H-indole decanoate
5-(4-pyridinyl)thio-3-(1-isobutyl-1,2,3,6-tetrahydropyridin-4-yl)-1H-indole
5-(2-phenethyl)thio-3-(1-isopropyl-1,2,3,6-tetrahydropyridin-4-yl)-1H-indole caprylate
5-(4-phenbutyl)thio-3-(1-ethyl-1,2,3,6-tetrahydropyridin-4-yl)-1H-indole
5-(2-chlorophenyl)thio-3-(1-neopentyl)piperidin-4-yl)-1H-indole acrylate
5-(4-bromophenyl)thio-3-(1-(pent-3-yl)piperidin-4-yl)-1H-indole
5-(2-bromophenyl)thio-3-(1-(sec-butyl)piperidin-4-yl)-1H-indole formate
5-(3-iodophenyl)thio-3-(1-(tert-butyl)piperidin-4-yl)-1H-indole
5-(2-methoxyphenyl)thio-3-(1-butylpiperidin-4-yl)-1H-indole isobutyrate
5-(4-methoxyphenyl)thio-3-(1-pentylpiperidin-4-yl)-1H-indole
5-(3-ethoxyphenyl)thio-3-(1-isobutylpiperidin-4-yl)-2-methyl-1H-indole caproate
5-(2-propoxyphenyl)thio-3-(1-propylpiperidin-4-yl)-1H-indole
5-(4-propoxyphenyl)thio-3-(1-(sec-butyl)piperidin-4-yl)-1H-indole heptanoate
5-(3-isopropoxyphenyl)thio-3-(1-isopropylpiperidin-4-yl)-1H-indole
5-(2-butoxyphenyl)thio-3-(1-propylpiperidin-4-yl)-1H-indole propiolate
5-(4-butoxyphenyl)thio-3-(piperidin-4-yl)-1H-indole
5-(2-sec-butoxyphenyl)thio-3-(1-propylpiperidin-4-yl)-1H-indole oxalate 5-(4-sec-butoxyphenyl)thio-3-(1-(sec-butyl)piperidin-4-yl)-1H-indole
5-(2-tert-butoxyphenyl)thio-3-(1-isopropylpiperidin-4-yl)-1H-indole malonate
5-(3-pyridinyl)thio-3-(1-(sec-butyl)piperidin-4-yl)-1H-indole
5-benzylthio-3-(1-butylpiperidin-4-yl)-1H-indole succinate
5-(3-phenpropyl)thio-3-(1-propylpiperidin-4-yl)-1H-indole
5-propanoyl-3-(1-hexyl-1,2,3,6-tetrahydropyridin-4-yl)-1H-indole suberate
5-(2-methylpropanoyl)-3-(1-pentyl-1,2,3,6-tetrahydropyridin-4-yl)-1H-indole
5-butanoyl-3-(1-isobutyl-1,2,3,6-tetrahydropyridin-4-yl)-1H-indole sebacate
5-(sec-butanoyl)-3-(1-propyl-1,2,3,6-tetrahydropyridin-4-yl)-1H-indole
5-(2-methylbutanoyl)-3-(1-isopropyl-1,2,3,6-tetrahydropyridin-4-yl)-2-methyl-1H-indole fumarate
5-(3,3-dimethylbutanoyl)-3-(1-(tert-butyl)-1,2,3,6-tetrahydropyridin-4-yl)-1H-indole
5-heptanoyl-3-(1-(2-pentyl)-1,2,3,6-tetrahydropyridin-4-yl)-1H-indole butyne-1,4-dioate
5-(3-chlorobenzoyl)-3-(1-hexyl-1,2,3,6-tetrahydropyridin-4-yl)-1H-indole
5-(3-fluorobenzoyl)-3-(1-pentyl-1,2,3,6-tetrahydropyridin-4-yl)-1H-indole
5-(3-bromobenzoyl)-3-(1-butyl-1,2,3,6-tetrahydropyridin-4-yl)-1H-indole hydrobromide
5-(2-bromobenzoyl)-3-(1-ethyl-1,2,3,6-tetrahydropyridin-4-yl)-1H-indole
5-(3-iodobenzoyl)-3-(1-isopropyl-1,2,3,6-tetrahydropyridin-4-yl)-1H-indole
5-(3-methoxybenzoyl)-3-(1-(tert-butyl)-1,2,3,6-tetrahydropyridin-4-yl)-1H-indole
5-(2-ethoxybenzoyl)-3-(1-isobutyl-1,2,3,6-tetrahydropyridin-4-yl)-1H-indole
5-(4-ethoxybenzoyl)-3-(1-neopentyl-1,2,3,6-tetrahydropyridin-4-yl)-1H-indole
5-(2-propoxybenzoyl)-3-(1-hexyl-1,2,3,6-tetrahydropyridin-4-yl)-1H-indole hydrochloride
5-(3-propoxybenzoyl)-3-(1,2,3,6-tetrahydropyridin-4-yl)-1H-indole
5-(3-butoxybenzoyl)-3-(1-pentyl-1,2,3,6-tetrahydropyridin-4-yl)-1H-indole
5-(2-methylbenzoyl)-3-(1-propyl-1,2,3,6-tetrahydropyridin-4-yl)-1H-indole
5-(3-ethylbenzoyl)-3-(1-isopropyl-1,2,3,6-tetrahydropyridin-4-yl)-1H-indole
5-(4-propylbenzoyl)-3-(1-(tert-butyl)-1,2,3,6-tetrahydropyridin-4-yl)-1H-indole
5-(2-propylbenzoyl)-3-(1-neopentyl-1,2,3,6-tetrahydropyridin-4-yl)-1H-indole
5-(3-butylbenzoyl)-3-(1-(3-pentyl)-1,2,3,6-tetrahydropyridin-4-yl)-1H-indole
5-(3-trifluoromethylbenzoyl)-3-(1-isobutyl-1,2,3,6-tetrahydropyridin-4-yl)-1H-indole
5-(3-trifluoromethoxybenzoyl)-3-(1-ethyl-1,2,3,6-tetrahydropyridin-4-yl)-1H-indole
5-(3-dimethylaminobenzoyl)-3-(1-1sopropyl-1,2,3,6-tetrahydropyridin-4-yl)-1H-indole
5-(3-phenylpropanoyl)-3-(1-isobutyl-1,2,3,6-tetrahydropyridin-4-yl)-1H-indole
5-(5-phenylpentanoyl)-3-(1-(3-pentyl)-1,2,3,6-tetrahydropyridin-4-yl)-1H-indole
5-(3-pyridinecarbonyl)-3-(1-propyl-1,2,3,6-tetrahydropyridin-4-yl)-1H-indole
5-(3-phenylpropanoyl)-3-(1-isobutyl-1,2,3,6-tetrahydropyridin-4-yl)-1H-indole
5-butanoyl-3-(1-(3-pentyl)piperidin-4-yl)-1H-indole
5-(3-methyl)butanoyl-3-(1-butylpiperidin-4-yl)-2-methyl-1H-indole
5-(2,2-dimethyl)propanoyl-3-(1-(2-pentyl)piperidin-4-yl)-1H-indole fumarate
5-hexanoyl-3-(1-ethylpiperidin-4-yl)-1H-indole
5-(2-ethyl)butanoyl-3-(1-(sec-butyl)piperidin-4-yl)-1H-indole
5-(2-chlorobenzoyl)-3-(piperidin-4-yl)-1H-indole
5-(2-fluorobenzoyl)-3-(1-isobutylpiperidin-4-yl)-1H-indole
5-(2-bromobenzoyl)-3-(1-propylpiperidin-4-yl)-1H-indole
5-(2-iodobenzoyl)-3-(1-ethylpiperidin-4-yl-1H-indole
5-(4-iodobenzoyl)-3-(1-(sec-butyl)piperidin-4-yl)-1H-indole
5-(2-methoxybenzoyl)-3-(1-(2-pentyl)piperidin-4-yl)-1H-indole
5-(3-ethoxybenzoyl)-3-(1-pentylpiperidin-4-yl)-1H-indole
5-(4-propoxybenzoyl)-3-(1-butylpiperidin-4-yl)-1H-indole
5-(2-butoxybenzoyl)-3-(1-isobutylpiperidin-4-yl)-1H-indole hexyne-1,6-dioate
5-(4-butoxybenzoyl)-3-(1-(3-pentyl)piperidin-4-yl)-1H-indole
5-(3-methylbenzoyl)-3-(1-butylpiperidin-4-yl)-1H-indole
5-(4-ethylbenzoyl)-3-(1-ethylpiperidin-4-yl)-1H-indole
5-(2-ethylbenzoyl)-3-(1-(sec-butyl)piperidin-4-yl)-1H-indole benzoate
5-(3-propylbenzoyl)-3-(1-(2-pentyl)piperidin-4-yl)-1H-indole
5-(2-butylbenzoyl)-3-(1-pentylpiperidin-4-yl)-1H-indole
5-(4-butylbenzoyl)-3-(1-hexylpiperidin-4-yl)-1H-indole
5-(2-trifluoromethylbenzoyl)-3-(1-butylpiperidin-4-yl)-1H-indole chlorobenzoate
5-(3-trifluoromethoxybenzoyl)-3-(1-propylpiperidin-4-yl)-1H-indole
5-(2-dimethylaminobenzoyl)-3-(1-(sec-butyl piperidin-4-yl)-1H-indole
5-(4-phenylbutanoyl)-3-(1-pentylpiperidin-4-yl)-1H-indole 4-methylbenzoate
5-(1-naphthoyl)-3-(1-hexylpiperidin-4-yl)-1H-indole
5-(4-pyridinecarbonyl)-3-(1-ethylpiperidin-4-yl)-1H-indole
5-(N-phenyl)carboxamido-3-(1,2,3,6-tetrahydropyridin-4-yl)-2-methyl-1H-indole 2,4-dinitrobenzoate
5-(N-benzyl)carboxamido-3-(1-isobutyl-1,2,3,6-tetrahydropyridin-4-yl)-1H-indole
5-(N-(2-(4-chlorophenyl)ethyl))carboxamido-3-(1-ethyl-1,2,3,6-tetrahydropyridin-4-yl)-1H-indole 4-hydroxybenzoate
5-(N-(2-(3-methylphenyl)ethyl))carboxamido-3-(1-neopentyl-1,2,3,6-tetrahydropyridin-4-yl)-1H-indole
5-(N-(3-(2-methoxyphenyl)propyl))carboxamido-3-(1-(tert-butyl)-1,2,3,6-tetrahydropyridin-4-yl)-1H-indole
5-(N-(4-(4-trifluoromethylphenyl)butyl))carboxamido-3-(1-isopropyl-1,2,3,6-tetrahydropyridin-4-yl)-1H-indole 3-methoxybenzoate
5-(N-(4-chlorophenyl))carboxamido-3-(1-(2-pentyl)piperidin-4-yl)-1H-indole
5-(N-benzyl)carboxamido-3-(1-(3-pentyl)piperidin-4-yl)-1H-indole
5-(N-(2-phenethyl))carboxamido-3-(1-(sec-butyl)piperidin-4-yl)-2-methyl-1H-indole
5-(N-(3-phenpropyl))carboxamido-3-(piperidin-4-yl)-1H-indole
5-(N-(3-phenpropyl))carboxamido-3-(1-hexylpiperidin-4-yl)-1H-indole phthalate
5-(N-(4-phenbutyl))carboxamido-3-(1-pentylpiperidin-4-yl)-1H-indole
5-(N-methyl-N-ethanesulfonyl)amino-3-(1-hexyl-1,2,3,6-tetrahydropyridin-4-yl)-1H-indole 5-(N-ethyl-N-propanesulfonyl)amino-3-(1-(2-pentyl)-1,2,3,6-tetrahydropyridin-4-yl)-1H-indole
5-(N-isopropanesulfonyl)amino-3-(1-(3-pentyl)-1,2,3,6-tetrahydropyridin-4-yl)-1H-indole
5-(N-propyl-N-butanesulfonyl)amino-3-(1-(tert-butyl)-1,2,3,6-tetrahydropyridin-4-yl)-1H-indole
5-(N-isobutanesulfonyl)amino-3-(1,2,3,6-tetrahydropyridin-4-yl)-1H-indole methanesulfonate
5-(N-sec-butanesulfonyl)amino-3-(1-isobutyl-1,2,3,6-tetrahydropyridin-4-yl)-1H-indole
5-(N-tert-butanesulfonyl)amino-3-(1-(sec-butyl)-1,2,3,6-tetrahydropyridin-4-yl)-1H-indole
5-(N-butyl-N-benzenesulfonyl)amino-3-(1-isopropyl-1,2,3,6-tetrahydropyridin-4-yl)-1H-indole
5-(N,N-diethylaminosulfonyl)amino-3-(1-propyl-1,2,3,6-tetrahydropyridin-4-yl)-2-methyl-1H-indole
5-(N,N-dipropylaminosulfonyl)amino-3-(1-butyl-1,2,3,6-tetrahydropyridin-4-yl)-1H-indole
5-(N,N-diisopropylaminosulfonyl)amino-3-(1-neopentyl-1,2,3,6-tetrahydropyridin-4-yl)-1H-indole
5-(N,N-dibutylaminosulfonyl)amino-3-(1-(3-pentyl)-1,2,3,6-tetrahydropyridin-4-yl)-1H-indole
5-(N-ethanesulfonyl)amino-3-(1-(3-pentyl)piperidin-4-yl)-1H-indole phenylsulfonate
5-(N-propanesulfonyl)amino-3-(1-neopentylpiperidin-4-yl)-1H-indole
5-(N-isopropanesulfonyl)amino-3-(1-pentylpiperidin-4-yl)-1H-indole
5-(N-butanesulfonyl)amino-3-(piperidin-4-yl)-1H-indole
5-(N-isobutanesulfonyl)amino-3-(1-(sec-butyl)piperidin-4-yl)-1H-indole
5-(N-isopropyl-N-sec-butanesulfonyl)amino-3-(1-(tert-butyl)piperidin-4-yl)-1H-indole
5-(N-(tert-butyl)sulfonyl)amino-3-(1-butylpiperidin-4-yl)-1H-indole
5-(N,N-diethylaminosulfonyl)amino-3-(1-isobutylpiperidin-4-yl)-1H-indole
5-(N,N-dipropylaminosulfonyl)amino-3-(1-ethylpiperidin-4-yl)-2-methyl-1H-indole
5-(N,N-diisopropylaminosulfonyl)amino-3-(1-(2-pentyl)piperidin-4-yl)-1H-indole
5-(N,N-dibutylaminosulfonyl)amino-3-(1-hexylpiperidin-4-yl)-1H-indole
N-ethyl-N'-(3-(1-hexyl-1,2,3,6-tetrahydropyridin-4-yl)-1H-indol-5-yl)thiourea
N-isopropyl-N'-(3-(1-(sec-butyl)-1,2,3,6-tetrahydropyridin-4-yl)-1H-indol-5-yl)thiourea
N-(3-methoxy)phenyl-N'-(3-(1-isopropyl-1,2,3,6-tetrahydropyridin-4-yl)-1H-indol-5-yl)thiourea
N-(2-ethoxy)phenyl-N'-(2-methyl-3-(1-methyl-1,2,3,6-tetrahydropyridin-4-yl)-1H-indol-5-yl)thiourea
N-(2-ethoxy)phenyl-N'-(3-(1-(2-pentyl)-1,2,3,6-tetrahydropyridin-4-yl)-1H-indol-5-yl)thiourea
N-(3-ethoxy)phenyl-N'-(3-(1-(2-hexyl)-1,2,3,6-tetrahydropyridin-4-yl)-1H-indol-5-yl)thiourea
N-(3-propoxy)phenyl-N'-(3-(1,2,3,6-tetrahydropyridin-4-yl)-1H-indol-5-yl)thiourea
N-(3-isopropoxy)phenyl-N'-(3-(1-propyl-1,2,3,6-tetrahydropyridin-4-yl)-1H-indol-5-yl)thiourea
N-(4-isopropoxy)phenyl-N'-(3-(1-(3-pentyl)-1,2,3,6-tetrahydropyridin-4-yl)-1H-indol-5-yl)thiourea phenylacetate
N-(3-butoxy)phenyl-N'-(3-(1-(2-pentyl)-1,2,3,6-tetrahydropyridin-4-yl)-1H-indol-5-yl)thiourea hydrochloride
N-(2,3-dibromo)phenyl-N'-(3-(1-isopropyl-1,2,3,6-tetrahydropyridin-4-yl)-1H-indol-5-yl)thiourea
N-(2-bromo-3-iodo)phenyl-N'-(3-1-(2-pentyl)-1,2,3,6-tetrahydropyridin-4-yl)-1H-indol-5-yl)thiourea
N-(3,4-difluoro)phenyl-N'-(3-(1-butyl-1,2,3,6-tetrahydropyridin-4-yl)-1H-indol-5-yl)thiourea
N-(3-chloro-4-bromo)phenyl-N'-(3-(1-(3-pentyl)-1,2,3,6-tetrahydropyridin-4-yl)-1H-indol-5-yl)thiourea
N-(2-bromo-4-fluoro)phenyl-N'-(3-(1-methyl-1,2,3,6-tetrahydropyridin-4-yl)-1H-indol-5-yl)thiourea
N-(2,4-diiodo)phenyl-N'-(3-(1-(sec-butyl)-1,2,3,6-tetrahydropyridin-4-yl)-1H-indol-5-yl)thiourea
N-(2-chloro-5-iodo)phenyl-N'-(3-(1-hexyl-1,2,3,6-tetrahydropyridin-4-yl)-1H-indol-5-yl)thiourea
N-(2-fluoro-6-iodo)phenyl-N'-(3-(1-(tert-butyl)-1,2,3,6-tetrahydropyridin-4-yl)-1H-indol-5-yl)thiourea
N-(3-fluoro-5-chloro)phenyl-N'-(3-(1-(2-pentyl)-1,2,3,6-tetrahydropyridin-4-yl)-1H-indol-5-yl)thiourea
N-phenethyl-N'-(3-(1-isopropyl-1,2,3,6-tetrahydropyridin-4-yl)-1H-indol-5-yl)thiourea
N-(4-phenbutyl)-N'-(3-(1-(3-pentyl)-1,2,3,6-tetrahydropyridin-4-yl)-1H-indol-5-yl)thiourea
N-(2-trifluoromethyl)phenyl-N'-(3-(1-(2-pentyl)-1,2,3,6-tetrahydropyridin-4-yl)-1H-indol-5-yl)thiourea
N-(3-phenyl)phenyl-N'-(3-(1-(2-pentyl)-1,2,3,6-tetrahydropyridin-4-yl)-1H-indol-5-yl)thiourea
N-Propyl-N'-(3-(1-(2-pentyl)piperidin-4-yl)-1H-indol-5-yl)thiourea
N-butyl-N'-(3-(1-isopropylpiperidin-4-yl)-1H-indol-5-yl)thiourea
N-(2-methoxy)phenyl-N'-(3-(1-(sec-butyl)piperidin-4-yl)-1H-indol-5-yl)thiourea
N-(4-ethoxy)phenyl-N'-(3-(1-(2-pentyl)piperidin-4-yl)-1H-indol-5-yl)thiourea
N-(4-Propoxy)phenyl-N'-(2-methyl-3-(1-ethylpiperidin-4-yl)-1H-indol-5-yl)thiourea
N-(2-propoxy)phenyl-N'-(3-(1-(tert-butyl)piperidin-4-yl)-1H-indol-5-yl)thiourea
N-(2-isopropoxy)phenyl-N'-(3-(1-isobutylpiperidin-4-yl)-1H-indol-5-yl)thiourea
N-(4-butoxy)phenyl-N'-(3-piperidin-4-yl)-1H-indol-5-yl)thiourea
N-(2-butoxy)phenyl-N'-(3-(1-hexylpiperidin-4-yl)-1H-indol-5-yl)thiourea fumarate
N-(2-methoxy)phenyl-N'-(3-(1-(sec-butyl)piperidin-4-yl)-1H-indol-5-yl)thiourea
N-(2,3-dibromo)phenyl-N'-(3-(1-isopropylpiperidin-4-yl)-1H-indol-5-yl)thiourea
N-(2-bromo-3-iodo)phenyl-N'-(3-(1-(2-pentyl)piperidin-4-yl)-1H-indol-5-yl)thiourea
N-(3,4-difluoro)phenyl-N'-(3-(1-butylpiperidin-4-yl)-1H-indol-5-yl)thiourea
N-(3-chloro-4-bromo)phenyl-N'-(3-(1-(3-pentyl)piperidin-4-yl)-1H-indol-5-yl)thiourea
N-(2-bromo-4-fluoro)phenyl-N'-(3-(1-methylpiperidin-4-yl)-1H-indol-5-yl)thiourea
N-(2,4-diiodo)phenyl-N'-(3-(1-(sec-butyl)piperidin-4-yl)-1H-indol-5-yl)thiourea
N-(2-chloro-5-iodo)phenyl-N'-(3-(1-hexylpiperidin-4-yl)-1H-indol-5-yl)thiourea
N-(2-fluoro-6-iodo)phenyl-N'-(3-(1-(tert-butyl)piperidin-4-yl)-1H-indol-5-yl)thiourea
N-(3-fluoro-5-chloro)phenyl-N'-(3-(1-(2-pentyl)piperidin-4-yl)-1H-indol-5-yl)thiourea
N-(3-phenpropyl)-N'-(3-(1-(sec-butyl)piperidin-4-yl)-1H-indol-5-yl)thiourea
N-(4-trifluoromethyl)phenyl-N'-(3-(1-neopentylpiperidin-4-yl)-1H-indol-5-yl)thiourea
N-(4-phenyl)phenyl-N'-(3-(1-pentylpiperidin-4-yl)-1H-indol-5-yl)thiourea N-pentyl-N'-(3-(1-ethyl-1,2,3,4-tetrahydropyridin-4-yl)-1H-indol-5-yl)urea N-(1-buten-4-yl)-N'-(3-(1-isopropyl-1,2,3,4-tetrahydropyridin-4-yl)-1H-indol-5-yl)urea N-(1-penten-5-yl)-N'-(3-(1-isobutyl-1,2,3,4-tetrahydropyridin-4-yl)-1H-indol-5-yl)urea hydrochloride N-(3-penten-5-yl)-N'-(3-(1-(tert-butyl)-1,2,3,4-tetrahydropyridin-4-yl)-1H-indol-5-yl)urea N-(2-hexen-6-yl)-N'-(3-(1-(2-pentyl)-1,2,3,4-tetrahydropyridin-4-yl)-1H-indol-5-yl)urea N-(4-hexen-6-yl)-N'-(3-(1-neopentyl-1,2,3,4-tetrahydropyridin-4-yl)-1H-indol-5-yl)urea N-cyclobutyl-N'-(3-(1,2,3,4-tetrahydropyridin-4-yl)-1H-indol-5-yl)urea N-cycloheptyl-N'-(3-(1-pentyl-1,2,3,4-tetrahydropyridin-4-yl)-1H-indol-5-yl)urea N-(3-chloro)phenyl-N'-(2-methyl-3-(1-propyl-1,2,3,4-tetrahydropyridin-4-yl)-1H-indol-5-yl)urea N-(4-bromo)phenyl-N'-(3-(1-(sec-butyl)-1,2,3,4-tetrahydropyridin-4-yl)-1H-indol-5-yl)urea N-(2-bromo)phenyl-N'-(3-(1-(3-pentyl)-1,2,3,4-tetrahydropyridin-4-yl)-1H-indol-5-yl)urea N-(2-fluoro)phenyl-N°-(3-(1-(2-pentyl)-1,2,3,4-tetrahydropyridin-4-yl)-1H-indol-5-yl)urea N-(2-iodo)phenyl-N'-(3-(1-ethyl-1,2,3,4-tetrahydropyridin-4-yl)-1H-indol-5-yl)urea N-(4-iodo)phenyl-N'-(3-(1-(tert-butyl)-1,2,3,4-tetrahydropyridin-4-yl)-1H-indol-5-yl)urea N-(3-methoxy)phenyl-N'-(3-(1-butyl-1,2,3,4-tetrahydropyridin-4-yl)-1H-indol-5-yl)urea N-(3-ethoxy)phenyl-N'-(3-(1-pentyl-1,2,3,4-tetrahydropyridin-4-yl)-1H-indol-5-yl)urea N-(2-propoxy)phenyl-N'-(3-(1-(tert-butyl)-1,2,3,4-tetrahydropyridin-4-yl)-1H-indol-5-yl)urea N-(4-propoxy)phenyl-N'-(3-(1-hexyl-1,2,3,4-tetrahydropyridin-4-yl)-1H-indol-5-yl)urea N-(3-isopropoxy)phenyl-N'-(3-(1-isopropyl-1,2,3,4-tetrahydropyridin-4-yl)-1H-indol-5-yl)urea N-(4-butoxy)phenyl-N'-(3-(1-methyl-1,2,3,4-tetrahydropyridin-4-yl)-1H-indol-5-yl)urea N-(2-butoxy)phenyl-N'-(3-(1-butyl-1,2,3,4-tetrahydropyridin-4-yl)-1H-indol-5-yl)urea N-(3-formyl) phenyl -N'-(3-(1-pentyl -1,2,3,4-tetrahydropyridin-4-yl)-1H-indol-5-yl)urea N-(4-acetyl)phenyl-N'-(3-(1-hexyl-1,2,3,4-tetrahydropyridin-4-yl)-1H-indol-5-yl)urea N-(2-propanoyl)phenyl-N'-(3-(1-isobutyl-1,2,3,4-tetrahydropyridin-4-yl)-1H-indol-5-yl)urea N-(4-propanoyl)phenyl-N'-(3-(1-neopentyl-1,2,3,4-tetrahydropyridin-4-yl)-1H-indol-5-yl)urea N-(2-methylthio)phenyl-N'-(3-(1-butyl-1,2,3,4-tetrahydropyridin-4-yl)-1H-indol-5-yl)urea N-(3-ethylthio)phenyl-N'-(3-(1-pentyl-1,2,3,4-tetrahydropyridin-4-yl)-1H-indo1—5-yl)urea N-(2-propylthio)phenyl-N'-(3-(1-(tert-butyl-1,2,3,4-tetrahydropyridin-4-yl)-1H-indol-5-yl)urea fumarate N-(4-propylthio)phenyl-N'-(3-(1-hexyl-1,2,3,4-tetrahydropyridin-4-yl)-1H-indol-5-yl)urea N-(2-butylthio)phenyl-N'-(3-(1-ethyl-1,2,3,4-tetrahydropyridin-4-yl)-1H-indol-5-yl)urea N-(4-butylthio)phenyl-N'-(3-(1-isobutyl-1,2,3,4-tetrahydropyridin-4-yl)-1H-indol-5-yl)urea N-(3-methyl)phenyl-N'-(3-(1-propyl-1,2,3,4-tetrahydropyridin-4-yl)-1H-indol-5-yl)urea N-(4-ethyl)phenyl-N'-(3-(1-sec-butyl)-1,2,3,4-tetrahydropyridin-4-yl)-1H-indol-5-yl)urea N-(2-ethyl)phenyl-N'-(3-(1-(3-pentyl)-1,2,3,4-tetrahydropyridin-4-yl)-1H-indol-5-yl)urea N-(3-propyl)phenyl-N'-(3-(1-(2-pentyl)-1,2,3,4-tetrahydropyridin-4-yl)-1H-indol-5-yl)urea N-(2-isopropyl)phenyl-N'-(3-(1-ethyl-1,2,3,4-tetrahydropyridin-4-yl)-1H-indol-5-yl)urea N-(3-butyl)phenyl-N'-(3-(1-propyl-1,2,3,4-tetrahydropyridin-4-yl)-1H-indol-5-yl)urea N-(4-methoxycarbonyl)phenyl-N'-(3-(1-(sec-butyl)-1,2,3,4-tetrahydropyridin-4-yl)-1H-indol-5-)urea N-(3-ethoxycarbonyl)phenyl-N'-(3-(1-(2-pentyl)-1,2,3,4-tetrahydropyridin-4-yl)-1H-indol-5-yl)urea N-(2-propoxycarbonyl)phenyl-N'-(3-(1-ethyl-1,2,3,4-tetrahydropyridin-4-yl)-1H-indol-5-yl)urea N-(4-propoxycarbonyl)phenyl-N'-(3-(1-isobutyl-1,2,3,4-tetrahydropyridin-4-yl)-1H-indol-5-yl)urea N-(3-butoxycarbonyl)phenyl-N'-(3-(1-neopentyl-1,2,3,4-tetrahydropyridin-4-yl)-1H-indol-5-yl)urea N-(2,3-dibromo)phenyl-N'-(3-(1-isopropyl-1,2,3,6-tetrahydropyridin-4-yl)-1H-indol-5-yl)urea N-(2-bromo-3-iodo)phenyl-N'-(3-(1-(2-pentyl)-1,2,3,6-tetrahydropyridin-4-yl)-1H-indol-5-yl)urea N-(3,4-difluoro)phenyl-N'-(3-(1-butyl-1,2,3,6-tetrahydropyridin-4-yl)-1H-indol-5-yl)urea N-(3-chloro-4-bromo)phenyl-N'-(3-(1-(3-pentyl)-1,2,3,6-tetrahydropyridin-4-yl)-1H-indol-5-yl)urea N-(2-bromo-4-fluoro)phenyl-N'-(3-(1-methyl-1,2,3,6-tetrahydropyridin-4-yl)-1H-indol-5-yl)urea N-(2,4-diiodo)phenyl-N'-(3-(1-(sec-butyl)-1,2,3,6-tetrahydropyridin-4-yl)-1H-indol-5-yl)urea N-(2-chloro-5-iodo)phenyl-N'-(3-(1-hexyl-1,2,3,6-tetrahydropyridin-4-yl)-1H-indol-5-yl)urea N-(2-fluoro-6-iodo)phenyl-N'-(3-(1-(tert-butyl)-1,2,3,6-tetrahydropyridin-4-yl)-1H-indol-5-yl)urea N-(3-fluoro-5-chloro)phenyl-N'-(3-(1-(2-pentyl)-1,2,3,6-tetrahydropyridin-4-yl)-1H-indol-5-yl)urea N-(4-phenbutyl)-N'-(3-(1-isopropyl-1,2,3,6-tetrahydropyridin-4-yl)-1H-indol-5-yl)urea N-phenyl-N-propyl-N'-(3-(1-isobutyl-1,2,3,6-tetrahydropyridin-4-yl)-1H-indol-5-yl)urea N-phenyl-N-butyl-N'-(3-(1-(tert-butyl)-1,2,3,6-tetrahydropyridin-4-yl)-1H-indol-5-yl)urea N-methyl-N-propyl-N'-(3-(1-(3-pentyl)-1,2,3,6-tetrahydropyridin-4-yl)-1H-indol-5-yl)urea N-ethyl-N-isopropyl-N'-(3-(1-(3-pentyl)-1,2,3,6-tetrahydropyridin-4-yl)-1H-indol-5-yl)urea N,N-dipropyl-N'-(3-(1-isobutyl-1,2,3,6-tetrahydropyridin-4-yl)-1H-indol-5-yl)urea N-butyl-N-propyl-N'-(3-(1-isobutyl-1,2,3,6-tetrahydropyridin-4-yl)-1H-indol-5-yl)urea N-butyl-N-isopropyl-N'-(3-(1-isopropyl-1,2,3,6-tetrahydropyridin-4-yl)-1H-indol-5-yl)urea N-hexyl -N'-(3-(1-propylpiperidin-4-yl)-1H-indol-5-yl)urea N-(2-buten-4-yl)-N'-(3-(1-butylpiperidin-4-yl)-1H-indol-5-yl)urea N-(2-penten-5-yl)-N'-(3-(1-(sec-butyl)piperidin-4-yl)-H-indol-5-yl)urea N-(1-hexen-6-yl)-N'-(3-(1-pentylpiperidin-4-yl)-1H-indol-5-yl)urea N-(3-hexen-6-yl)-N'-(3-(1-(3-pentyl)piperidin-4-yl)-H-indol-5-yl)urea N-cyclopropyl -N'-(3-(1-hexylpiperidin-4-yl)-1H-indol-5-yl)urea N-cyclopentyl-N'-(3-(1-(3-pentyl)piperidin-4-yl)-1H-indol-5-yl)urea N-cyclooctyl-N'-(3-(1-(tert-butyl)piperidin-4-yl)-1H-indol-5-yl)urea N-(2-chloro)phenyl-N'-(3-(1-butylpiperidin-4-yl)-1H-indol-5-yl)urea
N-(3-bromo)phenyl-N'-(3-(1-pentylpiperidin-4-yl)-1H-indol-5-yl)urea
N-(3-fluoro)phenyl-N'-(3-(1-hexylpiperidin-4-yl)-1H-indol-5-yl)urea
N-(3-iodo)phenyl-N'-2-methyl-3-(1-butylpiperidin-4-yl)-1H-indol-5-yl)urea
N-(3-phenyl)phenyl-N -(3-(1-propylpiperidin-4-yl)-1H-indol-5-yl)urea
N-(4-ethoxy)phenyl-N'-(3-(1-( sec-butyl)piperidin-4-yl)-1H-indol-5-yl)urea
N-(2-ethoxy )phenyl-N'-(3-(1-neopentylpiperidin-4-yl)-H-indol-5-yl)urea
N-(3-propoxy)phenyl-N'-(3-(1-(2-pentyl)piperidin-4-yl)-1H-indol-5-yl)urea
N-(2-isopropoxy)phenyl-N'-(3-(1-ethylpiperidin-4-yl)-H-indol-5-yl)urea
N-(4-isopropoxy)phenyl-N'-(3-(1-isobutylpiperidin-4-yl)-1H-indol-5-yl)urea
N-(3-butoxy)phenyl-N'-(3-(1-propylpiperidin-4-yl)-1H-indol-5-yl)urea
N-(4-formyl)phenyl-N'-(3-(1-(sec-butyl)piperidin-4-yl)-1H-indol-5-yl)urea
N-(2-formyl)phenyl-N'-(3-(1-(3-pentyl)piperidin-4-yl)-H-indol-5-yl)urea
N-(3-acetyl)phenyl-N'-(3-(1-(2-pentyl)piperidin-4-yl)-H-indol-5-yl)urea phenylpropionate
N-(3-propanoyl)phenyl-N'-(3-(1-pentylpiperidin-4-yl)-H-indol-5-yl)urea
N-(3-ethylthio)phenyl-N'-(3-(1-propylpiperidin-4-yl)-H-indol-5-yl)urea
N-(2-ethylthio)phenyl-N'-(3-(1-(3-pentyl)piperidin-4-yl)-1H-indol-5-yl)urea
N-(3-propylthio)phenyl-N'-(3-piperidin-4-yl)-1H-indol-5-yl)urea
N-(3-isopropylthio)phenyl-N'-(3-(1-isopropylpiperidin-4-yl)-1H-indol-5-yl)urea
N-(2-methyl)phenyl-N'-(3-(1-propylpiperidin-4-yl)-1H-indol-5-yl)urea
N-(3-ethyl)phenyl-N'-(3-(1-pentylpiperidin-4-yl)-1H-indol-5-yl)urea
N-(2-propyl)phenyl-N'-(3-(1-(tert-butyl)piperidin-4-yl)-1H-indol-5-yl)urea
N-(3-isopropyl)phenyl-N'-(3-(1-isopropylpiperidin-4-yl)-1H-indol-5-yl)urea
N-(4-butyl)phenyl-N'-(3-(1-methylpiperidin-4-yl)-1H-indol-5-yl)urea
N-(2-butyl)phenyl-N'-(3-(1-butylpiperidin-4-yl)-1H-indol-5-yl)urea
N-(3-methoxycarbonyl)phenyl-N'-(3-(1-pentylpiperidin-4-yl)-1H-indol-5-yl)urea
N-(2-ethoxycarbonyl)phenyl-N'-(3-(1-(tert-butyl)piperidin-4-yl)-1H-indol-5-yl)urea
N-(4-ethoxycarbonyl)phenyl-N'-(3-(1-hexylpiperidin-4-yl)-1H-indol-5-yl)urea
N-(3-propoxycarbonyl)phenyl-N'-(3-(1-isobutylpiperidin-4-yl)-1H-indol-5-yl)urea
N-(2-butoxycarbonyl)phenyl-N'-(3-(1-propylpiperidin-4-yl)-1H-indol-5-yl)urea
N-(2,3-dibromo)phenyl-N'-(3-(1-isopropylpiperidin-4-yl)-1H-indol-5-yl)urea
N-(2-bromo-3-iodo)phenyl-N'-(3-(1-(2-pentyl)piperidin-4-yl)-1H-indol-5-yl)urea
N-(3,4-difluoro)phenyl-N'-(3-(1-butylpiperidin-4-yl)-1H-indol-5-yl)urea
N-(3-chloro-4-bromo)phenyl-N'-(3-(1-(3-pentyl)piperidin-4-yl)-1H-indol-5-yl)urea
N-(2-bromo-4-fluoro)phenyl-N'-(3-(1-methylpiperidin-4-yl)-1H-indol-5-yl)urea
N-(2,4-diiodo)phenyl-N'-(3-(1-(sec-butyl)piperidin-4-yl)-1H-indol-5-yl)urea
N-(2-chloro-5-iodo)phenyl-N'-(3-(1-hexylpiperidin-4-yl)-1H-indol-5-yl)urea
N-(2-fluoro-6-iodo)phenyl-N'-(3-(1-(tert-butyl)piperidin-4-yl)-1H-indol-5-yl)urea
N-(3-fluoro-5-chloro)phenyl-N'-(3-(1-(2-pentyl)piperidin-4-yl)-1H-indol-5-yl)urea
N-(3-phenpropyl)-N'-(3-(1-propylpiperidin-4-yl)-1H-indol-5-yl)urea
N-ethyl-N-phenyl-N'-(3-(1-butylpiperidin-4-yl)-1H-indol-5-yl)urea
N-isopropyl-N-phenyl-N'-(3-(1-(sec-butyl)piperidin-4-yl)-1H-indol-5-yl)urea
N-ethyl-N-methyl-N'-(3-(1-(2-pentyl)piperidin-4-yl)-1H-indol-5-yl)urea
N-(methyl-N-isopropyl-N'-(3-(1-neopentylpiperidin-4-yl)-1H-indol-5-yl)urea
N-(ethyl-N-propyl-N'-(3-(1-neopentylpiperidin-4-yl)-1H-indol-5-yl)urea
N-ethyl-N-butyl-N'-(3-(1-(2-pentylpiperidin-4-Yl)-1H-indol-5-yl)urea
N-propyl-N-isopropyl-N -(3-(1-isobutylpiperidin-4-yl)-H-indol-5-yl)urea
N,N-diisopropyl-N'-(3-1-butylpiperidin-4-yl)-1H-indol-5-yl)urea
N,N-dibutyl-N'-(3-(1-butylpiperidin-4-yl)-1H-indol-5-yl) urea
5-isopropoxycarbonylamino-3-(1-ethyl-1,2,3,6-tetrahydropyridin-4-yl)-2-ethyl-1H-indole
5-(1-buten-4-yloxy)carbonylamino-3-(1-isopropyl-1,2,3,6-tetrahydropyridin-4-yl)-1H-indole hydrochloride
5-(1-penten-5-yloxy)carbonylamino-3-(1-isobutyl-1,2,3,6-tetrahydropyridin-4-yl)-1H-indole
5-(1-buten-4-yloxy)carbonylamino-3-(1-isopropyl-1,2,3,6-tetrahydropyridin-4-yl)-1H-indole
5-(3-penten-5-yloxy)carbonylamino-3-(1-1,2,3,6-tetrahydropyridin-4-yl)-1H-indole
5-(2-hexen-6-yloxy)carbonylamino-3-(1-(2-pentyl)-1,2,3,6-tetrahydropyridin-4-yl)-1H-indole
5-(4-hexen-6-yloxy)carbonylamino-3-(1-(neopentyl)-1,2,3,6-tetrahydropyridin-4-yl)-1H-indole
5-(2-chlorophenoxy)carbonylamino-3-(1-(3-pentyl)-1,2,3,6-tetrahydropyridin-4-yl)-1H-indole
5-(3-fluorophenoxy)carbonylamino-3-(1-(sec-butyl)-1,2,3,6-tetrahydropyridin-4-yl)-1H-indole
5-(3-bromophenoxy)carbonylamino-3-(1-methyl-1,2,3,6-tetrahydropyridin-4-yl)-1H-indole
5-(2-bromophenoxy)carbonylamino-3-(1-neopentyl-1,2,3,6-tetrahydropyridin-4-yl)-1H-indole
5-(3-iodophenoxy)carbonylamino-3-(1-(tert-butyl)-1,2,3,6-tetrahydropyridin-4-yl)-1H-indole
5-(3-methoxyphenoxy)carbonylamino-3-(1-isopropyl-1,2,3,6-tetrahydropyridin-4-yl)-1H-indole
5-(4-ethoxyphenoxy)carbonylamino-3-(1-methyl-1,2,3,6-tetrahydropyridin-4-yl)-1H-indole
5-(2-ethoxy)phenoxy)carbonylamino-3-(1-butyl-1,2,3,6-tetrahydropyridin-4-yl)-1H-indole
5-(3-propoxyphenoxy)carbonylamino-3-(1-pentyl-1,2,3,6-tetrahydropyridin-4-yl)-1H-indole
5-(2-butoxyphenoxy)carbonylamino-3-(1-(2-pentyl)-1,2,3,6-tetrahydropyridin-4-yl)-1H-indole
5-(4-butoxyphenoxy)carbonylamino-3-(1-hexyl-1,2,3,6-tetrahydropyridin-4-yl)-1H-indole
5-cyclobutoxycarbonylamino-3-(1-(sec-butyl)-1,2,3,6-tetrahydropyridin-4-yl)-1H-indole 5-cyclooctyloxycarbonylamino-3-(1-butyl-1,2,3,6-tetrahydropyridin-4-yl)-1H-indole
5-(butoxymethoxy)carbonylamino-3-(1-propyl-1,2,3,6-tetrahydropyridin-4-yl)-1H-indole
5-(ethoxypropoxy)carbonylamino-3-(1-methyl-1,2,3,6-tetrahydropyridin-4-yl)-1H-indole
5-butoxycarbonylamino-3-(1-propylpiperidin-4-yl)-2-propyl-1H-indole
5-(2-buten-4-yloxy)carbonylamino-3-(piperidin-4-yl)-1H-indole
5-(2-penten-5-yloxy)carbonylamino-3-(1-(sec-butyl)piperidin-4-yl)-1H-indole
5-(1-hexen-6-yloxy)carbonylamino-3-(1-pentylpiperidin-4-yl)-1H-indole
5-(3-hexen-6-yloxy)carbonylamino-3-(1-(3-pentyl)piperidin-4-yl)-1H-indole
5-(3-chlorophenoxy)carbonylamino-3-(1-hexylpiperidin-4-yl)-1H-indole
5-(2-fluorophenoxy)carbonylamino-3-(1-butylpiperidin-4-yl)-1H-indole
5-(4-fluorophenoxy)carbonylamino-3-(1-pentylpiperidin-4-yl)-1H-indole
5-(4-bromophenoxy)carbonylamino-3-(1-propylpiperidin-4-yl)-1H-indole
5-(2-iodophenoxy)carbonylamino-3-(1-isobutylpiperidin-4-yl)-1H-indole
5-(4-iodophenoxy)carbonylamino-3-(1-(2-pentyl)piperidin-4-yl)-1H-indole
5-(3-chlorophenoxy)carbonylamino-3-(1-hexylpiperidin-4-yl)-1H-indole
5-(2-methoxyphenoxy)carbonylamino-3-(1-hexylpiperidin-4-yl)-2-ethyl-1H-indole citrate
5-(3-ethoxyphenoxy)carbonylamino-3-(1-propylpiperidin-4-yl)-1H-indole
5-(4-propoxyphenoxy)carbonylamino-3-(1-(sec-butyl)piperidin-4-yl)-1H-indole
5-(2-propoxyphenoxy)carbonylamino-3-(1-(2-pentyl)piperidin-4-yl)-1H-indole
5-(3-butoxyphenoxy)carbonylamino-3-(1-neopentylpiperidin-4-yl)-1H-indole
5-cyclopropoxycarbonylamino-3-(1-(tert-butyl)piperidin-4-yl)-1H-indole
5-cyclohexyloxycarbonylamino-3-(1-isobutylpiperidin-4-yl)-1H-indole
5-cyclooctyloxycarbonylamino-3-(1-isopropylpiperidin-4-yl)-1H-indole
5-(propoxyethoxy)carbonylamino-3-(1-ethylpiperidin-4-yl)-1H-indole
5-(4-methoxybutoxy)carbonylamino(1-ethylpiperidin-4-yl)-1H-indole
5-(acetyl)amino-3-(1-hexyl-1,2,3,6-tetrahydropyridin-4-yl)-1H-indole
5-(butyroyl)amino-3-(1-(2-pentyl)-1,2,3,6-tetrahydropyridin-4-yl)-1H-indole
5-(pentanoyl)amino-3-(1-pentyl-1,2,3,6-tetrahydropyridin-4-yl)-1H-indole glycollate
5-(2-methylbutanoyl)amino-3-(1-(sec-butyl)-1,2,3,6-tetrahydropyridin-4-yl)-1H-indole
5-(2,2-dimethylpropanoyl)amino-3-(1-isobutyl-1,2,3,6-tetrahydropyridin-4-yl)-1H-indole
5-(heptanoyl)amino-3-(1-isopropyl-1,2,3,6-tetrahydropyridin-4-yl)-1H-indole
5-(cyclooctylcarbonyl)amino-3-(1-isobutyl-1,2,3,6-tetrahydropyridin-4-yl)-1H-indole
5-(4-phenylbutanoyl)amino-3-(1-pentyl-1,2,3,6-tetrahydropyridin-4-yl)-1H-indole
5-(phenoxyacetyl)amino-3-(1-(3-pentyl)-1,2,3,6-tetrahydropyridin-4-yl)-1H-indole
5-(4-phenoxybutanoyl)amino-3-(1-hexyl-1,2,3,6-tetrahydropyridin-4-yl)-1H-indole
5-(butoxyacetyl)amino-3-(1-(3-pentyl)-1,2,3,6-tetrahydropyridin-4-yl)-1H-indole
5-(4-ethoxybutanoyl)amino-3-(1,2,3,6-tetrahydropyridin-4-yl)-1H-indole tartrate
5-(butoxycarbonylacetyl)amino-3-(1-(sec-butyl)-1,2,3,6-tetrahydropyridin-4-yl)-1H-indole
5-(4-butoxycarbonylbutanoyl)amino-3-(1-hexyl-1,2,3,6-tetrahydropyridin-4-yl)-1H-indole
5-benzoylamino-3-(1-ethyl-1,2,3,6-tetrahydropyridin-4-yl)-1H-indole hydrochloride
5-benzoylamino-3-(1-propyl-1,2,3,6-tetrahydropyridin-4-yl)-1H-indole
5-benzoylamino-3-(1-isopropyl-1,2,3,6-tetrahydropyridin-4-yl)-1H-indole
5-benzoylamino-3-(1-butyl-1,2,3,6-tetrahydropyridin-4-yl)-1H-indole
5-benzoylamino-3-(1-isobutyl-1,2,3,6-tetrahydropyridin-4-yl)-1H-indole
5-benzoylamino-3-(1-(sec-butyl)-1,2,3,6-tetrahydropyridin-4-yl)-1H-indole
5-benzoylamino-3-(1-(tert-butyl)-1,2,3,6-tetrahydropyridin-4-yl)-1H-indole
5-benzoylamino-3-(1-pentyl-1,2,3,6-tetrahydropyridin-4-yl)-1H-indole
5-benzoylamino-3-(1-(2-pentyl)-1,2,3,6-tetrahydropyridin-4-yl)-1H-indole
5-benzoylamino-3-(1-(3-pentyl)-1,2,3,6-tetrahydropyridin-4-yl)-1H-indole
5-benzoylamino-3-(1-neopentyl-1,2,3,6-tetrahydropyridin-4-yl)-1H-indole propanesulfonate
5-benzoylamino-3-(1-hexyl-1,2,3,6-tetrahydropyridin-4-yl)-1H-indole
5-(4-fluorobenzoyl)amino-3-(1-ethyl-1,2,3,6-tetrahydropyridin-4-yl)-1H-indole fumarate
5-(4-fluorobenzoyl)amino-3-(1-propyl-1,2,3,6-tetrahydropyridin-4-yl)-1H-indole
5-(4-fluorobenzoyl)amino-3-(1-isopropyl-1,2,3,6-tetrahydropyridin-4-yl)-1H-indole
5-(4-fluorobenzoyl)amino-3-(1-butyl-1,2,3,6-tetrahydropyridin-4-yl)-1H-indole
5-(4-fluorobenzoyl)amino-3-(1-isobutyl-1,2,3,6-tetrahydropyridin-4-yl)-1H-indole
5-(4-fluorobenzoyl)amino-3-(1-(sec-butyl)-1,2,3,6-tetrahydropyridin-4-yl)-1H-indole
5-(4-fluorobenzoyl)amino-3-(1-(tert-butyl)-1,2,3,6-tetrahydropyridin-4-yl)-1H-indole
5-(4-fluorobenzoyl)-N-methylamino-3-(1-pentyl-1,2,3,6-tetrahydropyridin-4-yl)-1H-indole naphthalene-1-sulfonate
5-(4-fluorobenzoyl)amino-3-(1-(2-pentyl)-1,2,3,6-tetrahydropyridin-4-yl)-1H-indole
5-(4-fluorobenzoyl)amino-3-(1-(3-pentyl)-1,2,3,6-tetrahydropyridin-4-yl)-1H-indole
5-(4-fluorobenzoyl)amino-3-(1-neopentyl-1,2,3,6-tetrahydropyridin-4-yl)-1H-indole
5-(4-fluorobenzoyl)amino-3-(1-hexyl-1,2,3,6-tetrahydropyridin-4-yl)-1H-indole
5-(2-chlorobenzoyl)amino-3-(1-ethyl-1,2,3,6-tetrahydropyridin-4-yl)-1H-indole
5-(2-chlorobenzoyl)amino-3-(1-propyl-1,2,3,6-tetrahydropyridin-4-yl)-1H-indole
5-(2-chlorobenzoyl)amino-3-(1-isopropyl-1,2,3,6-tetrahydropyridin-4-yl)-1H-indole
5-(2-chlorobenzoyl)amino-3-(1-butyl-1,2,3,6-tetrahydropyridin-4-yl)-1H-indole 5-(2-chlorobenzoyl)amino-3-(1-isobutyl-1,2,3,6-tetrahydropyridin-4-yl)-1H-indole
5-(2-chlorobenzoyl)amino-3-(1-(sec-butyl)-1,2,3,6-tetrahydropyridin-4-yl)-1H-indole
5-(2-chlorobenzoyl)amino-3-(1-(tert-butyl)-1,2,3,6-tetrahydropyridin-4-yl)-1H-indole
5-(2-chlorobenzoyl-N-ethylamino-3-(1-pentyl-1,2,3,6-tetrahydropyridin-4-yl)-1H-indole
5-(2-chlorobenzoyl)amino-3-(1-(2-pentyl)-1,2,3,6-tetrahydropyridin-4-yl)-1H-indole
5-(2-chlorobenzoyl)amino-3-(1-(3-pentyl)-1,2,3,6-tetrahydropyridin-4-yl)-1H-indole
5-(2-chlorobenzoyl)amino-3-(1-neopentyl-1,2,3,6-tetrahydropyridin-4-yl)-1H-indole
5-(2-chlorobenzoyl)amino-3-(1-hexyl-1,2,3,6-tetrahydropyridin-4-yl)-1H-indole
5-(3-bromobenzoyl)amino-3-(1-propyl-1,2,3,6-tetrahydropyridin-4-yl)-1H-indole
5-(2-iodobenzoyl)-N-propylamino-3-(1-(sec-butyl)-1,2,3,6-tetrahydropyridin-4-yl)-1H-indole
5-(3-ethylbenzoyl)amino-3-(1-propyl-1,2,3,6-tetrahydropyridin-4-yl)-1H-indole
5-(4-propylbenzoyl)amino-3-(1-(tert-butyl)-1,2,3,6-tetrahydropyridin-4-yl)-1H-indole
5-(2-propylbenzoyl)amino-3-(1-neopentyl-1,2,3,6-tetrahydropyridin-4-yl)-1H-indole
5-(3-butylbenzoyl)amino-3-(1-propyl-1,2,3,6-tetrahydropyridin-4-yl)-1H-indole
5-(4-ethoxybenzoyl)amino-3-(1-(sec-butyl)-1,2,3,6-tetrahydropyridin-4-yl)-1H-indole
5-(2-ethoxybenzoyl)-N-isopropylamino-3-(1-(3-pentyl)-1,2,3,6-tetrahydropyridin-4-yl)-1H-indole
5-(3-propoxybenzoyl)amino-3-(1-(2-pentyl)-1,2,3,6-tetrahydropyridin-4-yl)-1H-indole
5-(2-butoxybenzoyl)amino-3-(1-ethyl-1,2,3,6-tetrahydropyridin-4-yl)-1H-indole
5-(4-butoxybenzoyl)amino-3-(1-isobutyl-1,2,3,6-tetrahydropyridin-4-yl)-1H-indole
5-(3-pentoxybenzoyl)amino-3-(1-propyl-1,2,3,6-tetrahydropyridin-4-yl)-1H-indole
5-(3-hexyloxybenzoyl)amino-3-(1-(sec-butyl)-1,2,3,6-tetrahydropyridin-4-yl)-1H-indole
5-(3-heptyloxybenzoyl)amino-3-(1-hexyl-1,2,3,6-tetrahydropyridin-4-yl)-1H-indole
5-(2-octyloxybenzoyl)amino-3-(1-neopentyl-1,2,3,6-tetrahydropyridin-4-yl)-1H-indole
5-(4-octyloxybenzoyl)amino-3-(1-(2-pentyl)-1,2,3,6-tetrahydropyridin-4-yl)-1H-indole
5-3-octyloxybenzoyl)amino-3-(1-(tert-butyl)-1,2,3,6-tetrahydropyridin-4-yl)-1H-indole
5-3-methylthiobenzoyl)amino-3-(1-isopropyl-1,2,3,6-tetrahydropyridin-4-yl)-1H-indole
5-4-propylthiobenzoyl)-N-butylamino-3-(1-methyl-1,2,3,6-tetrahydropyridin-4-yl)-1H-indole
5-2-propylthiobenzoyl)amino-3-(1-butyl-1,2,3,6-tetrahydropyridin-4-yl)-1H-indole
5-3-butylthiobenzoyl)amino-3-(1-hexyl-1,2,3,6-tetrahydropyridin-4-yl)-1H-indole
5-2-nitrobenzoyl)amino-3-(1-isopropyl-1,2,3,6-tetrahydropyridin-4-yl)-1H-indole
5-(2-cyanobenzoyl)amino-3-(1-isopropyl-1,2,3,6-tetrahydropyridin-4-yl)-1H-indole
5-(2-(dimethylamino)benzoyl)amino-3-(1-neopentyl-1,2,3,6-tetrahydropyridin-4-yl)-1H-indole
5-(3-(diethylamino)benzoyl)amino-3-(1-(sec-butyl)-1,2,3,6-tetrahydropyridin-4-yl)-1H-indole
5-(4-(dipropylamino)benzoyl)amino-3-(1-propyl-1,2,3,6-tetrahydropyridin-4-yl)-1H-indole
5-(2-trifluoromethoxybenzoyl)amino-3-(1-ethyl-1,2,3,6-tetrahydropyridin-4-yl)-1H-indole
5-(3-trifluoromethoxybenzoyl)amino-3-(1-isobutyl-1,2,3,6-tetrahydropyridin-4-yl)-1H-indole
5-(3-formylbenzoyl)amino-3-(1-(2-pentyl)-1,2,3,6-tetrahydropyridin-4-yl)-1H-indole
5-(3-acetylbenzoyl)amino-3-(1-hexyl-1,2,3,6-tetrahydropyridin-4-yl)-1H-indole
5-(2-(propanoyl)benzoyl)amino-3-(1-butyl-1,2,3,6-tetrahydropyridin-4-yl)-1H-indole
5-(4-(propanoyl)benzoyl)amino-3-(1-pentyl-1,2,3,6-tetrahydropyridin-4-yl)-1H-indole
5-(3-(butanoyl)benzoyl)amino-3-(1-methyl-1,2,3,6-tetrahydropyridin-4-yl)-1H-indole
5-(3-(benzoyl)benzoyl)amino-3-(1-(3-pentyl)-1,2,3,6-tetrahydropyridin-4-yl)-1H-indole
5-(3-methanesulfonylbenzoyl)amino-3-(1-(sec-butyl)-1,2,3,6-tetrahydropyridin-4-yl)-1H-indole
5-(3-ethanesulfonylbenzoyl)amino-3-(1-propyl-1,2,3,6-tetrahydropyridin-4-yl)-1H-indole
5-(2-butanesulfonylbenzoyl)amino-3-(1-ethyl-1,2,3,6-tetrahydropyridin-4-yl)-1H-indole
5-(3-butanesulfonylbenzoyl)amino-3-(1-isobutyl-1,2,3,6-tetrahydropyridin-4-yl)-1H-indole
5-(2-phenylbenzoyl)amino-3-(1-(2-pentyl)-1,2,3,6-tetrahydropyridin-4-yl)-1H-indole
5-(2,3-dibromo)benzoylamino-3-(1-isopropyl-1,2,3,6-tetrahydropyridin-4-yl)-1H-indole
5-(2-bromo-3-iodo)benzoylamino-3-(1-(2-pentyl)-1,2,3,6-tetrahydropyridin-4-yl)-1H-indole
5-(3,4-difluoro)benzoylamino-3-(1-butyl-1,2,3,6-tetrahydropyridin-4-yl)-1H-indole
5-(3-chloro-4-bromo)benzoylamino-3-(1-(3-pentyl)-1,2,3,6-tetrahydropyridin-4-yl)-1H-indole
5-(2-bromo-4-fluoro)benzoylamino-3-(1-methyl-1,2,3,6-tetrahydropyridin-4-yl)-1H-indole
5-(2,4-diiodo)benzoylamino-3-(1-(sec-butyl)-1,2,3,6-tetrahydropyridin-4-yl)-1H-indole
5-(2-chloro-5-iodo)benzoylamino-3-(1-hexyl-1,2,3,6-tetrahydropyridin-4-yl)-1H-indole
5-(2-fluoro-6-iodo)benzoylamino-3-(1-(tert-butyl)-1,2,3,6-tetrahydropyridin-4-yl)-1H-indole
5-(3-fluoro-5-chloro)benzoylamino-3-(1-(2-pentyl)-1,2,3,6-tetrahydropyridin-4-yl)-1H-indole
5-(2-thienoyl)amino-3-(1-ethyl-1,2,3,6-tetrahydropyridin-4-yl)-1H-indole
5-(2-thienoyl)amino-3-1-propyl-1,2,3,6-tetrahydropyridin-4-yl)-1H-indole
5-(2-thienoyl)amino-3-(1-isopropyl-1,2,3,6-tetrahydropyridin-4-yl)-1H-indole
5-(2-thienoyl)amino-3-(1-butyl-1,2,3,6-tetrahydropyridin-4-yl)-1H-indole
5-(2-thienoyl)amino-3-(1-isobutyl-1,2,3,6-tetrahydropyridin-4-yl)-1H-indole
5-(2-thienoyl)amino-3-(1-(sec-butyl)-1,2,3,6-tetrahydropyridin-4-yl)-1H-indole
5-(2-thienoyl)amino-3-(1-(tert-butyl)-1,2,3,6-tetrahydropyridin-4-yl)-1H-indole
5-(2-thienoyl)amino-3-(1-pentyl-1,2,3,6-tetrahydropyridin-4-yl)-1H-indole
5-(2-thienoyl)amino-3-(1-(2-pentyl)-1,2,3,6-tetrahydropyridin-4-yl)-1H-indole
5-(2-thienoyl)amino-3-(1-(3-pentyl)-1,2,3,6-tetrahydropyridin-4-yl)-1H-indole
5-(2-thienoyl)amino-3-(1-neopentyl-1,2,3,6-tetrahydropyridin-4-yl)-1H-indole
5-(2-thienoyl)amino-3-(1-hexyl-1,2,3,6-tetrahydropyridin-4-yl)-1H-indole 5-(3-thienoyl)amino-3-(1-ethyl-1,2,3,6-tetrahydropyridin-4-yl)-1H-indole
5-(3-thienoyl)amino-3-(1-propyl-1,2,3,6-tetrahydropyridin-4-yl)-1H-indole
5-(3-thienoyl)amino-3-(1-isopropyl-1,2,3,6-tetrahydropyridin-4-yl)-1H-indole
5-(3-thienoyl)amino-3-(1-butyl-1,2,3,6-tetrahydropyridin-4-yl)-1H-indole
5-(3-thienoyl)amino-3-(1-isobutyl-1,2,3,6-tetrahydropyridin-4-yl)-1H-indole
5-(3-thienoyl)amino-3-(1-(sec-butyl)-1,2,3,6-tetrahydropyridin-4-yl)-1H-indole
5-(3-thienoyl)amino-3-(1-(tert-butyl)-1,2,3,6-tetrahydropyridin-4-yl)-1H-indole
5-(3-thienoyl)amino-3-(1-pentyl-1,2,3,6-tetrahydropyridin-4-yl)-1H-indole
5-(3-thienoyl)amino-3-(1-(2-pentyl)-1,2,3,6-tetrahydropyridin-4-yl)-1H-indole
5-(3-thienoyl)amino-3-(1-(3-pentyl)-1,2,3,6-tetrahydropyridin-4-yl)-1H-indole
5-(3-thienoyl)amino-3-(1-neopentyl-1,2,3,6-tetrahydropyridin-4-yl)-1H-indole
5-(3-thienoyl)amino-3-(1-hexyl-1,2,3,6-tetrahydropyridin-4-yl)-1H-indole
5-(2-furoyl)amino-3-(1-ethyl-1,2,3,6-tetrahydropyridin-4-yl)-1H-indole
5-(2-furoyl)amino-3-(1-propyl-1,2,3,6-tetrahydropyridin-4-yl)-1H-indole
5-(2-furoyl)amino-3-(1-isopropyl-1,2,3,6-tetrahydropyridin-4-yl)-1H-indole
5-(2-furoyl)amino-3-(1-butyl-1,2,3,6-tetrahydropyridin-4-yl)-1H-indole
5-(2-furoyl)amino-3-(1-isobutyl-1,2,3,6-tetrahydropyridin-4-yl)-1H-indole
5-(2-furoyl)amino-3-(1-(sec-butyl)-1,2,3,6-tetrahydropyridin-4-yl)-1H-indole
5-(2-furoyl)amino-3-(1-(tert-butyl)piperidin-4-yl)-1H-indole
5-(2-furoyl)amino-3-(1-pentyl-1,2,3,6-tetrahydropyridin-4-yl)-1H-indole
5-(2-furoyl)amino-3-(1-(2-pentyl)-1,2,3,6-tetrahydropyridin-4-yl)-1H-indole
5-2-furoyl)amino-3-(1-(3-pentyl)-1,2,3,6-tetrahydropyridin-4-yl)-1H-indole
5-2-furoyl)amino-3-(1-neopentyl-1,2,3,6-tetrahydropyridin-4-yl)-1H-indole
5-2-furoyl)amino-3-(1-hexyl-1,2,3,6-tetrahydropyridin-4-yl)-1H-indole
5-3-furoyl)amino-3-(1-ethyl-1,2,3,6-tetrahydropyridin-4-yl)-1H-indole
5-3-furoyl)amino-3-(1-propyl-1,2,3,6-tetrahydropyridin-4-yl)-1H-indole
5-3-furoyl)amino-3-(1-isopropyl-1,2,3,6-tetrahydropyridin-4-yl)-1H-indole
5-(3-furoyl)amino-3-(1-butyl-1,2,3,6-tetrahydropyridin-4-yl)-1H-indole
5-(3-furoyl)amino-3-(1-isobutyl-1,2,3,6-tetrahydropyridin-4-yl)-1H-indole
5-(3-furoyl)amino-3-(1-(sec-butyl)-1,2,3,6-tetrahydropyridin-4-yl)-1H-indole
5-(3-furoyl)amino-3-(1-(tert-butyl)-1,2,3,6-tetrahydropyridin-4-yl)-1H-indole
5-(3-furoyl)amino-3-(1-pentyl-1,2,3,6-tetrahydropyridin-4-yl)-1H-indole
5-(3-furoyl)amino-3-(1-(2-pentyl)-1,2,3,6-tetrahydropyridin-4-yl)-1H-indole naphthalene-2-sulfonate
5-(3-furoyl)amino-3-(1-(3-pentyl)-1,2,3,6-tetrahydropyridin-4-yl)-1H-indole
5-(3-furoyl)amino-3-(1-neopentyl-1,2,3,6-tetrahydropyridin-4-yl)-1H-indole
5-(3-furoyl)amino-3-(1-hexyl-1,2,3,6-tetrahydropyridin-4-yl)-1H-indole
5-(propanoyl)amino-3-(1-neopentylpiperidin-4-yl)-1H-indole mandalate
5-(2-methylpropanoyl)amino-3-(1-(3-pentyl)piperidin-4-yl)-1H-indole
5-(2-methyl-4-butyn-1oyl)amino-3-(1-(tert-butyl)piperidin-4-yl)-1H-indole
5-(2-methylbutanoyl)-N-methylamino-3-(1-ethylpiperidin-4-yl)-1H-indole
5-(hex-3-enoyl)amino-3-(1-propylpiperidin-4-yl)-1H-indole
5-(cyclohexaneacetyl)amino-3-(1-isopropylpiperidin-4-yl)-1H-indole
5-(cycloheptylcarbonyl)amino-3-(1-butylpiperidin-4-yl)-1H-indole
5-(4-phenylbutanoyl)amino-3-(1-isopropylpiperidin-4-yl)-1H-indole
5-(5-phenylpentanoyl)amino-3-(1-(2-pentyl)piperidin-4-yl)-1H-indole
5-(3-phenoxypropanoyl)amino-3-(1-neopentylpiperidin-4-yl)-1H-indole
5-(5-phenoxypentanoyl)amino-3-(1-neopentylpiperidin-4-yl)-1H-indole
5-(3-propoxypropanoyl)amino-3-(1-isopropylpiperidin-4-yl)-1H-indole
5-(5-methoxypentanoyl)amino-3-(1-isopropylpiperidin-4-yl)-1H-indole
5-((3-propoxycarbonyl)propanoyl)amino-3-(1-isobutylpiperidin-4-yl)-1H-indole
5-((5-methoxycarbonyl)pentanoyl)amino-3-(1-isopropylpiperidin-4-yl)-1H-indole
5-(benzoyl-N-ethyl)amino-3-(1-ethylpiperidin-4-yl)-1H-indole
5-benzoylamino-3-(1-propylpiperidin-4-yl)-1H-indole
5-benzoylamino-3-(1-isopropylpiperidin-4-yl)-1H-indole
5-benzoylamino-3-(1-butylpiperidin-4-yl)-1H-indole
5-benzoylamino-3-(piperidin-4-yl)-1H-indole
5-benzoylamino-3-(1-isobutylpiperidin-4-yl)-1H-indole
5-benzoylamino-3-(1-(sec-butyl)piperidin-4-yl)-1H-indole
5-benzoylamino-3-(1-(tert-butyl)piperidin-4-yl)-1H-indole hydrochloride
5-benzoyl-N-propylamino-3-(1-pentylpiperidin-4-yl)-1H-indole
5-benzoylamino-3-(1-(2-pentyl)piperidin-4-yl)-1H-indole
5-benzoylamino-3-(1-(3-pentyl)piperidin-4-yl)-1H-indole
5-benzoylamino-3-(1-neopentylpiperidin-4-yl)-1H-indole
5-benzoylamino-3-(1-hexylpiperidin-4-yl)-1H-indole
5-(4-fluorobenzoyl)amino-3-(1-ethylpiperidin-4-yl)-1H-indole
5-(4-fluorobenzoyl)amino-3-(1-propylpiperidin-4-yl)-1H-indole
5-(4-fluorobenzoyl)amino-3-(1-isopropylpiperidin-4-yl)-1H-indole
5-(4-fluorobenzoyl)amino-3-(1-butylpiperidin-4-yl)-1H-indole
5-(4-fluorobenzoyl)amino-3-(1-isobutylpiperidin-4-yl)-1H-indole
5-(4-fluorobenzoyl)amino-3-(1-(sec-butyl)piperidin-4-yl)-1H-indole
5-(4-fluorobenzoyl)amino-3-(1-(tert-butyl)piperidin-4-yl)-1H-indole
5-(4-fluorobenzoyl)amino-3-(1-pentylpiperidin-4-yl)-1H-indole 5-(4-fluorobenzoyl)amino-3-(1-(2-pentyl)piperidin-4-yl)-1H-indole
5-(4-fluorobenzoyl)amino-3-(1-(3-pentyl)piperidin-4-yl)-1H-indole
5-(4-fluorobenzoyl)amino-3-(1-neopentylpiperidin-4-yl)-1H-indole fumarate
5-(4-fluorobenzoyl)amino-3-(1-hexylpiperidin-4-yl)-1H-indole
5-(2-chlorobenzoyl)amino-3-(1-ethylpiperidin-4-yl)-1H-indole
5-(2-chlorobenzoyl)amino-3-(1-propylpiperidin-4-yl)-1H-indole
5-(2-chlorobenzoyl)amino-3-(1-isopropylpiperidin-4-yl)-1H-indole
5-(2-chlorobenzoyl)amino-3-(1-butylpiperidin-4-yl)-1H-indole
5-(2-chlorobenzoyl)amino-3-(1-isobutylpiperidin-4-yl)-1H-indole
5-(2-chlorobenzoyl)amino-3-(1-(sec-butyl)piperidin-4-yl)-1H-indole
5-(2-chlorobenzoyl)amino-3-(1-(tert-butyl)piperidin-4-yl)-1H-indole
5-(2-chlorobenzoyl)amino-3-(1-pentylpiperidin-4-yl)-1H-indole
5-(2-chlorobenzoyl)amino-3-(1-(2-pentyl)piperidin-4-yl)-1H-indole
5-(2-chlorobenzoyl)amino-3-(1-(3-pentyl)piperidin-4-yl)-1H-indole
5-(2-chlorobenzoyl)amino-3-(1-neopentylpiperidin-4-yl)-1H-indole
5-(2-chlorobenzoyl)amino-3-(1-hexylpiperidin-4-yl)-1H-indole
5-(2-bromobenzoyl)amino-3-(1-butylpiperidin-4-yl)-1H-indole
5-(4-ethylbenzoyl)amino-3-(1-ethylpiperidin-4-yl)-1H-indole
5-(2-ethylbenzoyl)amino-3-(1-isobutylpiperidin-4-yl)-1H-indole
5-(3-propylbenzoyl)amino-3-(1-(2-pentyl)piperidin-4-yl)-1H-indole
5-(4-butylbenzoyl)amino-3-(1-methylpiperidin-4-yl)-1H-indole
5-(2-butylbenzoyl)amino-3-(1-butylpiperidin-4-yl)-1H-indole
5-(3-ethoxybenzoyl)amino-3-(1-pentylpiperidin-4-yl)-1H-indole
5-(2-propoxybenzoyl)amino-3-(1-(tert-butyl)piperidin-4-yl)-1H-indole
5-(3-butoxybenzoyl)amino-3-(1-isopropylpiperidin-4-yl)-1H-indole
5-(4-pentyloxybenzoyl)amino-3-(1-methylpiperidin-4-yl)-1H-indole
5-(2-pentyloxybenzoyl)amino-3-(1-butylpiperidin-4-yl)-1H-indole
5-(2-hexyloxybenzoyl)amino-3-(1-pentylpiperidin-4-yl)-1H-indole
5-(4-hexyloxybenzoyl)amino-3-(1-(3-pentyl)piperidin-4-yl)-1H-indole
5-(2-methylthiobenzoyl)amino-3-(1-isobutylpiperidin-4-yl)-1H-indole
5-(2-ethylthiobenzoyl)amino-3-(1-ethylpiperidin-4-yl)-1H-indole
5-(3-propylthiobenzoyl)amino-3-(1-propylpiperidin-4-yl)-1H-indole
5-(3-nitrobenzoyl)amino-3-(1-isobutylpiperidin-4-yl)-1H-indole
5-(3-cyanobenzoyl)amino-3-(1-(2-pentyl)piperidin-4-yl)-1H-indole
5-(4-(dimethylamino)benzoyl)amino-3-(1-isobutylpiperidin-4-yl)-1H-indole
5-(2-(diethylamino)benzoyl)-N-propylamino-3-(1-butylpiperidin-4-yl)-1H-indole
5-(4-(diethylamino)benzoyl)amino-3-(1-pentylpiperidin-4-yl)-1H-indole
5-(3-(dibutylamino)benzoyl)amino-3-(1-methylpiperidin-4-yl)-1H-indole
5-(4-trifluoromethoxybenzoyl)amino-3-(1-isopropylpiperidin-4-yl)-1H-indole
5-(4-(formyl)benzoyl)amino-3-(1-(sec-butyl)piperidin-4-yl)-1H-indole
5-(2-(formyl)benzoyl)amino-3-(1-neopentylpiperidin-4-yl)-1H-indole
5-(2-(acetyl)benzoyl)amino-3-(1-(3-pentyl)piperidin-4-yl)-1H-indole
5-(3-(propanoyl)benzoyl)amino-3-(1-pentylpiperidin-4-yl)-1H-indole
5-(3-(butanoyl)benzoyl)amino-3-(1-methylpiperidin-4-yl)-1H-indole
5-(2-(butanoyl)benzoyl)amino-3-(1-neopentylpiperidin-4-yl)-1H-indole
5-(2-(benzoyl)benzoyl)amino-3-(1-pentylpiperidin-4-yl)-1H-indole
5-(2-(methanesulfonyl)benzoyl)amino-3-(1-butylpiperidin-4-yl)-1H-indole
5-(3-(propanesulfonyl)benzoyl)amino-3-(1-methylpiperidin-4-yl)-1H-indole
5-(2-butanesulfonylbenzoyl)amino-3-(1-isopropylpiperidin-4-yl)-1H-indole
5-(3-phenylbenzoyl)amino-3-(1-(tert-butyl)piperidin-4-yl)-1H-indole
5-(2,3-dibromo)benzoyl-N-isopropylamino-3-(1-isopropylpiperidin-4-yl)-1H-indole
5-(2-bromo-3-iodo)benzoylamino-3-(1-(2-pentyl)piperidin-4-yl)-1H-indole
5-(3,4-difluoro)benzoylamino-3-(1-butylpiperidin-4-yl)-1H-indole
5-(3-chloro-4-bromo)benzoylamino-3-(1-(3-pentyl)piperidin-4-yl)-1H-indole
5-(2-bromo-4-fluoro)benzoylamino-(3-(1-methylpiperidin-4-yl)-1H-indole
5-(2,4-diiodo)benzoylamino-(3-(1-(sec-butyl)piperidin-4-yl)-1H-indole
5-(2-chloro-5-iodo)benzoylamino-(3-(1-hexylpiperidin-4-yl)-1H-indole
5-(2-fluoro-6-iodo)benzoylamino-(3-(1-(tert-butyl)piperidin-4-yl)-1H-indole
5-(3-fluoro-5-chloro)benzoylamino-3-(1-(2-pentyl)piperidin-4-yl)-1H-indole
5-(2-thienoyl)-N-butylamino-3-(1-ethylpiperidin-4-yl)-1H-indole
5-(2-thienoyl)amino-3-(1-propylpiperidin-4-yl)-1H-indole
5-(2-thienoyl)amino-3-(1-isopropylpiperidin-4-yl)-1H-indole
5-(2-thienoyl)amino-3-(1-butylpiperidin-4-yl)-1H-indole
5-(2-thienoyl)amino-3-(1-isobutylpiperidin-4-yl)-1H-indole
5-(2-thienoyl)amino-3-(1-(sec-butyl)piperidin-4-yl)-1H-indole
5-(2-thienoyl)amino-3-(1-(tert-butyl)piperidin-4-yl)-1H-indole
5-(2-thienoyl)amino-3-(1-pentylpiperidin-4-yl)-1H-indole
5-(2-thienoyl)amino-3-(1-(2-pentyl)piperidin-4-yl)-1H-indole
5-(2-thienoyl)amino-3-(1-(3-pentyl)piperidin-4-yl)-1H-indole
5-(2-thienoyl)amino-3-(1-neopentylpiperidin-4-yl)-1H-indole 5-(2-thienoyl)amino-3-(1-hexylpiperidin-4-yl)-1H-indole
5-(3-thienoyl)amino-3-(1-ethylpiperidin-4-yl)-1H-indole
5-(3-thienoyl)amino-3-(1-propylpiperidin-4-yl)-1H-indole
5-(3-thienoyl)amino-3-(1-isopropylpiperidin-4-yl)-1H-indole
5-(3-thienoyl)amino-3-(1-butylpiperidin-4-yl)-1H-indole
5-(3-thienoyl)amino-3-(1-isobutylpiperidin-4-yl)-1H-indole
5-(3-thienoyl)amino-3-(1-(sec-butyl)piperidin-4-yl)-1H-indole
5-(3-thienoyl)amino-3-(1-(tert-butyl)piperidin-4-yl)-1H-indole
5-(3-thienoyl)amino-3-(1-pentylpiperidin-4-yl)-1H-indole
5-(3-thienoyl)amino-3-(1-(2-pentyl)piperidin-4-yl)-1H-indole
5-(3-thienoyl)amino-3-(1-(3-pentyl)piperidin-4-yl)-1H-indole
5-(3-thienoyl)amino-3-(1-neopentylpiperidin-4-yl)-1H-indole
5-(3-thienoyl)amino-3-(1-hexylpiperidin-4-yl)-1H-indole
5-(2-furoyl)amino-3-(1-ethylpiperidin-4-yl)-1H-indole
5-(2-furoyl)amino-3-(1-propylpiperidin-4-yl)-1H-indole
5-(2-furoyl)amino-3-(1-isopropylpiperidin-4-yl)-1H-indole
5-(2-furoyl)amino-3-(1-butylpiperidin-4-yl)-1H-indole
5-(2-furoyl)amino-3-(1-isobutylpiperidin-4-yl)-1H-indole
5-(2-furoyl)amino-3-(1-(sec-butyl)piperidin-4-yl)-1H-indole
5-(2-furoyl)amino-3-(1-(tert-butyl)piperidin-4-yl)-1H-indole
5-(2-furoyl)amino-3-(1-pentylpiperidin-4-yl)-1H-indole
5-(2-furoyl)amino-3-(1-(2-pentyl)piperidin-4-yl)-1H-indole
5-(2-furoyl)amino-3-(1-(3-pentyl)piperidin-4-yl)-1H-indole
5-(2-furoyl)amino-3-(1-neopentylpiperidin-4-yl)-1H-indole
5-(2-furoyl)amino-3-(1-hexylpiperidin-4-yl)-1H-indole
5-(3-furoyl)amino-3-(1-ethylpiperidin-4-yl)-1H-indole
5-(3-furoyl)amino-3-(1-propylpiperidin-4-yl)-1H-indole
5-(3-furoyl)amino-3-(1-isopropylpiperidin-4-yl)-1H-indole
5-(3-furoyl)amino-3-(1-butylpiperidin-4-yl)-1H-indole
5-(3-furoyl)amino-3-(1-isobutylpiperidin-4-yl)-1H-indole
5-(3-furoyl)amino-3-(1-(sec-butyl)piperidin-4-yl)-1H-indole
5-(3-furoyl)amino-3-(1-(tert-butyl piperidin-4-yl)-1H-indole
5-(3-furoyl)amino-3-(1-pentylpiperidin-4-yl)-1H-indole
5-(3-furoyl)amino-3-(1-(2-pentyl)piperidin-4-yl)-1H-indole
5-(3-furoyl)amino-3-(1-(3-pentyl)piperidin-4-yl)-1H-indole
5-(3-furoyl)amino-3-(1-neopentylpiperidin-4-yl)-1H-indole
5-(3-furoyl)amino-3-(1-hexylpiperidin-4-yl)-1H-indole
N-[pyridin-2-yl]-5-carboxamido-3-(1-methyl-1,2,5,6-tetrahydropyridin-4-yl)-1H-indole
N-[fur-3-yl]-5-carboxamido-3-(1-methyl-1,2,5,6-tetrahydropyridin-4-yl)-1H-indole
N-[pyrazol-3-yl]-5-carboxamido-3-(1-methyl-1,2,5,6-tetrahydropyridin-4-yl)-1H-indole
N-[thiazol-2-yl]-5-carboxamido-3-(1-methyl-1,2,5,6-tetrahydropyridin-4-yl)-1H-indole
N-[quinolin-4-yl]-5-carboxamido-3-(1-methyl-1,2,5,6-tetrahydropyridin-4-yl)-1H-indole
N-[imidazol-4-yl]-5-carboxamido-3-(1-methylpiperidin-4-yl)-1H-indole
N-[fur-3-yl]-5-carboxamido-3-1-methyl-1,2,5,6-tetrahydropyridin-4-yl)-1H-indole
N-[pyrimidin-5-yl]-5-carboxamido-3-(1-methylpiperidin-4-yl)-1H-indole
N-[indol-2-yl]-5-carboxamido-3-(1-methylpiperidin-4-yl)-1H-indole
N-[isoxazol-5-yl]-5-carboxamido-3-(1-methylpiperidin-4-yl)-1H-indole The compounds of this invention are prepared by methods well known to one of ordinary skill in the art, such as that generally described in U.S. Pat. No. 4,443,451, hereby incorporated by reference. While the simple indoles required for the preparation of the compounds of this invention are generally commercially available, their preparations are described in Robinson, *The Fischer Indole Synthesis*, Wiley, New York (1983); Hamel, et al., *Journal of Organic Chemistry*, 59, 6372 (1994); and Russell, et al., *Organic Preparations and Procedures International*, 17, 391 (1985).

The compounds of the invention where X is —NR$^7$SO$_2$R$^8$ may be prepared by first modifying an appropriate 5-aminoindole. When R$^7$ is hydrogen, the 5-aminoindole is reacted with an appropriate sulfonyl halide or anhydride to give the corresponding sulfonamide. When R$^7$ is lower alkyl, however, the 5-aminoindole is first acylated, and then reduced with an appropriate hydride reducing agent. Alternatively, the 5-aminoindole may be reductively alkylated with an appropriate aldehyde or ketone in the presence of a suitable hydride reducing agent to give the appropriately substituted indole. These substituted indoles are then reacted with a sulfonyl halide or anhydride to give the corresponding sulfonamide. This chemistry is illustrated in Synthetic Scheme I, where M is methoxy, ethoxy, methyl, ethyl, propyl, or isopropyl, LG is chloro or bromo, and R$^1$, R$^7$, and R$^8$ are as defined supra.

Synthetic Scheme I

R$^7$ = H

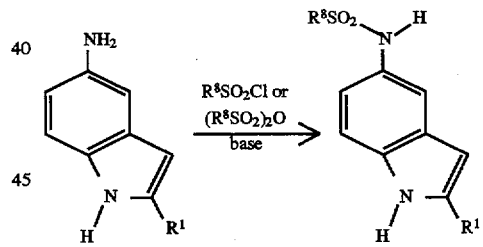

R$^7$ = lower alkyl

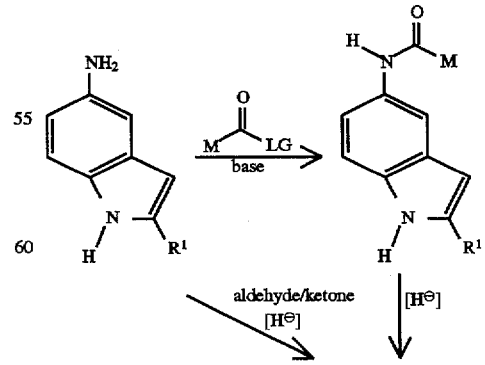

-continued
Synthetic Scheme I

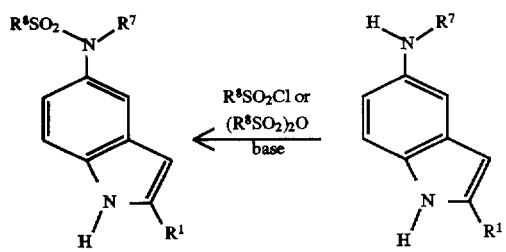

When $R^7$ is to be hydrogen, a solution of 5-aminoindole in a suitable solvent, such as tetrahydrofuran, dioxane, diethyl ether or dimethylformamide, at a temperature from about ambient to about 0° C., is reacted with a commercially available $R^8$-sulfonyl halide or $R^8$-sulfonic anhydride in the presence of a suitable base such as pyridine or triethylamine. The resultant sulfonamide may be isolated by dilution of the reaction mixture with water, adjustment of pH, and extraction with a water immiscible solvent such as dichloromethane. The product may be used for further reaction as recovered, or may be purified by chromatography, or by recrystallization from a suitable solvent.

When $R^7$ is to be lower alkyl, a solution of 5-aminoindole in a suitable solvent, such as tetrahydrofuran, dioxane, or diethyl ether, at a temperature from about ambient to about 0° C., is reacted with a compound of structure M—C(O)-halo in the presence of a suitable base such as pyridine or triethylamine. The resultant compound is isolated by dilution of the reaction mixture with water and extraction with a water immiscible solvent such as dichloromethane. This acylated product may either be purified chromatographically or used directly in the subsequent step. The acylated product is then dissolved in a suitable solvent, such as tetrahydrofuran or diethyl ether, at a temperature from about ambient to about 0° C., and is treated with a suitable hydride reducing agent such as diborane or lithium aluminum hydride. The reaction is stirred from 1 to 24 hours and is then treated with aqueous solution of sodium sulfate. The resultant suspension is filtered, and the filtrate concentrated under reduced pressure. The product may be used for further reaction as is, purified by chromatography, or recrystallized from a suitable solvent.

Alternatively, a solution of a 5-aminoindole in a solvent suitable for the azeotropic removal of water, such as toluene, benzene or cyclohexane, is reacted at reflux with an appropriate aldehyde or ketone, such as formaldehyde, acetaldehyde, propanal, butanal or acetone, in the presence of 0.1-10% of a proton source such as p-toluenesulfonic acid. When the reaction is complete the volatiles are removed under reduced pressure and the residue redissolved in an alkanol such as methanol or ethanol. This solution is then subjected to hydrogenation conditions, or is treated with an appropriate hydride reducing agent, such as sodium borohydride or, preferably, sodium cyanoborohydride in the presence of an anhydrous acid such as hydrogen chloride. The reaction is then diluted with water, treated with base and extracted into a water immiscible solvent such as dichloromethane. The product may be used as is for further reaction, purified by chromatography or crystallized from a suitable solvent. This product is now treated with a commercially available $R^8$-sulfonyl halide or $R^8$-sulfonic anhydride as described supra to give the required sulfonamides.

Compounds of the invention where X is —S—$R^2$, —C(O)$R^3$ or —C(O)NR$^4$R$^{15}$ are prepared by first converting a 5-bromoindole into a 5-bromo-3-(1,2,3,6-tetrahydropyridin-4-yl)-1H-indole or 5-bromo-3-(1-piperidin-4-yl)-1H-indole. Compounds of the invention where X is —NR$^5$R$^6$, —NHC(Q)NR$^{10}$R$^{11}$, —NHC(O)OR$^{12}$ or —NR$^{13}$C(O)R$^{14}$ are prepared by first converting a 5-nitro-or 5-aminoindole into a 5-nitro-or 5-amino-3-(1,2,3,6-tetrahydropyridin-4-yl)-1H-indole or into the corresponding 5-nitro-or 5-amino-(1-piperidin-4-yl)-1H-indole. Compounds of the invention where X is —NR$^7$SO$_2$$^{R8}$ or —NR$^{13}$C(O)R$^{14}$ may be prepared by converting the appropriately substituted indole into the corresponding 3-(1,2,3,6-tetrahydropyridin-4-yl)-1H-indole or 3-(1-piperidin-4-yl)-1H-indole. This chemistry is illustrated in Synthetic Scheme II, where Y is nitro, amino, bromo, —NR$^{13}$C(O)R$^{14}$, or —NR$^7$SO$_2$R$^8$, and R, R$^1$, R$^7$, R$^8$, R$^{13}$ and R$^{14}$ are as defined supra.

Synthetic Scheme II

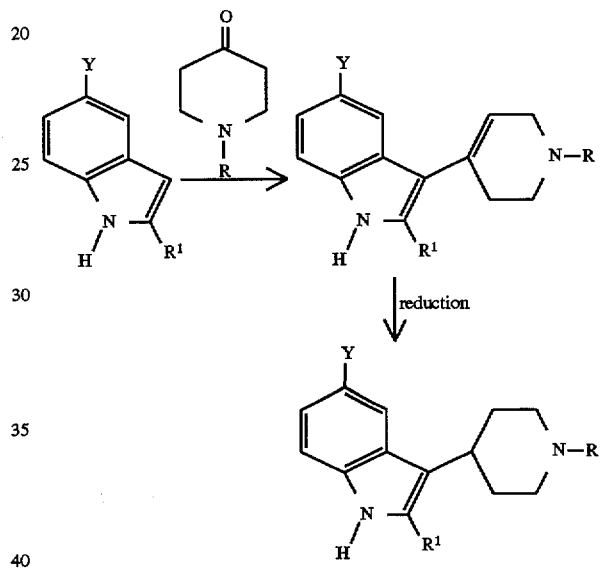

The 5-substituted indole is condensed with a 4-piperidone in the presence of a suitable base to give the corresponding 5-substituted-3-(1,2,3,6-tetrahydropyridin-4-yl)-1H-indole. The reaction is performed by first dissolving an excess of the base, typically sodium or potassium hydroxide, in a lower alkanol, typically methanol or ethanol. The indole and two equivalents of the 4-piperidone are then added and the reaction refluxed for 8–72 hours. The resulting 5-substituted-3-(1,2,3,6tetrahydro-pyridin-4-yl)-1H-indoles may be isolated from the reaction mixture by the addition of water. Compounds which precipitate may be isolated directly by filtration while others may be extracted by adjusting the pH of the solution and extracting with a water immiscible solvent such as ethyl acetate or dichloromethane. The compounds recovered may be used directly in subsequent steps or first purified by silica gel chromatography or recrystallization from a suitable solvent.

The 5-substituted-3-(1-substituted-1,2,3,6-tetrahydropyridin-4-yl)-1H-indoles may be used to prepare other compounds of the invention or, if desired, may be hydrogenated over a precious metal catalyst, such as palladium on carbon, to give the corresponding 5-substituted-3-(piperidin-4-yl)-1H-indoles. When Y is bromo, a hydrogenation catalyst such as sulfided platinum on carbon, platinum oxide, or a mixed catalyst system of sulfided platinum on carbon with platinum oxide is used to prevent hydrogenolysis of the 5-bromo substituent during reduction of the tetrahydro-pyridinyl double bond. The hydrogenation solvent may consist of a lower alkanol, such as methanol or ethanol, tetrahydrofuran, or a mixed solvent system of tetrahydrofuran and ethyl acetate. The hydrogenation may be performed at an initial hydrogen pressure of 20–80 p.s.i., preferably from 50–60 p.s.i., at 0°–60° C., preferably at ambient temperature to 40° C., for 1 hour to 3 days. Additional charges of hydrogen may be required to drive the reaction to completion depending on the specific substrate. The 5-substituted-3-(piperidin-4-yl)-1H-indoles prepared in this manner are isolated by removal of the catalyst by filtration followed by concentration of the reaction solvent under reduced pressure. The product recovered may be used directly in a subsequent step or further purified by chromatography, or by recrystallization from a suitable solvent.

As an alternative to hydrogenation, the 5-substituted-3-(1,2,3,6-tetrahydro-4-pyridinyl)-1H-indoles may be converted to the corresponding 5-substituted-3-(piperidin-4-yl)-1H-indoles by treatment with trifluoroacetic acid/triethylsilane if desired. The 5-substituted-3-(1-substituted-1,2,5,6-tetrahydro-4-pyridinyl)-1H-indole is dissolved in trifluoroacetic acid to which is added an excess, 1.1–10.0 equivalents, of triethylsilane. The reaction mixture is stirred at about ambient temperature for from about 1 to about 48 hours at which time the reaction mixture is concentrated under reduced pressure. The residue is then treated with 2N sodium or potassium hydroxide and the mixture extracted with a water immiscible solvent such as dichloromethane or diethyl ether. The resultant 5-substituted-3-(piperidin-4-yl)-1H-indole is purified by column chromatography if desired.

The skilled artisan will appreciate that the 5-nitro substituent may be reduced before or after condensation with an appropriate 4-piperidone. Additionally, the nitro group and the 1,2,3,6-tetrahydropyridinyl double bond may be hydrogenated simultaneously if desired.

The compounds of the invention where X is —S—R² are prepared from the corresponding 5-bromo-3-(1,2,3,6-tetrahydropyridin-4-yl)-1H-indoles or 5-bromo-3-(piperidin-4-yl)-1H-indoles as illustrated in Synthetic Scheme III, where A, B, R¹ and R² are as defined supra and R=C₁–C₄ alkyl.

Synthetic Scheme III

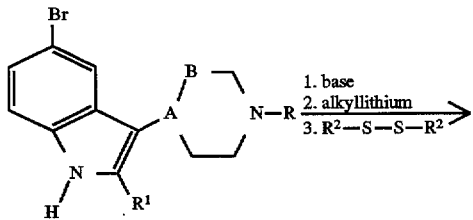

-continued
Synthetic Scheme III

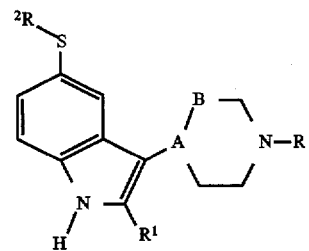

The 5-bromo-3-(1,2,3,6-tetrahydropyridin-4-yl)-1H-indoles or 5-bromo-3-(piperidin-4-yl)-1H-indoles in a suitable aprotic solvent, such as diethyl ether or tetrahydrofuran, are cooled to about 0° C. and treated with potassium hydride to deprotonate the indole nucleus at the 1-position. While other hydrides are useful for this deprotonation, the resultant potassium salt is more soluble in typical reaction solvents. The reaction mixture is then cooled to about –78° C. and halogen-metal exchange effected by the addition of two equivalents of t-butyllithium. To this dianion solution are then added an appropriate disulfide and the reaction mixture allowed to warm to ambient temperature. The compound of the invention is isolated by treating the reaction mixture with aqueous base, such as sodium or potassium hydroxide, and then extracting with a water immisible solvent such as diethyl ether or dichloromethane. The reaction product may then be purified by column chromatography.

Compounds of the invention where X is —C(O)R³ or —C(O)NR⁴R¹⁵ are prepared from the corresponding 5-bromo-3-(1,2,3,6-tetrahydropyridin-4-yl)-1H-indoles or 5-bromo-3-(piperidin-4-yl)-1H-indoles as illustrated in Synthetic Scheme IV, where A, B, R¹, R³, R⁴ and R¹⁵ are as defined supra and R=C₁–C₄ alkyl.

Synthetic Scheme IV

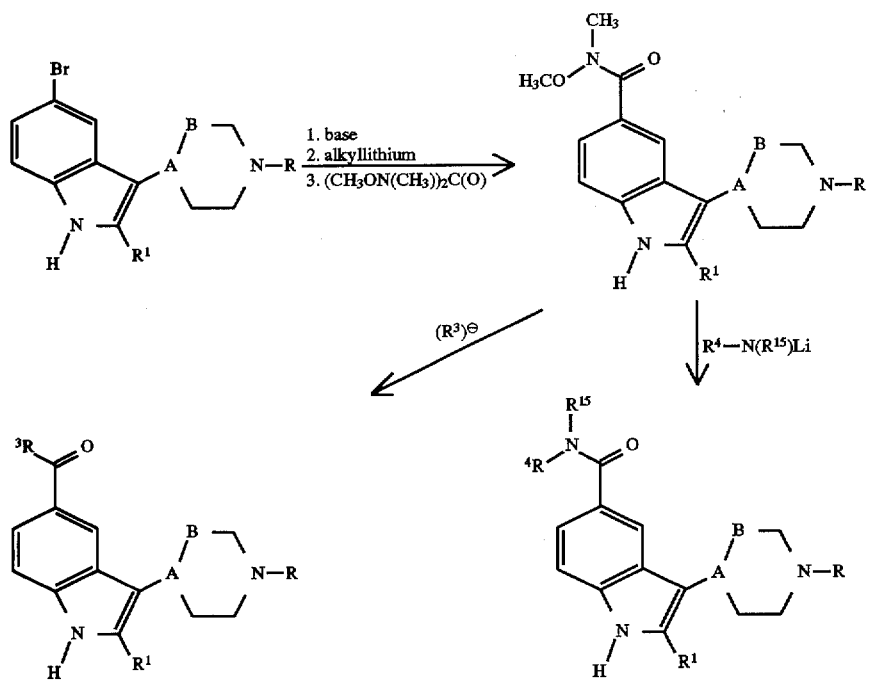

The dianion of the 5-bromo-3-(1,2,3,6-tetrahydropyridin-4-yl)-1H-indoles or 5-bromo-3-(1-substituted-piperidin-4-yl)-1H-indole, prepared as described supra, is then treated with N,N'-dimethyl-N,N'-dimethoxyurea. The resulting N-methyl-N-methoxy-5-carboxamido-1H-indole is isolated by treating the reaction mixture with aqueous base, such as sodium or potassium hydroxide, and then extracting with a water immisible solvent such as diethyl ether or dichloromethane. The reaction product may then be purified by column chromatography.

Compounds of the invention where X is —C(O)R³ are prepared by reacting a solution of the N-methyl-N-methoxy-5-carboxamido-3-(1,2,3,6-tetrahydropyridin-4-yl)-1H-indole or N-methyl-N-methoxy-5-carboxamido-3-(piperidin-4-yl)-1H-indole in a suitable solvent, such as diethyl ether or tetrahydrofuran, at about 0° C., with an appropriate reagent such as an aryl- or alkyllithium or an alkyl or aryl Grignard reagent. These reagents are either commercially available or may be prepared by methods well known to one of ordinary skill in the art. The aryl- or alkyllithium reagents are conveniently prepared by treating an appropriate aryl or alkyl halide with n-butyllithium. The aryl or alkyl Grignard reagents may be prepared by treating an appropriate aryl or alkyl halide with magnesium. The compounds of interest may be isolated by aqueous work-up followed by extraction into a water immiscible solvent such as diethyl ether or dichloromethane, and then purified by chromatography, or by recrystallization from a suitable solvent.

The skilled artisan will also appreciate that the compounds of the invention where X is —C(O)R³ are also available by the reaction of the dianion of either a 5-bromo-3-(1,2,3,6-tetrahydropyridin-4-yl)-1H-indole or a 5-bromo-3-(piperidin-4-yl)-1H-indole with an appropriate aryl or alkyl N-methyl-N-methoxycarboxamide. These carboxamides are prepared from the corresponding carboxylic acids and N-methyl-N-methoxyamine under standard peptide coupling conditions using N,N'-dicyclohexylcarbodiimide.

Compounds of the invention where X is —C(O)NR⁴R¹⁵ are prepared by reacting a solution of the N-methyl-N-methoxy-5-carboxamido-3-(1,2,3,6-tetrahydropyridin-4-yl)-1H-indole or N-methyl-N-methoxy-5-carboxamido-3-(piperidin-4-yl)-1H-indole in a suitable solvent, such as diethyl ether or tetrahydrofuran, at about 0° C., with the anion of an appropriate amine. These anions are prepared by treating the appropriate amine with n-butyllithium. The compounds of interest may be isolated by aqueous work-up followed by extraction into a water immiscible solvent such as diethyl ether or dichloromethane, and then purified by chromatography, or by recrystallization from a suitable solvent.

Alternatively, compounds of the invention where X is —C(O)NR⁴R¹⁵ are prepared by subjecting an appropriate indole 5-carboxylic acid and an appropriate amine to standard peptide coupling conditions. The indole carboxylic acid in an appropriate solvent may be treated with oxalyl chloride, thionyl chloride or phosphorous tribromide in an appropriate solvent, for example toluene, to prepare the corresponding acid halide. The acid halide in a suitable solvent, for example tetrahydrofuran or dimethylformamide, may be treated with an amine of formula HNR⁴R¹⁴ in the presence of a suitable base such as triethylamine, pyridine or dimethylaminopyridine to provide the desired compound. The product may be isolated by aqueous work-up followed by extraction into a water immiscible solvent such as diethyl ether, ethyl acetate or dichloromethane, and then purified by chromatography, or by recrystallization from a suitable solvent.

Preferably, compounds of the invention where X is —C(O)NR⁴R¹⁵ are prepared by reacting the appropriate indole 5-carboxylic acid with an appropriate amine in the presence of typical peptide coupling reagents such as N,N'-carbonyldiimidazole (CDI), N,N'-dicyclohexylcarbodiimide (DCC) and 1-(3-dimethylaminopropyl)-3-ethylcarbodiimide hydrochloride (EDC).

Compounds of the invention where X is —NR$^5$R$^6$, —NHC(Q)NR$^{10}$R$^{11}$, —NHC(O)OR$^{12}$ or —NR$^{13}$C(O)R$^{14}$ are prepared by reacting the appropriate 5-amino-3-(1,2,3,6-tetrahydropyridin-4-yl)-1H-indole or 5-amino-3-(piperidin-4-yl)-1H-indole with a suitable electrophile. These reactions are illustrated in Synthetic Scheme V, where A, B, R$^1$, R$^5$, R$^6$, R$^{10}$, R$^{11}$, R$^{12}$, R$^{13}$ and R$^{14}$ are as described supra and R=C$_1$–C$_4$ alkyl.

(piperidin-4-yl)-1H-indole in a suitable solvent, such as chloroform or dichloromethane, with an appropriate isocyanate, isothiocyanate, carbamoyl chloride or carbamoyl bromide. Appropriate carbamoyl chlorides are available by treating an amine of formula HNR$^{10}$R$^{11}$ with phosgene. When a carbamoyl chloride or carbamoyl bromide is used, the reactions are performed in the presence of a suitable base. Suitable bases include amines typically used as acid Synthetic Scheme V

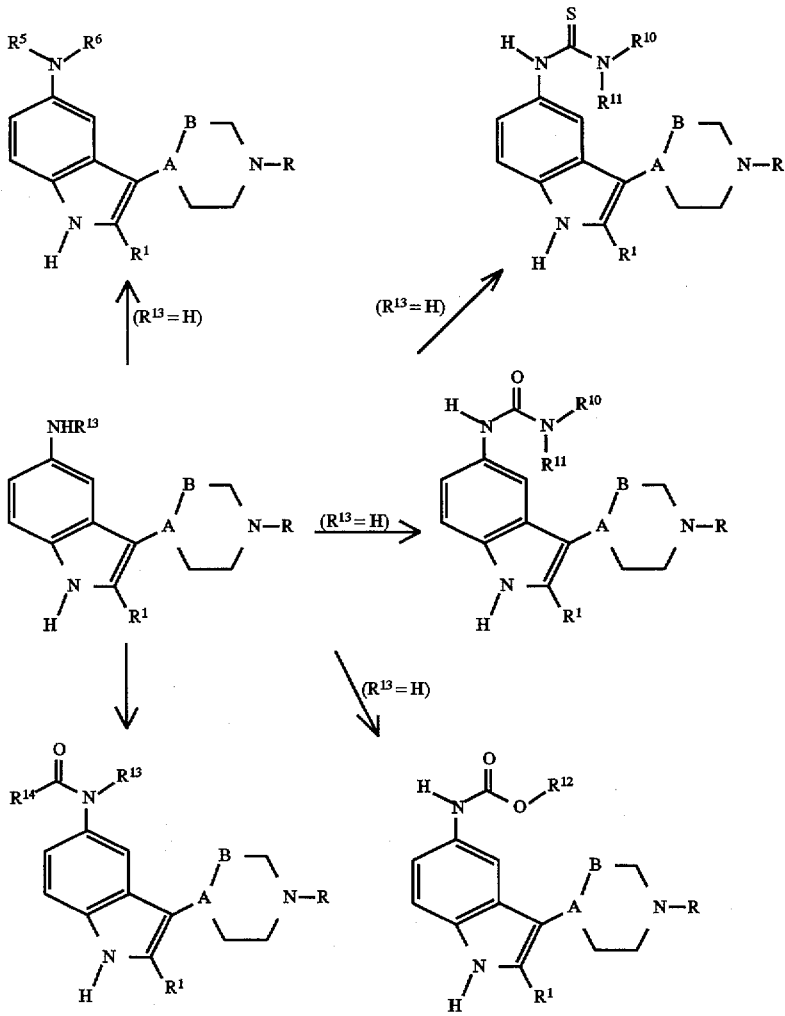

Compounds of the invention where X is —NR$^5$R$^6$ are prepared by treating a solution of the 5-amino-3-(1,2,3,6-tetrahydropyridin-4-yl)-1H-indole or 5-amino-3-(piperidin-4-yl)-1H-indole in a suitable solvent, such as dichloromethane, tetrahydrofuran, acetonitrile or dimethylformamide, with a suitable electrophile, such as trifluoromethanesulfonic anhydride or N-carbethoxyphthalimide, in the presence of a suitable base such as pyridine or triethylamine. The reaction product is isolated by evaporation of the reaction solvent under reduced pressure. The product may be purified by chromatography, or by crystallization from an appropriate solvent.

Compounds of the invention where X is —NHC(Q) NR$^{10}$R$^{11}$ are prepared by treating a solution of the 5-amino-3-(1,2,3,6-tetrahydropyridin-4-yl)-1H-indole or 5-amino-3- scavengers, such as pyridine or triethylamine, or commercially available polymer bound bases such as polyvinylpyridine. If necessary, an excess of the isocyanate, isothiocyanate, carbamoyl chloride or carbamoyl bromide is employed to ensure complete reaction of the starting amine. The reactions are performed at about ambient to about 80° C., for from about three hours to about three days. Typically, the product may be isolated by washing the reaction mixture with water and concentrating the remaining organics under reduced pressure. When an excess of isocyanate, isothiocyanate, carbamoyl chloride or carbamoyl bromide has been used, however, a polymer bound primary or secondary amine, such as an aminomethylated polystyrene, may be conveniently added to react with the excess reagent. Isolation of products from reactions where a polymer bound reagent has been used is greatly simplified, requiring only filtration of the reaction mixture and then concentration of the filtrate under reduced pressure. The product from these reactions may be purified chromatographically or recrystallized from a suitable solvent if desired. The skilled artisan will appreciate that compounds of the invention which are ureas may be converted into the corresponding thiourea by treatment with [2,4-bis(4-methoxyphenyl)-1,3-dithia-2,4-diphosphetane-2,4-disulfide] (Lawesson's Reagent) or phosphorus pentasulfide.

Compounds of the invention where X is —NHC(O)OR$^{12}$ are prepared by reacting the 5-amino-3-(1,2,3,6-tetrahydropyridin-4-yl)-1H-indole or 5-amino-3-(piperidin-4-yl)-1H-indole with an appropriately substituted chloroformate in the presence of a suitable amine under the conditions described in the previous paragraph. Likewise, compounds of the invention where X is —NR$^{13}$C(O)R$^{14}$ are prepared by reacting the 5-amino-3-(1,2,3,6-tetrahydropyridin-4-yl)-1H-indole or 5-amino-3-(piperidin-4-yl)-1H-indole with an appropriate carboxylic acid chloride, bromide or anhydride, optionally in the presence of an acylation catalyst such as dimethylaminopyridine, in the presence of a suitable base, such as those described supra.

Alternatively, compounds of the invention where X is —NR$^{13}$C(O)R$^{14}$ are prepared by reacting the 5-amino-3-(1,2,3,6-tetrahydropyridin-4-yl)-1H-indole or 5-amino-3-(piperidin-4-yl)-1H-indole with an appropriate carboxylic acid halide, carboxylic acid anhydride, or a carboxylic acid in the presence of typical peptide coupling reagents such as N,N'-carbonyldiimidazole (CDI), N,N'-dicyclohexylcarbodiimide (DCC) and 1-(3-dimethylaminopropyl)-3-ethylcarbodiimide hydrochloride (EDC). A polymer supported form of EDC has been described (*Tetrahedron Letters*, 34(48), 7685 (1993)) and is very useful for the preparation of the compounds of the present invention. The product from these reactions is isolated and purified as described above.

The skilled artisan will appreciate that the order in which the steps are performed to prepare the compounds of the present invention is not important in many cases. For example, compounds where X is —NR$^{7}$SO$_2$R$^{8}$ are accessible by subjecting the 5-amino-3-(1,2,3,6-tetrahydropyridin-4-yl)-1H-indoles or 5-amino-3-(piperidin-4-yl)-1H-indoles to the conditions illustrated in Synthetic Scheme I. Likewise, 5-aminoindole may be subjected to the reaction sequences illustrated in Synthetic Scheme V prior to reaction with a 4-piperidone as illustrated in Synthetic Scheme II. The skilled artisan will also appreciate that compounds where R is H may be prepared by condensing 4-piperidone with a suitably substituted indole to give the corresponding 3-(1,2,3,6-tetrahydropyridin-4-yl)-1H-indoles which may then be hydrogenated if desired. Alternatively, 1-benzyl-4-piperidone may be substituted at any point in the synthesis for a suitably substituted 4-piperidone. The benzyl group may then be removed by standard hydrogenation conditions after reactions for which the secondary amine would be incompatible are complete. The 3-(1,2,3,6-tetrahydropyridin-4-yl)-1H-indoles may also be reduced to the corresponding 3-(piperidin-4-yl)-1H-indoles at any convenient point in the synthetic sequence. These variations are made apparent in the following Preparations and Examples.

PREPARATION I 5-bromo-3-(1-methylpiperidin-4-yl)-1H-indole

Preparation of 5-bromo-3-(1-methyl-1,2,3,6-tetrahydropyridin-4-yl)-1H-indole

To a solution of 56.11 gm (306 mMol) potassium hydroxide in 300 mL methanol were added 38 mL (306 mMol) 1-methyl-4-piperidone followed by 30.0 gm (153 mMol) 5-bromo-1H-indole. The reaction mixture was stirred at reflux for 18 hours. The reaction mixture was then cooled to ambient and diluted with 1.5 L water. The resultant white solid was filtered, washed sequentially with water and diethyl ether, and then dried under vacuum to give 44.6 gm (100%) 5-bromo-3-(1-methyl-1,2,3,6-tetrahydro-4-pyridinyl)-1H-indole.

Catalytic hydrogenation

To a solution of 44.6 gm (153 mMol) 5-bromo-3-(1-methyl-1,2,3,6-tetrahydro-4-pyridinyl)-1H-indole in 1.95 L tetrahydrofuran were added 9.0 gm platinum oxide. The reaction mixture was hydrogenated with an initial hydrogen pressure of 60 p.s.i. at ambient temperature for 24 hours. The reaction mixture was filtered and the filtrate concentrated under reduced pressure. The residue was recrystallized from acetonitrile to give 32.6 gm (73.7%) of the title compound as a white solid.

MS(m/e): 293(M$^{+}$).

Calculated for C$_{14}$H$_{17}$N$_2$Br: Theory: C, 57.32; H, 5.96; N, 9.69. Found: C, 57.35; H, 5.84; N, 9.55.

PREPARATION II

N-methyl-N-methoxy-5-carboxamido-3-(1-methylpiperidin-4-yl)-1H-indole

To a suspension of 0.72 gm (3.58 mMol) potassium hydride in 16.0 mL tetrahydrofuran at 0° C. was added a solution of 1.0 gm (3.41 mMol) 5-bromo-3-(1-methylpiperidin-4-yl)-1H-indole in 16.0 mL tetrahydrofuran and the solution stirred for about 30 minutes. The resulting mixture was cooled to about −78° C. and to it were added 4.4 mL (7.5 mMol) t-butyl lithium, which had been precooled to −78° C., via cannula. After about 15 minutes 0.66 gm (3.41 mMol) N,N'-dimethyl-N,N'-dimethoxyurea were added and the reaction mixture was allowed to warm gradually to ambient. The reaction mixture was then treated with 5N sodium hydroxide and extracted with diethyl ether. The ether extracts were combined, washed with saturated aqueous sodium chloride, dried over sodium sulfate and concentrated under reduced pressure. Purification by flash chromatography, eluting with 4.5:0.5:0.2 ethyl acetate:methanol:toluene, gave 0.61 gm (60%) of the title compound.

MS(m/e): 301(M$^{+}$)

IR: 1632 cm$^{-1}$

Calculated for C$_{17}$H$_{23}$N$_3$O$_2$.0.25 H$_2$O: Theory: C, 66.75; H, 7.74; N, 13.73. Found: C, 66.47; H, 7.72; N, 13.69.

PREPARATION III 2-methyl-5-amino-1H-indole

To a solution of 2.0 gm (11.4 mMol) 2-methyl-5-nitro-1H-indole in 100 mL 1:1 ethanol:tetrahydrofuran were added 0.25 gm 5% palladium on carbon. The suspension was hydrogenated at ambient temperature at an initial hydrogen pressure of 60 p.s.i. After 5 hours the reaction mixture was filtered and the filtrate concentrated under reduced pressure to give 1.5 gm of a dark brown solid. The solid was purified by flash chromatography, eluting with a gradient of dichloromethane containing 0–3% methanol, to give 1.19 gm (71.7%) of the title compound as light brown plates.

m.p.=154°–156° C.

MS(m/e): 147(M+1)

Calculated for $C_9H_{10}N_2$: Theory: C, 73.94; H, 6.89; N, 19.16. Found: C, 74.15; H, 6.93; N, 19.27.

Many of the 5-($C_1$–$C_4$ alkyl)amino-1H-indoles required for the preparation of compounds of the invention are available through the procedure described in Preparation IV.

PREPARATION IV

5-methylamino-1H-indole

A. Peparation of N-ethoxycarbonyl-5-amino-1H-indole

To a solution of 4.27 gm (32.3 mMol) 5-amino-1H-indole in 50 mL tetrahydrofuran were added 5.4 mL (38.8 mMol) triethylamine and the reaction mixture was then cooled to 0° C. To this solution were then added dropwise 3.4 mL (35.5 mMol) ethyl chloroformate. After 4 hours the reaction mixture was diluted with 1N HCl and was then extracted with ethyl acetate. The organic phase was washed sequentially with 1N HCl, water and saturated aqueous sodium chloride. The remaining organics were dried over sodium sulfate and concentrated under reduced pressure to give 7.4 gm of a dark oil. This oil was purified by flash chromatography, eluting with a gradient of dichloromethane containing 0–2.5% methanol, to give 4.95 gm (75%) of the title compound as a tan solid.

m.p.=113°–114° C.

MS(m/e): 204(M$^+$)

Calculated for C11H12N2O2: Theory: C, 64.69; H, 5.92; N, 13.72. Found: C, 64.76; H, 5.92; N, 13.76.

B. Reduction of N-ethoxycarbonyl-5-amino-1H-indole

To a suspension of 6.3 gm (164.5 mMol) lithium aluminum hydride in 50 mL tetrahydrofuran was added dropwise a solution of 4.8 gm (23.5 mMol) N-ethoxycarbonyl-5-amino-1H-indole in 40 mL tetrahydrofuran. The reaction mixture was heated to reflux until the starting material was consumed as measured by thin-layer chromatography. The reaction mixture was then cooled to ambient and treated with saturated aqueous sodium sulfate to destroy excess lithium aluminum hydride. The resulting suspension was filtered and the filtrate concentrated under reduced pressure to give 3.6 gm of a dark solid. The solid was subjected to flash chromatography, eluting with a gradient of dichloromethane containing 0–2% methanol, to give 3.3 gm (97.1%) of the title compound as a tan solid.

MS(m/e): 146(M$^+$)

Calculated for $C_9H_{10}N_2$: Theory: C, 73,94; H, 6.90; N, 19.16. Found: C, 73.78; H, 6.94; N, 19.04.

All of the 5-sulfonamido-1H-indoles required for the preparation of compounds of the invention are available by treating 5-amino-1H-indole with an appropriate sulfonyl chloride as described in Preparation V.

PREPARATION V

5-methanesulfonamido-1H-indole

To a solution of 2.0 gm (15.1 mMol) 5-amino-1H-indole in 25 mL tetrahydrofuran were added 2.4 mL (17.2 mMol) triethylamine. The reaction mixture was cooled in an ice bath as 1.23 mL (15.9 mMol) methanesulfonyl chloride were added dropwise. After 3.5 hours the reaction mixture was partitioned between 1N sodium hydroxide and ethyl acetate. The organic phase was extracted twice with 1N sodium hydroxide. All sodium hydroxide phases were combined, adjusted to pH=5 with acid and extracted well with ethyl acetate. These organic phases were combined, washed sequentially with water and saturated aqueous sodium chloride, dried over sodium sulfate and concentrated under reduced pressure to give 3.0 gm of a purple solid. This solid was crystallized from cyclohexane/ethyl acetate to give 2.5 gm (78.6%) of the title compound as light purple crystals.

m.p.=133°–135° C.

MS(m/e): 210(M$^+$)

Calculated for $C_9H_{13}N_2O_2S$: Theory: C, 51.41; H, 4.79; N, 13.32. Found: C, 51.16; H, 4.93; N, 13.27.

PREPARATION VI

5-amino-3-(1-methylpiperidin-4-yl)-1H-indole

A. From 5-nitro-1H-indole

To a solution of 10.38 gm 185 mMol) potassium hydroxide in 200 mL methanol were added 10.0 gm (61.7 mMol) 5-nitro-1H-indole followed by 13.96 gm (123 mMol) 1-methyl-4-piperidone. The mixture was heated to reflux for 4 days under a nitrogen atmosphere. The reaction mixture was then allowed to cool to ambient and the solid which formed filtered and washed with methanol. This solid was dried under vacuum at 50° C. The combined filtrates were then concentrated under reduced pressure and the residue subjected to flash chromatography, eluting with 92.5:7.5 dichloromethane:methanol. Fractions shown to contain product were combined and concentrated under reduced pressure. This solid was combined with that isolated directly from the reaction mixture to give 13.79 gm (87%) 5-nitro-3-(1-methyl-1,2,3,6-tetrahydropyridin-4-yl)-1H-indole.

To a solution of 38.2 gm (145 mMol) 5-nitro-3-(1-methyl-1,2,3,6-tetrahydropyridin-4-yl)-1H-indole in 1.9 L ethanol and 30 mL 5N HCl were added 10.0 gm 5% palladium on carbon. The reaction mixture was hydrogenated at ambient for 18 hours with an initial hydrogen pressure of 60 p.s.i. The reaction mixture was filtered and then concentrated under reduced pressure. The residue was dissolved in methanol and the solution filtered. This filtrate was concentrated under reduced pressure and the residue redissolved in ethanol. The solution was concentrated to about 500 mL and product allowed to crystallize. The crystals were filtered to give 48.9 gm (95%) of the title compound as its dihydrochloride salt, ethanol solvate.

m.p.=310°–320° C. (dec.)

MS(m/e): 229(M$^+$)

Calculated for $C_{14}H_{19}N_3 \cdot 2HCl \cdot C_2H_6O$: Theory: C, 55.17; H, 7.81; N, 12.06. Found: C, 55.23; H, 7.61; N, 12.30.

B. Via 5-amino-1H-indole

To a solution of 1.29 gm (20 mMol) potassium hydroxide in 10 mL methanol were added 1.32 gm (10 mMol) 5-amino-1H-indole followed by 2.46 mL (20 mMol) 1-methyl-4-piperidone. The reaction mixture was then heated to reflux for 18 hours. The reaction mixture was cooled to ambient, diluted with 20 ml water and the precipitate collected by filtration. The solid was recrystallized from ethyl acetate:methanol to give 1.11 gm (48.9%) 5-amino-3-(1-methyl-1,2,3,6-tetrahydropyr-idin-4-yl)-1H-indole as a tan solid (m.p.=200°–203° C.). The tan solid was subjected to flash chromatography, eluting with 100:20:0.5 dichloromethane:methanol:ammonium hydroxide, to give 0.99 gm 5-amino-3-(1-methyl-1,2,3,6-tetrahydropyridin-4-yl)-1H- indole as a cream colored solid (m.p.=212°–215° C. (ethyl acetate:methanol)).

MS(m/e): 227(M⁺)

Calculated for $C_{14}H_{17}N_3$: Theory: C, 73.98; H, 7.54; N, 18.49. Found: C, 73.76; H, 7.48; N, 18.22.

To a solution of 11.3 gm (50 mMol) 5-amino-3-(1-methyl-1,2,3,6-tetrahydropyridin-4-yl)-1H-indole in 250 mL methanol were added 3.0 gm 5% palladium on carbon. The mixture was hydrogenated at room temperature under an initial hydrogen pressure of 60 p.s.i. for 18 hours. The reaction mixture was filtered and the filtrate concentrated under reduced pressure to give a dark gum which was slurried in hexane to give the title compound as a brown solid.

MS(m/e): 229(M⁺)

PREPARATION VII

4-chloro-N-methyl-N-methoxybenzamide

To a solution of 11.38 gm (116.7 mMol) N-methoxy-N-methyl amine hydrochloride in 700 mL 1N sodium hydroxide was added a solution of 18.56 gm (106.04 mMol) 4-chlorobenzoyl chloride in 200 mL dichloromethane and the mixture was stirred at ambient. After 18 hours the phases were separated and the remaining aqueous was extracted well with dichloromethane. All organic phases were combined, dried over sodium sulfate and concentrated under reduced pressure to give 27.9 gm (95%) of the title compound as a clear oil.

MS(m/e): 165(M⁺)

IR: 3011, 2974, 2938, 1634 cm⁻¹

PREPARATION VIII

5-carboxy-3-(1-methyl-1,2,5,6-tetrahydropyridin-4-yl)-1H-indole

To a solution of 5.8 gm (90 mMol) potassium hydroxide in 50 mL methanol were added 4.83 gm (30 mMol) indole 5-carboxylic acid followed by 7.4 mL (60 mMol) 1-methyl-4-piperidone and the resulting solution was heated at reflux for 18 hours. The reaction mixture was then concentrated under reduced pressure and the resulting oil dissolved in 200 mL water. The solution was gradually neutralized by addition of 18 mL 5N hydrochloric acid. The precipitate which formed was isolated by filtration and washed with water to provide 6.09 gm after drying. This solid was dissolved in 100 mL 0.5N sodium hydroxide, filtered and the filtrate treated with 50 mL 1N hydrochloric acid. The solid which formed was filtered and dried under reduced pressure to provide 5.46 gm (71%) of the title compound.

m.p.=249° C.

MS(m/e): 256(M⁺)

Calculated for $C_{15}H_{16}N_2O_2$: Theory: C, 70.29; H, 6.29; N, 10.93. Found: C, 70.02; H, 6.39; N, 11.02.

PREPARATION IX

5-carboxy-3-(1-methylpiperidin-4-yl)-1H-indole 5-ethoxycarbonyl-3-(1-methyl-1,2,5,6-tetrahydropyridin-4-yl)-1H-indole A solution of 0.513 gm (2 mMol) 5-carboxy-3-(1-methyl-1,2,5,6-tetrahydropyridin-4-yl)-1H-indole in 5.1 mL ethanol was cooled in an ice bath while 0.51 mL sulfuric acid was added dropwise. The resulting mixture was heated at reflux for 5 hours. The now homogeneous solution was poured into 50 mL cold water and was then made basic with saturated ammonium hydroxide. The light yellow precipitate was collected by filtration and then recrystallized from ethanol to provide 0.24 gm (42%) of the desired compound as light yellow crystals.

m.p.=249° C.

MS(m/e): 284(M⁺)

Calculated for $C_{17}H_{20}N_2O_2$: Theory: C, 71.81; H, 7.09; N, 9.85. Found: C, 71.97; H, 7.25; N, 9.71.

5-ethoxycarbonyl-3-(1-methylpiperidin-4-yl)-1H-indole

To a solution of 3.24 gm (11.3 mMol) 5-ethoxycarbonyl-3-(1-methyl-1,2,5,6-tetrahydropyridin-4-yl)-1H-indole in 100 mL ethanol was added 0.8 gm 5% palladium an carbon and the reaction mixture hydrogenated at room temperature for 18 hours at an initial hydrogen pressure of 60 p.s.i. The reaction mixture was filtered and the filtrate concentrated under reduced pressure. The residual oil, which crystallized on standing at room temperature, was recrystallized from 30 mL acetonitrile to provide 1.79 gm (55%) of the desired compound as colorless crystals.

m.p.=155°–157° C.

MS(m/e): 286(M⁺)

Calculated for $C_{17}H_{22}N_2O_2$: Theory: C, 71.30; H, 7.74; N, 9.78. Found: C, 71.07; H, 7.88; N, 9.73.

Saponification/protonation

A mixture of 0.859 gm (3 mMol) 5-ethoxycarbonyl-3-(1-methylpiperidin-4-yl)-1H-indole, 6.0 mL ethanol and 6 mL 2N sodium hydroxide were heated at reflux for 2 hours. Ethanol was distilled from the resulting solution and the remaining aqueous solution was neutralized with 2.4 mL 5N hydrochloric acid. The resulting oil suspended in water is treated with a small amount of dichloromethane and cooled. The resulting solid is filtered, washed with water and acetone, and then recrystallized from 15 mL water to provide 0.308 gm (40%) of the title compound as colorless crystals.

m.p.>280° C.

MS(m/e): 258(M⁺)

Calculated for $C_{15}H_{18}N_2O_2$: Theory: C, 69.74; H, 7.02; N, 10.84. Found: C, 69.66; H, 7.03; N, 10.92.

PREPARATION X

Preparation of a polystyrene bound isocyanate resin

To a stirred suspension of 50 gm (61 mMol) aminomethylated polystyrene resin (1.22 mMol/gm) in 800 mL toluene was added 193 mL (366 mMol) 1.9M phosgene in toluene. After stirring the reaction mixture for 10 minutes, 67 mL (482 mMol) triethylamine was added and the reaction mixture was stirred for 18 hours at room temperature. The mixture was filtered and the recovered solid washed with 10 times with dichloromethane. A light pink resin mixed with a white solid was obtained. This solid mixture was resuspended in 700 mL dichloromethane, stirred for 10 minutes and then filtered and washed well with dichloromethane. The resulting solid was again suspended, stirred and washed with dichloromethane to provide the desired resin.

IR(KBr): 2252 cm⁻¹ (characteristic peak for —N=C=O)

EXAMPLE 1

5-phenylthio-3-(1-methylpiperidin-4-yl)-1H-indole

To a suspension of 0.21 gm (1.05 mMol) potassium hydride in 5.0 mL tetrahydrofuran at 0° C. was added a solution of 0.3 gm (1.0 mMol) 5-bromo-3-(1-methylpiperidin-4-yl)-1H-indole in 5.0 mL tetrahydrofuran and the solution stirred for about 30 minutes. The resulting mixture was cooled to about −78° C. and to it were added 1.47 mL (2.3 mMol) t-butyllithium, which had been pre-cooled to −78° C., via cannula. After about 15 minutes, 0.43 gm (2 mMol) diphenyl disulfide were added and the reaction mixture was allowed to warm gradually to ambient. The reaction mixture was then treated with 5N sodium hydroxide and extracted with diethyl ether. The ether extracts were combined, washed with saturated aqueous sodium chloride, dried over sodium sulfate and concentrated under reduced pressure. Purification by flash chromatography, eluting with 4.5:0.5:0.2 ethyl acetate:methanol:toluene, followed by recrystallization from hexane:diethyl ether gave 0.28 gm (85.1%) of the title compound as a white solid.

m.p.=147°–150° C.

MS(m/e): 322(M$^+$)

Calculated for $C_{20}H_{22}N_2S$: Theory: C, 74.49; H, 6.89; N, 8.69. Found: C, 74.27; H, 6.96; N, 8.77.

The compounds of Examples 2–5 were prepared employing the method described in detail in Example 1.

EXAMPLE 2

5-(4-methoxyphenyl)thio-3-(1-methylpiperidin-4-yl)-1H-indole

Using 0.3 gm (1.0 mMol) 5-bromo-3-(1-methylpiperidin-4-yl)-1H-indole and 0.55 gm (1.99 mMol) di(4-methoxyphenyl) disulfide gave 0.28 gm (64.0%) of the title compound as a colorless solid.

m.p.=160°–162° C.

MS(m/e): 352(M$^+$)

Calculated for $C_{21}H_{24}N_2OS$: Theory: C, 71.55; H, 6.86; N, 7.95. Found: C, 71.67; H, 6.89; N, 8.24.

EXAMPLE 3

5-benzylthio-3-(1-methylpiperidin-4-yl)-1H-indole

Using 0.325 gm (1.11 mMol) 5-bromo-3-(1-methylpiperidin-4-yl)-1H-indole and 0.55 gm (2.22 mMol) dibenzyl disulfide gave 0.065 gm (17.0%) of the title compound as a colorless solid.

m.p.=138°14 141° C.

MS(m/e): 336(M$^+$)

Calculated for $C_{21}H_{24}N_2S$: Theory: C, 74.96; H, 7.19; N, 8.33. Found: C, 75.55; H, 7.32; N, 7.95.

EXAMPLE 4

5-(pyridin-2-yl)thio-3-(1-methylpiperidin-4-yl)-1H-indole

Using 0.3 gm (1.0 mMol) 5-bromo-3-(1-methylpiperidin-4-yl)-1H-indole and 0.44 gm (1.99 mMol) di(pyridin-2-yl) disulfide gave 0.12 gm (37.0%) of the title compound as an off-white solid.

m.p.=83° C.

MS(m/e): 323(M$^+$)

Calculated for $C_{19}H_{21}N_3S$: Theory: C, 70.55; H, 6.54; N, 12.99. Found: C, 70.25; H, 6.60; N, 12.80.

EXAMPLE 5

5-(4-chlorophenyl)thio-3-(1-methylpiperidin-4-yl)-1H-indole

Using 0.4 gm (1.36 mMol) 5-bromo-3-(1-methylpiperidin-4-yl)-1H-indole and 0.78 gm (2.73 mMol) di(4-chlorophenyl)disulfide gave 0.39 gm (79.6%) of the title compound as a colorless solid.

m.p.=148°–150° C.

MS(m/e): 356(M$^+$)

Calculated for $C_{20}H_{21}N_2SCl$: Theory: C, 67.30; H, 5.93; N, 7.85. Found: C, 67.47; H, 6.10; N, 7.84.

EXAMPLE 6

5-benzoyl-3-(1-methylpiperidin-4-yl)-1H-indole

To a solution of 0.41 mL (0.73 mMol) phenyllithium in 4.0 mL tetrahydrofuran at 0° C. were added 0.10 gm (0.33 mMol) N-methyl-N-methoxy-5-carboxamido-3-(1-methylpiperidin-4-yl)-1H-indole (Preparation II) in 2.0 mL tetrahydrofuran. After 1 hour the reaction mixture was quenched with 2N sodium hydroxide and the mixture extracted well with diethyl ether. The ether extracts were then washed with saturated aqueous sodium chloride, dried over sodium sulfate and concentrated under reduced pressure. The residue was purified by radial chromatography (2 mm silica), eluting with 10:1 dichloromethane:methanol, to give 0.096 gm (91%) of the title compound as a light yellow solid.

m.p.=101° C.

MS(m/e): 319(M$^+$)

IR: 1644 cm$^{-1}$

Calculated for $C_{21}H_{22}N_2O \cdot H_2O$: Theory: C, 74.48; H, 7.19; N, 8.33. Found: C, 74.85; H, 7.00; N, 8.67.

The compounds of Examples 7–9 were prepared employing the method described in detail in Example 6.

EXAMPLE 7

5-acetyl-3-(1-methylpiperidin-4-yl)-1H-indole hydrochloride monohydrate

Using 0.30 gm (1.0 mMol) N-methyl-N-methoxy-5-carboxamido-3-(1-methylpiperidin-4-yl)-1H-indole (Preparation II) and 3.56 mL (4.98 mMol) methyllithium gave 5-acetyl-3-(1-methylpiperidin-4-yl)-1H-indole which was converted to its hydrochloride salt. 0.153 gm (60%) of the title compound were recovered.

m.p.=65° C.

MS(m/e): 256(M$^+$)

Calculated for $C_{16}H_{20}N_2O \cdot HCl \cdot H_2O$: Theory: C, 61.82; H, 7.46; N, 9.01. Found: C, 62.13; H, 7.86; N, 9.24.

EXAMPLE 8

5-pentanoyl-3-(1-methylpiperidin-4-yl)-1H-indole hydrochloride

Using 0.20 gm (0.66 mMol) N-methyl-N-methoxy-5-carboxamido-3-(1-methylpiperidin-4-yl)-1H-indole (Preparation II) and 1.66 mL (2.67 mMol) n-butyllithium gave 5-pentanoyl-3-(1-methylpiperidin-4-yl)-1H-indole which was converted to its hydrochloride salt. 0.124 gm (63%) of the title compound were recovered as a tan solid which was crystallized from ethanol:diethyl ether.

m.p.=242°–245° C.

MS(m/e): 299(M$^+$)

Calculated for $C_{19}H_{26}N_2O \cdot HCl$: Theory: C, 68.15; H, 8.13; N, 8.37. Found: C, 67.89; H, 8.05; N, 8.64.

EXAMPLE 9

5-phenylacetyl-3-(1-methylpiperidin-4-yl)-1H-indole

Using 0.30 gm (1.0 mMol) N-methyl-N-methoxy-5-carboxamido-3-(1-methylpiperidin-4-yl)-1H-indole (Preparation II) and 2.5 mL (5.0 mMol) benzylmagnesium chloride gave 0.22 gm (66%) of the title compound as an off-white solid.

m.p.=69° C.
MS(m/e): 333(M$^+$)
IR: 1662 cm$^{-1}$
Calculated for $C_{22}H_{24}N_2O$: Theory: C, 79.48; H, 7.28; N, 8.43. Found: C, 79.68; H, 7.47; N, 8.61.

EXAMPLE 10

5-(4-methoxybenzoyl)-3-(1-methylpiperidin-4-yl)-1H-indole

To a solution of 0.35 mL (2.82 mMol) 4-methoxy-1-bromobenzene in 3.0 mL tetrahydrofuran at −78° C. were added 1.83 mL (2.93 mMol) n-butyllithium and the reaction mixture stirred for 30 minutes at −78° C. To this solution were then added 0.17 gm (0.56 mMol) N-methyl-N-methoxy-5-carboxamido-3-(1-methylpiperidin-4-yl)-1H-indole (Preparation II) in 2.0 mL tetrahydrofuran. The reaction mixture was allowed to warm gradually to ambient and was then quenched with 2N sodium hydroxide. The resulting mixture was extracted well with diethyl ether. The ether extracts were then washed with saturated aqueous sodium chloride, dried over sodium sulfate and concentrated under reduced pressure. The residue was purified by radial chromatography (2 mm silica), eluting with 10:1 dichloromethane:methanol, to give 0.135 gm (72%) of the title compound as a light yellow solid.

MS(m/e): 349(M$^+$)
Calculated for $C_{22}H_{24}N_2O_2$: Theory: C, 75.84; H, 6.94; N, 8.04. Found: C, 75.85; H, 7.11; N, 8.06.

The compounds of Examples 11–19 were prepared employing the method described in detail in Example 10.

EXAMPLE 11

5-(4-fluorobenzoyl)-3-(1-methylpiperidin-4-yl)-1H-indole

Using 0.20 gm (0.66 mMol) N-methyl-N-methoxy-5-carboxamido-3-(1-methylpiperidin-4-yl)-1H-indole (Preparation II) and 0.36 mL (4.98 mMol) 4-fluoro-1-bromobenzene gave 0.158 gm (71%) of the title compound as an off-white solid.

m.p.=89° C.
MS(m/e): 336(M$^+$)

EXAMPLE 12

5-(4-methylbenzoyl)-3-(1-methylpiperidin-4-yl)-1H-indole

Using 0.20 gm (0.66 mMol) N-methyl-N-methoxy-5-carboxamido-3-(1-methylpiperidin-4-yl)-1H-indole (Preparation II) and 0.41 mL (3.32 mMol) 4-methyl-1-bromobenzene gave 0.180 gm (79%) of the title compound as a yellow solid.

m.p.=92° C.
MS(m/e): 332(M$^+$)
Calculated for $C_{22}H_{24}N_2O$: Theory: C, 79.48; H, 7.28; N, 8.43. Found: C, 79.60; H, 7.40; N, 8.54.

EXAMPLE 13

5-(4-trifluoromethylbenzoyl)-3-(1-methylpiperidin-4-yl)-1H-indole

Using 0.15 gm (0.50 mMol) N-methyl-N-methoxy-5-carboxamido-3-(1-methylpiperidin-4-yl)-1H-indole (Preparation II) and 0.35 mL (2.49 mMol) 4-trifluoromethyl-1-bromobenzene gave 0.122 gm (64%) of the title compound as a yellow solid.

m.p.=160°–162° C.
MS(m/e): 386(M$^+$)
Calculated for $C_{22}H_{21}N_2OF_3$: Theory: C, 68.38; H, 5.48; N, 7.25. Found: C, 68.54; H, 5.72; N, 7.47.

EXAMPLE 14

5-(4-trifluoromethoxybenzoyl)-3-(1-methylpiperidin-4-yl)-1H-indole

Using 0.17 gm (0.56 mMol) N-methyl-N-methoxy-5-carboxamido-3-(1-methylpiperidin-4-yl)-1H-indole (Preparation II) and 0.49 mL (3.32 mMol) 4-trifluoromethoxy-1-bromobenzene gave 0.157 gm (69%) of the title compound as a light yellow solid.

m.p.=172°–175° C.
MS(m/e): 402(M$^+$)
Calculated for $C_{22}H_{21}N_2O_2F_3$: Theory: C, 65.66; H, 5.26; N, 6.96. Found: C, 65.86; H, 5.45; N, 7.20.

EXAMPLE 15

5-(4-dimethylaminobenzoyl)-3-(1-methylpiperidin-4-yl)-1H-indole

Using 0.20 gm (0.66 mMol) N-methyl-N-methoxy-5-carboxamido-3-(1-methylpiperidin-4-yl)-1H-indole (Preparation II) and 0.80 gm (3.98 mMol) 4-dimethylamino-1-bromobenzene gave 0.159 gm (66%) of the title compound as a light yellow solid.

m.p.=103°–104° C.
MS(m/e): 361(M$^+$)
Calculated for $C_{23}H_{27}N_3O \cdot 0.5 H_2O$: Theory: C, 74.56; H, 7.62; N, 11.34. Found: C, 74.46; H, 7.53; N, 11.04.

EXAMPLE 16

5-(2-naphthoyl)-3-(1-methylpiperidin-4-yl)-1H-indole

Using 0.20 gm (0.66 mMol) N-methyl-N-methoxy-5-carboxamido-3-(1-methylpiperidin-4-yl)-1H-indole (Preparation II) and 0.60 gm (3.32 mMol) 2-bromonaphthalene gave 0.178 gm (73%) of the title compound as a light yellow solid.

m.p.=92° C.
MS(m/e): 368(M$^+$)

EXAMPLE 17

5-(2-Pyridinecarbonyl)-3-(1-methylpiperidin-4-yl)-1H-indole

Using 0.20 gm (0.66 mMol) N-methyl-N-methoxy-5-carboxamido-3-(1-methylpiperidin-4-yl)-1H-indole (Preparation II) and 0.32 mL (3.32 mMol) 2-bromopyridine gave 0.089 gm (42%) of the title compound as a light yellow solid.

m.p.=90° C.
MS(m/e): 319(M$^+$)

EXAMPLE 18

5-(N-phenylcarboxamido)-3-(1-methylpiperidin-4-yl)-1H-indole

Using 0.20 gm (0.66 mMol) N-methyl-N-methoxy-5-carboxamido-3-(1-methylpiperidin-4-yl)-1H-indole (Preparation II) and 0.30 mL (3.32 mMol) aniline gave 0.118 gm (53%) of the title compound as a light tan solid.

m.p.=97° C.

MS(m/e): 333(M$^+$)

Calculated for $C_{21}H_{23}N_3O\cdot0.25\ H_2O$: Theory: C, 74.64; H, 7.01; N, 12.43. Found: C, 74.29; H, 7.06; N, 12.51.

EXAMPLE 19

5-(N-benzylcarboxamido)-3-(1-methylpiperidin-4-yl)-1H-indole

Using 1.2 gm (4.0 mMol) N-methyl-N-methoxy-5-carboxamido-3-(1-methylpiperidin-4-yl)-1H-indole (Preparation II) and 2.2 mL (20.0 mMol) benzylamine gave 0.788 gm (57%) of the title compound as a white solid.

m.p.=87° C.

MS(m/e): 347(M$^+$)

Calculated for $C_{22}H_{25}N_3O$: Theory: C, 76.05; H, 7.25; N, 2.09. Found: C, 76.06; H, 7.51; N, 12.35.

EXAMPLE 20

5-(4-chlorobenzoyl)-3-(1-methylpiperidin-4-yl)-1H-indole

To a suspension of 0.21 gm (1.05 mMol) potassium hydride in 5.0 mL tetrahydrofuran at 0° C. were added a solution of 0.3 gm (1.0 mMol) 5-bromo-3-(1-methylpiperidin-4-yl)-1H-indole in 5.0 mL tetrahydrofuran and the solution stirred for about 30 minutes. The resulting mixture was cooled to about −78° C. and to it were added 1.47 mL (2.3 mMol) t-butyllithium, which had been pre-cooled to −78° C., via cannula. After about 15 minutes, a solution of 1.0 gm (5.0 mMol) N-methyl-N-methoxy-4-chlorobenzamide (Preparation VII) in 3.0 mL tetrahydrofuran were added. The reaction mixture was allowed to gradually warm to ambient and was then quenched with 2N sodium hydroxide. The mixture extracted well with diethyl ether and the ether extracts were then washed with saturated aqueous sodium chloride, dried over sodium sulfate and concentrated under reduced pressure. The residue was purified by radial chromatography (2 mm silica), eluting with 95:5 ethyl acetate:methanol, to give the title compound as a light yellow solid.

m.p.=133° C.

MS(m/e): 352(M$^+$)

Calculated for $C_{21}H_{21}N_2OCl\cdot0.5H_2O$: Theory: C, 69.70; H, 6.13; N, 7.74. Found: C, 70.02; H, 6.20; N, 7.93.

EXAMPLE 21

5-methanesulfonylamino-3-(1-methyl-1,2,3,6-tetrahydropyridin-4-yl)-1H-indole

To a solution of 1.2 gm (21.4 mMol) potassium hydroxide in 12 mL methanol was added 1.0 gm (4.76 mMol) 5-methanesulfonylamino-1H-indole followed by 0.76 mL (6.2 mMol) 1-methyl-4-piperidone. The homogeneous solution was heated to reflux for 18 hours under nitrogen. The reaction mixture was then cooled and concentrated under reduced pressure. The residue was dissolved in water and the pH of the solution adjusted from 14 to 8–9 by the addition of acid. The precipitate that formed was filtered, washed with water and dried under vacuum to give 1.3 gm (89.6%) of the title compound as a tan solid.

m.p.=210°–214° C.

MS(m/e): 305(M$^+$)

Calculated for $C_{15}H_{19}N_3O_2S$: Theory: C, 58.99; H, 6.27; N, 13.76. Found: C, 59.00; H, 6.20; N, 13.74.

The compounds of Examples 22–29 were prepared employing the procedure described in detail in Example 21.

EXAMPLE 22

N-methyl-5-methanesulfonylamino-3-(1-methyl-1,2,3,6-tetrahydropyridin-4-yl)-1H-indole Beginning with 1.23 gm (5.5 mMol) N-methyl-5-methanesulfonylamino-1H-indole and 0.88 mL (7.1 mMol) 1-methyl-4-piperidone, 1.4 gm (80%) of the title compound were recovered as a tan, crystalline powder.

m.p.=198°–202° C.

MS(m/e): 319(M$^+$)

Calculated for $C_{16}H_{21}N_3O_2S$: Theory: C, 60.16; H, 6.63; N, 13.16. Found: C, 60.30; H, 6.76; N, 12.97.

EXAMPLE 23

2-methyl-5-methanesulfonylamino-3-(1-methyl-1,2,3,6-tetrahydropyridin-4-yl)-1H-indole Beginning with 1.37 gm (6.1 mMol) 2-methyl-5-methanesulfonylamino-1H-indole and 0.98 mL (7.9 mMol) 1-methyl-4-piperidone, 0.65 gm (33.3%) of the title compound were recovered as a yellow solid.

m.p.=176°–184° C.

MS(m/e): 320(M+1)

Calculated for $C_{16}H_{21}N_3O_2S$: Theory: C, 60.16; H, 6.63; N, 13.16. Found: C, 60.39; H, 6.48; N, 13.10.

EXAMPLE 24

5-ethanesulfonylamino-3-(1-methyl-1,2,3,6-tetrahydropyridin-4-yl)-1H-indole

Beginning with 1.45 gm (6.5 mMol) 5-ethanesulfonylamino-1H-indole and 1.03 mL (8.4 mMol) 1-methyl-4-piperidone, 1.23 gm (59.7%) of the title compound were recovered as pale orange crystals.

m.p.=224°–226° C.

MS(m/e): 319(M$^+$)

Calculated for $C_{16}H_{21}N_3O_2S$: Theory: C, 60.16; H, 6.63; N, 13.16. Found: C, 60.45; H, 6.69; N, 13.22.

EXAMPLE 25

5-(N,N-dimethylamino)sulfonylamino-3-(1-methyl-1,2,3,6-tetrahydropyridin-4-yl)-1H-indole Beginning with 1.17 gm (4.89 mMol) 5-(N,N-dimethylamino)sulfonylamino-1H-indole and 0.78 mL (6.4 mMol) 1-methyl-4-piperidone, 1.19 gm (72.6%) of the title compound were recovered as a pale yellow powder.

m.p.=207°–208° C.

MS(m/e): 334(M$^+$)

Calculated for $C_{16}H_{22}N_4O_2S$: Theory: C, 57.46; H, 6.63; N, 16.75. Found: C, 57.69; H, 6.71; N, 16.60.

EXAMPLE 26

5-methanesulfonylamino-3-(1-ethyl-1,2,3,6-tetrahydropyridin-4-yl)-1H-indole

Beginning with 1.50 gm (7.1 mMol) 5-methanesulfonylamino-1H-indole and 1.25 mL (9.3 mMol) 1-ethyl-4-piperidone, 1.34 gm (58.8%) of the title compound were recovered as a light yellow, crystalline powder.

m.p.=218°–219° C. (dec.)

MS(m/e): 320(M+1)

Calculated for $C_{16}H_{21}N_3O_2S$: Theory: C, 60.16; H, 6.63; N, 13.16. Found: C, 59.89; H, 6.39; N, 13.24.

EXAMPLE 27

5-methanesulfonylamino-3-(1-propyl-1,2,3,6-tetrahydropyridin-4-yl)-1H-indole

Beginning with 1.50 gm (7.1 mMol) 5-methanesulfonylamino-1H-indole and 1.4 mL (9.3 mMol) 1-propyl-4-piperidone, 2.1 gm (88.2%) of the title compound were recovered as a yellow powder.

m.p.=217°–218.5° C. (dec.)

MS(m/e): 334(M+1)

Calculated for $C_{17}H_{23}N_3O_2S$: Theory: C, 61.23; H, 6.95; N, 12.60. Found: C, 61.51; H, 7.23; N, 12.30.

EXAMPLE 28

5-methanesulfonylamino-3-(1-isopropyl-1,2,3,6-tetrahydropyridin-4-yl)-1H-indole

Beginning with 1.0 gm (4.76 mMol) 5-methanesulfonylamino-1H-indole and 0.873 gm (6.2 mMol) 1-isopropyl-4-piperidone, 1.02 gm (64.2%) of the title compound were recovered as a tan powder.

m.p.=211°–213° C. (dec.)

MS(m/e): 333(M$^+$)

Calculated for $C_{17}H_{23}N_3O_2S$: Theory: C, 61.23; H, 6.95; N, 12.60. Found: C, 60.95; H, 6.87; N, 12.60.

EXAMPLE 29

5-methanesulfonylamino-3-(1-butyl-1,2,3,6-tetrahydropyridin-4-yl)-1H-indole

Beginning with 1.0 gm (4.76 mMol) 5-methanesulfonylamino-1H-indole and 0.96 gm (6.2 mMol) 1-butyl-4-piperidone, 1.4 gm (84.8%) of the title compound were recovered as a yellow powder.

m.p.=202°–204° C.

MS(m/e): 347(M$^+$)

Calculated for $C_{18}H_{25}N_3O_2S$: Theory: C, 62.22; H, 7.25; N, 12.09. Found: C, 62.10; H, 7.11; N, 12.28.

EXAMPLE 30

5-methanesulfonylamino-3-(1-methylpiperidin-4-yl)-1H-indole oxalate

To a solution 0.815 gm (2.67 mMol) 5-methanesulfonylamino-3-(1-methyl-1,2,3,6-tetrahydropyridin-4-yl)-1H-indole in 125 mL methanol were added 0.815 gm 5% palladium on carbon. The mixture was hydrogenated at ambient for 18 hours with an initial hydrogen pressure of 60 p.s.i. The reaction mixture was filtered and the filtrate concentrated under reduced pressure. The residual oil was purified by flash chromatography, eluting with 90:10 dichloromethane:methanol. Fractions shown to contain product were combined and concentrated under reduced pressure. The residue was dissolved in methanol and to it were added oxalic acid. The suspension was filtered to give 0.261 gm (25%) of the title compound.

m.p.=119.1° C.

MS(m/e): 307(M$^+$)

EXAMPLE 31

5-(N-methyl)methanesulfonylamino-3-(1-methylpiperidin-4-yl)-1H-indole

Following the procedure described in detail in Example 30, 0.807 gm (2.53 mMol) 5-(N-methyl)methanesulfonylamino-3-(1-methyl-1,2,3,6-tetrahydropyridin-4-yl)-1H-indole (Example 22) was hydrogenated to give 0.075 gm (9.3%) of the title compound as a tan foam.

MS(m/e): 322(M+1)

Calculated for $C_{16}H_{23}N_3O_2S$: Theory: C, 59.79; H, 7.21; N, 13.07. Found: C, 59.62; H, 7.33; N, 12.82.

EXAMPLE 32

2-methyl-5-methanesulfonylamino-3-(1-methylpiperidin-4-yl)-1H-indole

To a solution of 0.45 gm (1.41 mMol) 2-methyl-5-methanesulfonylamino-3-(1,2,3,6-tetrahydropyridin-4-yl)-1H-indole (Example 23) in 125 mL methanol were added 0.11 gm 5% palladium on carbon and the reaction mixture hydrogenated at ambient temperature with an initial hydrogen pressure of 60 p.s.i. After 18 hours the reaction mixture was filtered and the filtrate concentrated under reduced pressure to give a yellow oil. The oil was purified by radial chromatography (2 mm silica gel), eluting with 100:5:0.5 dichloromethane: methanol:ammonium hydroxide, to give 0.21 gm of a yellow foam which was then precipitated from ethyl acetate/hexanes to give 0.18 gm (39.7%) of the title compound as a white powder.

m.p.=124°–128° C.

MS(m/e): 321(M$^+$)

Calculated for $C_{16}H_{23}N_3O_2S$: Theory: C, 59.79; H, 7.21; N, 13.07. Found: C, 59.88; H, 7.24; N, 13.33.

The compounds of Examples 33–38 were prepared by the procedure described in detail in Example 32.

EXAMPLE 33

5-ethanesulfonylamino-3-(1-methylpiperidin-4-yl)-1H-indole 0.70 gm (2.2 mMol) 5-ethanesulfonylamino-3-(1-methyl-1,2,3,6-tetrahydropyridin-4-yl)-1H-indole (Example 24) were hydrogenated to give 0.545 gm (77.4%) of the title compound as a white powder.

m.p.=176°–178° C.

MS(m/e): 322(M+1)

Calculated for $C_{16}H_{23}N_3O_2S$: Theory: C, 59.79; H, 7.21; N, 13.07. Found: C, 60.07; H, 7.22; N, 12.79.

EXAMPLE 34

5-(N,N-dimethylamino)sulfonylamino-3-(1-methylpiperidin-4-yl)-1H-indole 0.66 gm (2.0 mMol) 5-(N,N-dimethylamino)sulfonylamino-3-(1-methyl-1,2,3,6-tetrahydropyridin-4-yl)-1H-indole (Example 25) were hydrogenated to give 0.333 gm (50.2%) of the title compound as an off-white powder.

m.p.=179°–181° C. (dec.)

MS(m/e): 336(M$^+$)

Calculated for $C_{16}H_{24}N_4O_2S$: Theory: C, 57.12; H, 7.19; N, 16.65. Found: C, 57.38; H, 7.27; N, 16.87.

EXAMPLE 35

5-methanesulfonylamino-3-(1-ethylpiperidin-4-yl)-1H-indole 0.96 gm (3.0 mMol) 5-methanesulfonylamino-3-(1-ethyl-1,2,3,6-tetrahydropyridin-4-yl)-1H-indole (Example 26) were hydrogenated to give 0.531 gm (55.0%) of the title compound as an off-white powder.

m.p.=179°–181° C.

MS(m/e): 321(M$^+$)

Calculated for $C_{16}H_{23}N_3O_2S$: Theory: C, 59.79; H, 7.21; N, 13.07. Found: C, 59.50; H, 7.11; N, 12.81.

EXAMPLE 36

5-methanesulfonylamino-3-(1-propylpiperidin-4-yl)-1H-indole 1.0 gm (3.0 mMol) 5-methanesulfonylamino-3-(1-propyl-1,2,3,6-tetrahydropyridin-4-yl)-1H-indole (Example 27) were hydrogenated to give 0.376 gm (37.2%) of the title compound as an off-white powder.

m.p.=87°–90° C.

MS(m/e): 335(M$^+$)

Calculated for $C_{17}H_{25}N_3O_2S$: Theory: C, 60.87; H, 7.51; N, 12.53. Found: C, 61.12; H, 7.32; N, 12.70.

EXAMPLE 37

5-methanesulfonylamino-3-(1-isopropylpiperidin-4-yl)-1H-indole 0.75 gm (2.25 mMol) 5-methanesulfonylamino-3-(1-isopropyl-1,2,3,6-tetrahydropyridin-4-yl)-1H-indole (Example 28) were hydrogenated to give 0.310 gm (41.1%) of the title compound as a white powder.

m.p.=104°–108° C.

MS(m/e): 335(M$^+$)

Calculated for $C_{17}H_{25}N_3O_2S \cdot C_2H_2O_4$: Theory: C, 53.63; H, 6.40; N, 9.87. Found: C, 53.38; H, 6.34; N, 9.66.

EXAMPLE 38

5-methanesulfonylamino-3-(1-butylpiperidin-4-yl)-1H-indole 1.05 gm (3.02 mMol) 5-methanesulfonylamino-3-(1-butyl-1,2,3,6-tetrahydropyridin-4-yl)-1H-indole (Example 29) were hydrogenated to give 0.255 gm (24.0%) of the title compound as a tan foam.

m.p.=78° C.

MS(m/e): 349(M$^+$)

Calculated for $C_{18}H_{27}N_3O_2S$: Theory: C, 61.86; H, 7.79; N, 12.02. Found: C, 61.66; H, 7.74; N, 11.87.

EXAMPLE 39

5-benzenesulfonylamino-3-(1-methylpiperidin-4-yl)-1H-indole

To a solution of 2.00 gm (5.74 mMol) 5-amino-3-(1-methylpiperidin-4-yl)-1H-indole in 50.0 mL dichloromethane were added 1.63 gm (20.7 mMol)pyridine and the solution was cooled to 0° C. To this cooled solution were then added dropwise a solution of 2.23 gm (12.6 mMol) benzenesulfonyl chloride in 50 mL dichloromethane. The reaction mixture was allowed to warm gradually to ambient. After 24 hours the reaction mixture was washed with 100 mL water and the remaining organics concentrated under reduced pressure. The residue was suspended in water and the pH adjusted to 14 with sodium hydroxide. The aqueous phase was then extracted well with dichloromethane. The organic phase was washed sequentially with water and saturated aqueous sodium chloride, dried over sodium sulfate and concentrated under reduced pressure. The aqueous phases were combined and the pH adjusted to 10 by the addition of acid and extracted again with 3:1 chloroform:isopropanol. These organic extracts were combined and concentrated under reduced pressure. The combined residues were subjected to flash chromtography, eluting with a gradient system of 100:10:0.5 to 100:11:0.5 dichloromethane:methanol:ammonium hydroxide, giving 0.83 gm (39.1%) of the title compound as a white powder.

m.p.=246°–249° C. (dec.)

MS(m/e): 370(M+1)

Calculated for $C_{20}H_{23}N_3O_2S$: Theory: C, 65.02; H, 6.27; N, 11.37. Found: C, 64.78; H, 6.09; N, 11.44.

EXAMPLE 40

5-(4-iodobenzenesulfonyl)amino-3-(1-methylpiperidin-4-yl)-1H-indole

Following the procedure described in detail in Example 39, 0.791 gm (3.45 mMol) 5-amino-3-(1-methylpiperidin-4-yl)-1H-indole and 1.1 gm (3.62 mMol) 4-iodobenzenesulfonyl chloride were used to prepare 0.809 (47.3%) of the title compound as a white powder. m.p.>250° C.

MS(m/e): 495(M+)

Calculated for $C_{20}H_{22}IN_3O_2S$: Theory: C, 48.49; H, 4.48; N, 8.48. Found: C, 48.68; H, 4.47; N, 8.26.

EXAMPLE 41

5-(di(trifluoromethanesulfonyl))amino-3-(1-methylpiperidin-4-yl)-1H-indole hydrochloride To a suspension of 1.00 gm (2.87 mMol) 5-amino-3-(1-methylpiperidin-4-yl)-1H-indole dihydrochloride in 100 mL dichloromethane were added 2.5 mL (14.3 mMol) diisopropylethylamine followed by 1.06 mL (6.3 mMol) trifluoromethanesulfonic anhydride. After 20 minutes the reaction mixture was washed with water, dried over sodium sulfate and concentrated under reduced pressure. The residue was purified by flash chromatography, eluting with dichloromethane containing 15% methanol, to give 5-(di(trifluoromethanesulfonyl))amino-3-(1-methylpiperidin-4-yl)-1H-indole. This material was converted to its hydrochloride salt and was crystallized from acetonitrile to give 0.34 gm (22.3%) of the title compound.

m.p.=175°–185° C. (dec.)

MS(m/e): 493(M$^+$)

Calculated for $C_{16}H_{17}N_3O_4S_2F_6 \cdot HCl$: Theory: C, 36.27; H, 3.23; N, 7.93. Found: C, 36.48; H, 3.58; N, 7.85.

EXAMPLE 42

5-(methoxycarbonyl)amino-3-(1-methylpiperidin-4-yl)-1H-indole

To a mixture of 10 mg (0.0437 mMol) 5-amino-3-(1-methyl-piperidin-4-yl)-1H-indole and 15.0 mg (0.131 mMol) polyvinyl-pyridine in 3.0 mL dichloromethane were added 4.3 mg (0.0458 mMol) methyl chloroformate. The reaction mixture was mixed for 18 hours at ambient temperature. To this mixture were then added 170 mg (0.137 mMol) aminomethylated polystyrene and the reaction mixed for an additional 18 hours. The reaction mixture was then filtered and the volatiles evaporated to give 10.2 mg (81%) of the title compound.

MS(m/e): 287(M$^+$)

The compounds of Examples 43–50 were prepared by the procedure described in detail in Example 42.

EXAMPLE 43

5-(ethoxycarbonyl)amino-3-(1-methylpiperidin-4-yl)-1H-indole

Beginning with 10 mg (0.0437 mMol) 5-amino-3-(1-methyl-piperidin-4-yl)-1H-indole and 4.97 mg (0.0458 mMol) ethyl chloroformate, 11.1 mg (84%) of the title compound were recovered.

MS(m/e): 301(M$^+$)

EXAMPLE 44

5-(propoxycarbonyl)amino-3-(1-methylpiperidin-4-yl)-1H-indole

Beginning with 10 mg (0.0437 mMol) 5-amino-3-(1-methyl-piperidin-4-yl)-1H-indole and 5.62 mg (0.0458 mMol) propyl chloroformate, 11.2 mg (81%) of the title compound were recovered.

MS(m/e): 316(M$^+$)

EXAMPLE 45

5-(allyloxycarbonyl)amino-3-(1-methylpiperidin-4-yl)-1H-indole

Beginning with 10 mg (0.0437 mMol) 5-amino-3-(1-methyl-piperidin-4-yl)-1H-indole and 5.5 mg (0.0458 mMol) allyl chloroformate, 9.7 mg (71%) of the title compound were recovered.

MS(m/e): 314(M$^+$)

EXAMPLE 46

5-((2-methoxyethyl)carbonyl)amino-3-(1-methylpiperidin-4-yl)-1H-indole

Beginning with 13 mg (0.0567 mMol) 5-amino-3-(1-methyl-piperidin-4-yl)-1H-indole and 8.65 mg (0.062 mMol) 2-methoxyethyl chloroformate, 10.25 mg (54%) of the title compound were recovered.

MS(m/e): 332(M$^+$)

EXAMPLE 47

5-(cyclopentyloxycarbonyl)amino-3-(1-methylpiperidin-4-yl)-1H-indole

Beginning with 13 mg (0.0567 mMol) 5-amino-3-(1-methyl-piperidin-4-yl)-1H-indole and 9.27 mg (0.062 mMol) cyclopentyl chloroformate, 18.1 mg (93% of the title compound were recovered.

MS(m/e): 342(M$^+$)

EXAMPLE 48

5-(phenoxycarbonyl)amino-3-(1-methylpiperidin-4-yl)-1H-indole

Beginning with 10 mg (0.0437 mMol) 5-amino-3-(1-methyl-piperidin-4-yl)-1H-indole and 7.2 mg (0.0458 mMol) phenyl chloroformate, 13.9 mg (91%) of the title compound were recovered.

MS(m/e): 350(M$^+$)

EXAMPLE 49

5-(4-methoxyphenyl)oxycarbonyl)amino-3-(1-methylpiperidin-4-yl)-1H-indole

Beginning with 13 mg (0.0567 mMol) 5-amino-3-(1-methyl-piperidin-4-yl)-1H-indole and 11.1 mg (0.062 mMol) 4-methoxyphenyl chloroformate, 13.4 mg (63%) of the title compound were recovered.

MS(m/e): 380(M$^+$)

EXAMPLE 50

5-(4-chlorophenyl)oxycarbonyl)amino-3-(1-methylpiperidin-4-yl)-1H-indole

Beginning with 13 mg (0.0567 mMol) 5-amino-3-(1-methyl-piperidin-4-yl)-1H-indole and 11.1 mg (0.062 mMol) 4-chlorophenyl chloroformate, 18.1 mg (93%) of the title compound were recovered.

MS(m/e):

EXAMPLE 51

N-methyl-N'-(3-(1-methylpiperidin-4-yl)-1H-indol-5-yl)urea

To a solution of 2.0 gm (5.74 mMol) 5-amino-3-(1-methylpiperidin-4-yl)-1H-indole dihydrochloride monoethanolate and 5.0 mL (36 mMol) triethylamine in 100 mL dichloromethane were added 0.74 mL (12.6 mMol) methyl isocyanate. The reaction mixture was stirred for 15 minutes and was then washed with 100 mL of water. The remaining organics were dried over sodium sulfate and concentrated under reduced pressure. The resultant residue was crystallized from acetonitrile to give 1.05 gm (64%) of the title compound.

MS(m/e): 287(M+1)

Calculated for $C_{16}H_{22}N_4O$: Theory: C, 69.11; H, 7.74; N, 19.56. Found: C, 69.37; H, 7.82; N, 19.67.

EXAMPLE 52

N-phenyl-N'-(3-(1-methylpiperidin-4-yl)-1H-indol-5-yl)urea hydrochloride

To a solution of 2.0 gm (5.74 mMol) 5-amino-3-(1-methylpiperidin-4-yl)-1H-indole dihydrochloride monoethanolate and 5.0 mL (36 mMol) triethylamine in 100 mL dichloromethane were added 1.37 mL (12.6 mMol) phenyl isocyanate. The reaction mixture was stirred for 15 minutes and was then washed with 100 mL of water. The remaining organics were dried over sodium sulfate and concentrated under reduced pressure. The resultant residue was crystallized from acetonitrile to give 1.40 gm (70%) N-phenyl-N'-(3-(1-methylpiperidin-4-yl)-1H-indol-5-yl)urea. This material was dissolved in methanol and to it was added an equivalent of methanolic hydrogen chloride. The solution was then concentrated under reduced pressure and the residual oil crystallized from ethanol to give the title compound.

m.p.=215°–220° C.

MS(m/e): 348(M$^+$)

Calculated for $C_{21}H_{24}N_4O \cdot HCl$: Theory: C, 65.53; H, 6.55; N, 14.56. Found: C, 65.27; H, 6.43; N, 14.35.

EXAMPLE 53

N-ethyl-N'-(3-(1-methylpiperidin-4-yl)-1H-indol-5-yl)urea

To a solution of 15.0 mg 0.0655 mMol) 5-amino-3-(1-methylpiperidin-4-yl)-1H-indole in 3.0 mL chloroform were added 9.3 mg 0.131 mMol) ethyl isocyanate. The reaction was mixed for 48 hours and to it were then added 0.23 gm 0.131 mMol)aminomethylated polystyrene and the reaction mixed for an additional 18 hours. The reaction mixture was then filtered and the volatiles evaporated to give 16.1 mg (82%) of the title compound.

MS(m/e):

The compounds of Examples 54–75 were prepared by the procedure described in detail in Example 53.

EXAMPLE 54

N-Propyl-N'-(3-(1-methylpiperidin-4-yl)-1H-indol-5-yl)urea

Beginning with 15.0 mg 0.0655 mMol) 5-amino-3-(1-methyl-piperidin-4-yl)-1H-indole and 11.1 mg (0.131 mMol) propyl isocyanate, 5.8 mg of the title compound were recovered.

MS(m/e): 315($M^+$)

EXAMPLE 55

N-allyl-N'-(3-(1-methylpiperidin-4-yl)-1H-indol-5-yl)urea

Beginning with 15.0 mg 0.0655 mMol) 5-amino-3-(1-methyl-piperidin-4-yl)-1H-indole and 11.1 mg (0.131 mMol) allyl isocyanate, 19.6 mg (96%) of the title compound were recovered.

MS(m/e): 313($M^+$)

EXAMPLE 56

N-isopropyl-N'-(3-(1-methylpiperidin-4-yl)-1H-indol-5-yl)urea

Beginning with 15.0 mg 0.0655 mMol) 5-amino-3-(1-methyl-piperidin-4-yl)-1H-indole and 11.13 mg (0.131 mMol) isopropyl isocyanate, 21.9 mg of the title compound were recovered.

MS(m/e): 315($M^+$)

EXAMPLE 57

N-n-butyl-N'-(3-(1-methylpiperidin-4-yl)-1H-indol-5-yl)urea

Beginning with 15.0 mg (0.0655 mMol) 5-amino-3-(1methyl-dimethyl-piperidin-4-yl)-1H indole and 11.1 mg (0.131 mMol) n-butyl isocyanate, 20.6 mg (96%) of the title compound were recovered.

MS(m/e): 329($M^+$)

EXAMPLE 58

N-cyclohexyl-N'-(3-(1-methylpiperidin-4-yl)-1H-indol-5-yl)urea

Beginning with 15.0 mg 0.0655 mMol) 5-amino-3-(1-methyl-piperidin-4-yl)-1H-indole and 16.37 mg (0.131 mMol) cyclohexyl isocyanate, 20.1 mg (87%) of the title compound were recovered.

MS(m/e): 355($M^+$)

EXAMPLE 59

N-(1-ethoxycarbonyl-2-methylpropyl)-N'-(3-(1-methylpiperidin-4-yl)-1H-indol-5-yl)urea Beginning with 15.0 mg 0.0655 mMol) 5-amino-3-(1-methyl-piperidin-4-yl)-1H-indole and 14.56 mg (0.0852 mMol) ethyl 2-isocyanato-3-methylbutyrate, 25.0 mg (95%) of the title compound were recovered.

MS(m/e): 401($M^+$)

EXAMPLE 60

N-(4-fluoro)phenyl-N'-(3-(1-methylpiperidin-4-yl)-1H-indol-5-yl)urea

Beginning with 15.0 mg 0.0655 mMol) 5-amino-3-(1-methyl-piperidin-4-yl)-1H-indole and 9.9 mg (0.072 mMol) 4-fluorophenyl isocyanate, 20.7 mg (86%) of the title compound were recovered.

MS(m/e): 367 ($M^+$)

EXAMPLE 61

N-(4-chloro)phenyl-N'-(3-(1-methylpiperidin-4-yl)-1H-indol-5-yl)urea

Beginning with 15.0 mg 0.0655 mMol 5-amino-3-(1-methyl-piperidin-4-yl)-1H-indole and 11.0 mg (0.072 mMol) 4-chlorophenyl isocyanate, 21.4 mg (86%) of the title compound were recovered.

MS(m/e): 383($M^+$)

EXAMPLE 62

N-(4-methyl)phenyl-N'-(3-(1-methylpiperidin-4-yl)-1H-indol-5-yl)urea

Beginning with 15.0 mg 0.0655 mMol) 5-amino-3-(1-methyl-piperidin-4-yl)-1H-indole and 9.6 mg (0.072 mMol) 4-methylphenyl isocyanate, 23.7 mg (99%) of the title compound were recovered.

MS(m/e): 363($M^+$)

EXAMPLE 63

N-(3-trifluoromethyl)phenyl-N'-(3-(1-methylpiperidin-4-yl)-1H-indol-5-yl)urea Beginning with 15.0 mg 0.0655 mMol) 5-amino-3-(1-methyl-piperidin-4-yl)-1H-indole and 16.0 mg (0.0852 mMol) 3-trifluoromethylphenyl isocyanate, 26.0 mg (95%) of the title compound were recovered.

MS(m/e): 417($M^+$)

EXAMPLE 64

N-(4-methoxy)phenyl-N'-(3-(1-methylpiperidin-4-yl)-1H-indol-5-yl)urea

Beginning with 15.0 mg 0.0655 mMol) 5-amino-3-(1-methyl-piperidin-4-yl)-1H-indole and 10.7 mg (0.072 mMol) 4-methoxyphenyl isocyanate, 22.4 mg (91%) of the title compound were recovered.

MS(m/e): 379($M^+$)

EXAMPLE 65

N-(2-methoxy)phenyl-N'-(3-(1-methylpiperidin-4-yl)-1H-indol-5-yl)urea

Beginning with 15.0 mg 0.0655 mMol 5-amino-3-(1-methyl-piperidin-4-yl)-1H-indole and 10.7 mg (0.072 mMol) 2-methoxyphenyl isocyanate, 21.7 mg (88%) of the title compound were recovered.

MS(m/e): 379(M⁺)

EXAMPLE 66

N-(4-methylthio)phenyl-N'-(3-(1-methylpiperidin-4-yl)-1H-indol-5-yl)urea

Beginning with 15.0 mg (0.0655 mMol) 5-amino-3-(1-methyl-piperidin-4-yl)-1H-indole and 14.05 mg (0.0852 mMol) 4-methylthiophenyl isocyanate, 24.1 mg (93%) of the title compound were recovered.

MS(m/e): 395(M⁺)

EXAMPLE 67

N-(3-acetyl)phenyl-N'-(3-(1-methylpiperidin-4-yl)-1H-indol-5-yl)urea

Beginning with 15.0 mg (0.0655 mMol) 5-amino-3-(1-methyl-piperidin-4-yl)-1H-indole and 13.7 mg (0.0852 mMol) 3-acetylphenyl isocyanate, 25.0 mg (98%) of the title compound were recovered.

MS(m/e): 391(M⁺)

EXAMPLE 68

N-(4-butoxycarbonyl)phenyl-N'-(3-(1-methylpiperidin-4-yl)-1H-indol-5-yl)urea

Beginning with 15.0 mg (0.0655 mMol) 5-amino-3-(1-methyl-piperidin-4-yl)-1H-indole and 15.8 mg (0.072 mMol) 4-carbobutoxyphenyl isocyanate, 27.1 mg (92%) of the title compound were recovered.

MS(m/e): 449(M⁺)

EXAMPLE 69

N-(2-phenyl)phenyl-N'-(3-(1-methylpiperidin-4-yl)-1H-indol-5-yl)urea

Beginning with 15.0 mg (0.0655 mMol 5-amino-3-(1-methyl-piperidin-4-yl)-1H-indole and 16.6 mg (0. 0852 mMol) 2-phenylphenyl isocyanate, 26.7 mg (96%) of the title compound were recovered.

MS(m/e): 425 (M⁺)

EXAMPLE 70

N-(4-phenyl)phenyl-N'-(3-(1-methylpiperidin-4-yl)-1H-indol-5-yl)urea

Beginning with 15.0 mg (0.0655 mMol) 5-amino-3-(1-methyl-piperidin-4-yl)-1H-indole and 16.6 mg (0.0852 mMol) 4-phenylphenyl isocyanate, 26.2 mg (95%) of the title compound were recovered.

MS(m/e): 425(M⁺)

EXAMPLE 71

N-(2,3-dichloro)phenyl-N'-(3-(1-methylpiperidin-4-yl)-1H-indol-5-yl)urea

Beginning with 15.0 mg (0.0655 mMol) 5-amino-3-(1-methyl-piperidin-4-yl)-1H-indole and 16.0 mg (0.0852 mMol) 2,3-dichlorophenyl isocyanate, 26.7 mg (98%) of the title compound were recovered.

MS(m/e): 417(M⁺)

EXAMPLE 72

N-benzyl-N'-(3-(1-methylpiperidin-4-yl)-1H-indol-5-yl)urea

Beginning with 15.0 mg (0.0655 mMol) 5-amino-3-(1-methyl-piperidin-4-yl)-1H-indole and 11.32 mg (0.0852 mMol) benzyl isocyanate, 9.4 mg of the title compound were recovered.

MS(m/e): 363(M⁺)

EXAMPLE 73

N-phenethyl-N'-(3-(1-methylpiperidin-4-yl)-1H-indol-5-yl)urea

Beginning with 15.0 mg (0.0655 mMol) 5-amino-3-(1-methyl-piperidin-4-yl)-1H-indole and 12.51 mg (0.0852 mMol) 2-phenethyl isocyanate, 15.8 mg (65%) of the title compound were recovered.

MS(m/e): 377(M⁺)

EXAMPLE 74

N-(α-methylbenzyl)-N'-(3-(1-methylpiperidin-4-yl)-1H-indol-5-yl)urea

Beginning with 15.0 mg (0.0655 mMol 5-amino-3-(1-methyl-piperidin-4-yl)-1H-indole and 12.51 mg (0.0852 mMol) α-methylbenzyl isocyanate, 24.0 mg (97%) of the title compound were recovered.

MS(m/e): 377(M⁺)

EXAMPLE 75

N-(β-(ethoxycarbonyl)phenethyl)-N'-(3-(1-methylpiperidin-4-yl)-1H-indol-5-yl)urea Beginning with 15.0 mg (0.0655 mMol) 5-amino-3-(1-methyl-piperidin-4-yl)-1H-indole and 16.6 mg (0.0852 mMol) ethyl 2-isocyanato-3-phenylpropionate , 28.0 mg (95%) of the title compound were recovered.

MS(m/e): 449(M⁺)

The compounds of Examples 76–79 were prepared at about 50° C. by the procedure described in detail in Example 42.

EXAMPLE 76

N,N-dimethyl-N'-(3-(1-methylpiperidin-4-yl)-1H-indol-5-yl)urea

Beginning with 13.0 mg (0.056 mMol) 5-amino-3-(1-methyl-piperidin-4-yl)-1H-indole and 6.4 mg (0.059 mMol) dimethyl carbamoyl chloride, 13.2 mg (79%) of the title compound were recovered.

MS(m/e): 301(M⁺)

EXAMPLE 77

N,N-diethyl-N'-(3-(1-methylpiperidin-4-yl)-1H-indol-5-yl)urea

Beginning with 13.0 mg (0.056 mMol) 5-amino-3-(1-methyl-piperidin-4-yl)-1H-indole and 8.0 mg (0.062 mMol) diethyl carbamoyl chloride, 16.05 mg (86%) of the title compound were recovered.

MS(m/e): 329(M⁺)

EXAMPLE 78

N-methyl-N-phenyl-N'-(3-(1-methylpiperidin-4-yl)-1H-indol-5-yl)urea

Beginning with 13.0 mg (0.056 mMol) 5-amino-3-(1-methyl-piperidin-4-yl)-1H-indole and 10.1 mg (0.059 mMol) N-methyl-N-phenyl carbamoyl chloride, 17.4 (86%) of the title compound were recovered.

MS (m/e): 363 (M⁺)

EXAMPLE 79

5-(morpholin-1yl)carbonylamino-3-(1-methylpiperidin-4-yl)-1H-indole

Beginning with 13.0 mg (0.056 mMol) 5-amino-3-(1-methyl-piperidin-4-yl)-1H-indole and 8.9 mg (0.059 mMol) morpholine-1-carbonyl chloride, 16.2 (85%) of the title compound were recovered.

MS(m/e): 343(M⁺)

The compounds of Examples 80–86 were prepared by the procedure described in detail in Example 53.

EXAMPLE 80

N-methyl-N'-3-(1-methylpiperidin-4-yl)-1H-indol-5-yl) thiourea

Beginning with 15.0 mg (0.0655 mMol) 5-amino-3-(1-methyl-piperidin-4-yl)-1H-indole and 9.56 mg (0.098 mMol) methyl isothiocyanate, 17.0 mg (86%) of the title compound were recovered.

MS (m/e): 303 (M⁺)

EXAMPLE 81

N-phenyl-N'-(3-(1-methylpiperidin-4-yl)-1H-indol-5-yl)thiourea

Beginning with 15.0 mg (0.0655 mMol) 5-amino-3-(1-methyl-piperidin-4-yl)-1H-indole and 13.26 mg (0.098 mMol) phenyl isothiocyanate, 16.8 mg (71%) of the title compound were recovered.

MS(m/e): 365(M⁺)

EXAMPLE 82

N-(4-methoxy)phenyl-N'-(3-(1-methylpiperidin-4-yl)-1H-indol-5-yl)thiourea

Beginning with 15.0 mg (0.0655 mMol) 5-amino-3-(1-methyl-piperidin-4-yl)-1H-indole and 16.21 mg (0.098 mMol) 4-methoxyphenyl isothiocyanate, 18.4 mg (71%) of the title compound were recovered.

MS(m/e): 395(M⁺)

EXAMPLE 83

N-(3-trifluoromethyl)phenyl-N'-(3-(1-methylpiperidin-4-yl)-1H-indol-5-yl) thiourea Beginning with 15.0 mg (0.0655 mMol) 5-amino-3-(1-methyl-piperidin-4-yl)-1H-indole and 19.94 mg (0.098 mMol) 3-trifluoromethylphenyl isothiocyanate, 15.6 mg (55%) of the title compound were recovered.

MS (m/e): 433 (M⁺)

EXAMPLE 84

N-(2-phenyl)phenyl-N'-(3-(1-methylpiperidin-4-yl)-1H-indol-5-yl)thiourea

Beginning with 15.0 mg (0.0655 mMol) 5-amino-3-(1-methyl-piperidin-4-yl)-1H-indole and 20.73 mg (0.098 mMol) 2-biphenyl isothiocyanate, 21.2 mg (74%) of the title compound were recovered.

MS(m/e): 441(M⁺)

EXAMPLE 85

N-(2,3-dichloro)phenyl-N'-(3-(1-methylpiperidin-4-yl)-1H-indol-5-yl)thiourea Beginning with 15.0 mg (0.0655 mMol) 5-amino-3-(1-methyl-piperidin-4-yl)-1H-indole and 20.04 mg (0.098 mMol) 2,3-dichlorophenyl isothiocyanate, 17.7 mg (62%) of the title compound were recovered.

MS(m/e): 433(M⁺)

EXAMPLE 86

N-benzyl-N'-(3-(1-methylpiperidin-4-yl)-1H-indol-5-yl)thiourea

Beginning with 15.0 mg (0.0655 mMol) 5-amino-3-(1-methyl-piperidin-4-yl)-1H-indole and 14.63 mg (0.098 mMol) benzyl isothiocyanate, 17.0 mg (86%) of the title compound were recovered.

MS(m/e): 379(M⁺)

EXAMPLE 87

5-phthalimido-3-(1-methylpiperidin-4-yl)-1H-indole oxalate

To a solution of 0.458 gm (2.0 mMol) 5-amino-3-(1-methylpiperidin-4-yl)-1H-indole in 8.0 mL dichloromethane were added 0.438 gm (2.0 mMol) N-carbethoxyphthalimide. The reaction mixture was stirred 18 hours at ambient temperature, at which time the solvent was removed under reduced pressure. The residue was subjected to flash chromatography, eluting with 100:20:0.5 dichloromethane:methanol:ammonium hydroxide, giving 0.467 gm (65%) of 5-phthalimido-3-(1-methylpiperidin-4-yl)-1H-indole as a yellow foam. The yellow foam was dissolved in a mixture of methanol:ethyl acetate and to it was added an equivalent of oxalic acid. The colorless precipitate which formed was recrystallized from methanol to give 0.267 gm of the title compound as colorless crystals.

m.p.=224° C.

MS(m/e): 359(M⁺)

Calculated for $C_{22}H_{21}N_3O_2 \cdot C_2H_2O_4$: Theory: C, 64.13; H, 5.16; N, 9.35. Found: C, 63.88; H, 5.27; N, 9.51.

EXAMPLE 88

5-(acetyl)amino-3-(1-methyl-1,2,3,6-tetrahydropyridin-4-yl)-1H-indole

To a solution of 1.0 gm (4.4 mMol) 5-amino-3-(1-methyl-1,2,3,6-tetrahydropyridin-4-yl)-1H-indole in 60 mL tetrahydrofuran were added 0.67 mL (4.8 mMol) triethylamine and the solution was cooled to 0° C. To this solution were then added 0.32 mL (4.6 mMol) acetyl chloride and the reaction mixture was stirred at ambient temperature for 18 hours. The reaction mixture was filtered and concentrated under reduced pressure to give a dark oil. The oil was treated with water to give a black gum. This residue was purified by radial chromatography (2 mm, silica), eluting with 100:10:1 dichloromethane:methanol:ammonium hydroxide, to give 0.20 gm (16.9%) of the title compound as a yellow solid.

m.p.=186–189° C.

MS(m/e): 269(M⁺)

Calculated for $C_{16}H_{19}N_3O$: Theory: C, 71.35; H, 7.11; N, 15.60. Found: C, 71.18; H, 6.97; N, 15.46.

The compounds of Examples 89–110 are prepared by the procedure described in detail in Example 88.

EXAMPLE 89

5-(propanoyl)amino-3-(1-methyl-1,2,3,6-tetrahydropyridin-4-yl)-1H-indole fumarate Beginning with 1.0 gm (4.4 mMol) 5-amino-3-(1-methyl-1,2,3,6-tetrahydropyridin-4-yl)-1H-indole and 0.74 mL (5.3 mMol) propanoyl chloride, 0.287 gm (23%) of the title compound were recovered as a red powder.
m.p.=170°–173° C.
MS(m/e): 283(M⁺)
Calculated for $C_{17}H_{21}N_3O \cdot C_4H_4O_4$: Theory: C, 63.15; H, 6.31; N, 10.52. Found: C, 62.97; H, 6.04; N, 10.66.

EXAMPLE 90

5-(benzoyl)amino-3-(1-methyl-1,2,3,6-tetrahydropyridin-4-yl)-1H-indole

Beginning with 1.13 gm (5.0 mMol) 5-amino-3-(1-methyl-1,2,3,6-tetrahydropyridin-4-yl)-1H-indole and 0.58 mL (5.0 mMol) benzoyl chloride, 0.477 gm (28.9%) of the title compound were recovered as a light green solid.
m.p.>250° C.
MS(m/e): 331(M⁺)
Calculated for $C_{21}H_{21}N_3O$: Theory: C, 76.11; H, 6.39; N, 12.68. Found: C, 75.84; H, 6.22; N, 12.41.

EXAMPLE 91

5-(4-chlorobenzoyl)amino-3-(1-methyl-1,2,3,6-tetrahydropyridin-4-yl)-1H-indole

Beginning with 1.13 gm (5.0 mMol) 5-amino-3-(1-methyl-1,2,3,6-tetrahydropyridin-4-yl)-1H-indole and 0.64 mL (5.0 mMol) 4-chlorobenzoyl chloride, 0.544 gm (29.9%) of the title compound were recovered as a tan solid.
m.p.=224°–226° C.
MS(m/e): 365(M⁺)
Calculated for $C_{21}H_{20}N_3OCl$: Theory: C, 68.94; H, 5.51; N, 11.48. Found: C, 68.75; H, 5.65; N, 11.63.

EXAMPLE 92

5-(4-methoxybenzoyl)amino-3-(1-methyl-1,2,3,6-tetrahydropyridin-4-yl)-1H-indole

Beginning with 1.13 gm (5.0 mMol) 5-amino-3-(1-methyl-1,2,3,6-tetrahydropyridin-4-yl)-1H-indole and 0.853 gm (5.0 mMol) 4-methoxybenzoyl chloride, 0.367 gm (20.4%) of the title compound were recovered as a light yellow solid.
m.p.=232° C. (dec.)
MS(m/e): 361(M⁺)
Calculated for $C_{22}H_{23}N_3O_2$: Theory: C, 73.11; H, 6.41; N, 11.63. Found: C, 72.86; H, 6.39; N, 11.33.

EXAMPLE 93

5-(2-chloro-4-fluorobenzoyl)amino-3-(1-methyl-1,2,3,6-tetrahydropyridin-4-yl)-1H-indole Beginning with 2.0 gm (8.8 mMol) 5-amino-3-(1-methyl-1,2,3,6-tetrahydropyridin-4-yl)-1H-indole and 1.9 gm (9.7 mMol) 2-chloro-4-fluorobenzoyl chloride, 0.67 gm (19.8%) of the title compound were recovered as a light yellow solid.
m.p.=212°–222° C.
MS(m/e): 383(M⁺)
Calculated for $C_{21}H_{19}N_3OClF$: Theory: C, 65.71; H, 4.99; N, 10.95. Found: C, 66.00; H, 5.10; N, 10.84.

EXAMPLE 94

5-(4-fluorobenzoyl)amino-3-(1-ethyl-1,2,3,6-tetrahydropyridin-4-yl)-1H-indole

Beginning with 2.69 gm (11.1 mMol) 5-amino-3-(1-ethyl-1,2,3,6-tetrahydropyridin-4-yl)-1H-indole and 1.45 mL (12.3 mMol) 4-fluorobenzoyl chloride, 2.39 gm (59.0%) of the title compound were recovered as a burnt orange powder.
m.p.=127°–135° C. (dec.)
MS(m/e): 363(M⁺)
Calculated for $C_{22}H_{22}N_3OF$: Theory: C, 72.71; H, 6.10; N, 11.56. Found: C, 72.42; H, 6.14; N, 11.33.

EXAMPLE 95

5-(2-furoyl)amino-3-(1-methyl-1,2,3,6-tetrahydropyridin-4-yl)-1H-indole

Beginning with 1.13 gm (5.0 mMol) 5-amino-3-(1-methyl-1,2,3,6-tetrahydropyridin-4-yl)-1H-indole and 0.52 mL (5.0 mMol) 2-furoyl chloride, 0.129 gm (8.1%) of the title compound were recovered as a tan solid.
m.p.=190° C. (dec.)
MS(m/e): 321(M⁺)
Calculated for $C_{19}H_{19}N_3O_2$: Theory: C, 71.01; H, 5.96; N, 13.08. Found: C, 71.26; H, 6.17; N, 12.85.

EXAMPLE 96

5-(2-thienoyl)amino-3-(1-methyl-1,2,3,6-tetrahydropyridin-4-yl)-1H-indole

Beginning with 1.0 gm (4.4 mMol) 5-amino-3-(1-methyl-1,2,3,6-tetrahydropyridin-4-yl)-1H-indole and 0.494 mL (4.6 mMol) 2-thiophenecarbonyl chloride, 0.489 gm (33.0%) of the title compound were recovered as a bright yellow solid.
m.p.=229°–233° C. (dec.)
MS(m/e): 337(M⁺)
Calculated for $C_{19}H_{19}N_3OS$: Theory: C, 67.63; H, 5.67; N, 12.45. Found: C, 67.44; H, 5.70; N, 12.22.

EXAMPLE 97

5-(acetyl)amino-3-(1-methylpiperidin-4-yl)-1H-indole

Beginning with 2.00 gm (5.74 mMol) 5-amino-3-(1-methyl-piperidin-4-yl)-1H-indole dihydrochloride ethanolate and 1.13 gm (25.8 mMol) acetyl chloride, 1.22 gm (78.3%) of the title compound were recovered as a white powder.
m.p.=161°–165° C. (dec.)
MS(m/e): 271(M⁺)
Calculated for $C_{16}H_{21}N_3O$: Theory: C, 70.82; H, 7.80; N, 15.48. Found: C, 70.52; H, 7.83; N, 15.37.

EXAMPLE 98

5-(propanoyl)amino-3-(1-methylpiperidin-4-yl)-1H-indole fumarate

Beginning with 0.945 gm (4.12 mMol) 5-amino-3-(1-methyl-piperidin-4-yl)-1H-indole and 0.689 mL (4.94 mMol) propanoyl chloride, 1.3 gm (81.2%) of the title compound were recovered as a tan solid.
m.p.=88°–92° C. (dec.)
MS(m/e): 285(M⁺)
Calculated for $C_{17}H_{23}N_3O \cdot C_4H_4O_4$: Theory: C, 62.83; H, 6.78; N, 10.47. Found: C, 62.61; H, 6.84; N, 10.25.

EXAMPLE 99

5-(trimethylacetyl)amino-3-(1-methylpiperidin-4-yl)-1H-indole

Beginning with 2.00 gm (5.74 mMol) 5-amino-3-(1-methyl-piperidin-4-yl)-1H-indole dihydrochloride ethanolate and 1.78 gm (14.4 mMol) trimethylacetyl chloride, 0.623 gm (34.6%) of the title compound were recovered as an off-white powder.

m.p.=214°–216° C. (dec.)

MS(m/e): 313(M⁺)

Calculated for $C_{19}H_{27}N_3O$: Theory: C, 72.81; H, 8.68; N, 13.41. Found: C, 72.56; H, 8.73; N, 13.28.

EXAMPLE 100

5-(benzoyl)amino-3-(1-methylpiperidin-4-yl)-1H-indole oxalate

Beginning with 0.545 gm (2.4 mMol) 5-amino-3-(1-methyl-piperidin-4-yl)-1H-indole and 0.398 mL (2.85 mMol) benzoyl chloride, 0.92 gm (90.5%) of the title compound were recovered as an off-white solid.

m.p.=130° C.

MS(m/e): 333(M⁺)

Calculated for $C_{21}H_{23}N_3O \cdot C_2H_2O_4$: Theory: C, 65.24; H, 5.95; N, 9.92. Found: C, 64.98; H, 6.12; N, 9.84.

EXAMPLE 101

5-(4-fluorobenzoyl)amino-3-(1-methylpiperidin-4-yl)-1H-indole fumarate

Beginning with 15.2 gm (66 mMol) 5-amino-3-(1-methyl-piperidin-4-yl)-1H-indole and 7.8 mL (66 mMol) 4-fluorobenzoyl chloride, 13.01 gm (42.2%) of the title compound were recovered as an off-white solid.

m.p.=139°–140° C. (dec.)

MS(m/e): 351(M⁺)

Calculated for $C_{21}H_{22}N_3OF \cdot C_4H_4O_4$: Theory: C, 64.23; H, 5.61; N, 8.99. Found: C, 63.96; H, 5.65; N, 9.05.

EXAMPLE 102

5-(2-chlorobenzoyl)amino-3-(1-methylpiperidin-4-yl)-1H-indole fumarate

Beginning with 1.14 gm (5.0 mMol) 5-amino-3-(1-methyl-piperidin-4-yl)-1H-indole and 0.63 mL (5.0 mMol) 2-chlorobenzoyl chloride, 0.406 gm (16.8%) of the title compound were recovered as colorless crystals.

m.p.=209° C. (dec.)

MS(m/e): 367(M⁺)

Exact Mass: Theory: 368.1530. Found: 368.1531.

EXAMPLE 103

5-(3-chlorobenzoyl)amino-3-(1-methylpiperidin-4-yl)-1H-indole fumarate

Beginning with 1.14 gm (5.0 mMol) 5-amino-3-(1-methyl-piperidin-4-yl)-1H-indole and 0.62 mL (5.0 mMol) 3-chlorobenzoyl chloride, 0.942 gm (38.9%) of the title compound were recovered as a colorless solid.

m.p.=185° C. (dec.)

MS(m/e): 367(M⁺)

Calculated for $C_{21}H_{22}N_3OCl \cdot C_4H_4O_4$: Theory: C, 62.05; H, 5.41; N, 8.68. Found: C, 61.77; H, 5.60; N, 8.61.

EXAMPLE 104

5-(4-chlorobenzoyl)amino-3-(1-methylpiperidin-4-yl)-1H-indole fumarate

Beginning with 1.14 gm (5.0 mMol) 5-amino-3-(1-methyl-piperidin-4-yl)-1H-indole and 0.64 mL (5.0 mMol) 4-chlorobenzoyl chloride, 0.339 gm (14.0%) of the title compound were recovered as a colorless solid.

m.p.=163° C. (dec.)

MS(m/e): 367(M⁺)

Calculated for $C_{21}H_{22}N_3OCl \cdot C_4H_4O_4$: Theory: C, 62.05; H, 5.42; N, 8.68. Found: C, 61.92; H, 5.47; N, 8.52.

EXAMPLE 105

5-(2-methoxybenzoyl)amino-3-(1-methylpiperidin-4-yl)-1H-indole fumarate

Beginning with 1.14 gm (5.0 mMol) 5-amino-3-(1-methyl-piperidin-4-yl)-1H-indole and 0.74 mL (5.0 mMol) 2-methoxybenzoyl chloride, 0.569 gm (23.7%) of the title compound were recovered as an off-white solid.

m.p.=90° C. (dec.)

MS(m/e): 364(M⁺)

Exact Mass: Theory: 364.2025. Found: 364.2029.

EXAMPLE 106

5-(3-methoxybenzoyl)amino-3-(1-methylpiperidin-4-yl)-1H-indole fumarate

Beginning with 1.14 gm (5.0 mMol) 5-amino-3-(1-methyl-piperidin-4-yl)-1H-indole and 0.70 mL (5.0 mMol) 3-methoxybenzoyl chloride, 0.653 gm (27.2%) of the title compound were recovered as an off-white solid.

m.p.=152° C. (dec.)

MS(m/e): 364(M⁺)

Calculated for $C_{22}H_{25}N_3O_2 \cdot C_4H_4O_4$: Theory: C, 65.12; H, 6.10; N, 8.76. Found: C, 64.85; H, 6.38; N, 8.48.

EXAMPLE 107

5-(4-methoxybenzoyl)amino-3-(1-methylpiperidin-4-yl)-1H-indole fumarate

Beginning with 1.14 gm (5.0 mMol) 5-amino-3-(1-methyl-piperidin-4-yl)-1H-indole and 0.853 gm (5.0 mMol) 4-methoxybenzoyl chloride, 0.398 gm (16.6%) of the title compound were recovered as an off-white solid.

m.p.=151° C. (dec.)

MS(m/e): 364(M⁺)

Exact Mass: Theory: 364.2025. Found: 364.2032.

EXAMPLE 108

5-(2-furoyl)amino-3-(1-methylpiperidin-4-yl)-1H-indole fumarate

Beginning with 1.14 gm (5.0 mMol) 5-amino-3-(1-methyl-piperidin-4-yl)-1H-indole and 0.52 mL (5.0 mMol) 2-furoyl chloride, 0.420 gm (19.1%) of the title compound were recovered as an off-white solid.

m.p.=114° C. (dec.)

MS(m/e): 324(M⁺)

Calculated for $C_{19}H_{21}N_3O_2 \cdot C_4H_4O_4$: Theory: C, 62.86; H, 5.73; N, 9.56. Found: C, 63.15; H, 5.89; N, 9.84.

EXAMPLE 109

5-(2-thienoyl)amino-3-(1-methylpiperidin-4-yl)-1H-indole oxalate

Beginning with 0.72 gm (3.14 mMol) 5-amino-3-(1-methyl-piperidin-4-yl)-1H-indole and 0.525 mL (3.8 mMol)

2-thienoyl chloride, 1.2 gm of the title compound were recovered as an off-white solid.

m.p.=135° C. (dec.)

MS(m/e): 339(M⁺)

Calculated for $C_{19}H_{21}N_3OS \cdot C_2H_2O_4$: Theory: C, 58.61; H, 5.54; N, 9.64. Found: C, 58.90; H, 5.41; N, 9.89.

EXAMPLE 110

5-(phenylacetyl)amino-3-(1-methylpiperidin-4-yl)-1H-indole oxalate

Beginning with 2.00 gm (5.74 mMol) 5-amino-3-(1-methyl-piperidin-4-yl)-1H-indole dihydrochloride ethanolate and 2.23 gm (14.4 mMol) phenylacetyl chloride, 0.80 gm of the title compound were recovered as a tan solid.

m.p.<90° C.

MS(m/e): 347(M⁺)

Calculated for $C_{22}H_{25}N_3O \cdot C_2H_2O_4$: Theory: C, 65.89; H, 6.22; N, 9.60. Found: C, 65.68; H, 6.29; N, 9.83.

EXAMPLE 111

5-(fur-2-oyl amino-3-(1-methyl-1,2,3,6-tetrahydropyridin-4-yl)-1H-indole

A. Preparation of 5-(2-furoyl)amino-1H-indole

To a solution of 2.09 gm (15.8 mMol) 5-amino-1H-indole in 20 mL tetrahydrofuran were added 2.6 mL (18.97 mMol) triethylamine and the solution was cooled in an ice bath. To the reaction mixture were then added dropwise 1.71 ml (17.4 mMol) 2-furoyl chloride. When this addition was complete the cooling bath was removed and the reaction mixture was stirred 1.5 hours at ambient temperature. At this point the reaction was diluted with water and extracted well with ethyl acetate. The organic solutions were combined and washed sequentially with water, 2N sodium hydroxide, water and saturated aqueous sodium chloride. The remaining organics were then dried over sodium sulfate and concentrated under reduced pressure to give a dark purple solid. The solid was subjected to flash chromatography, eluting with a gradient of dichloromethane containing 0–2% methanol. The recovered solid was crystallized from ethyl acetate to give 1.8 gm (50.3%) of 5-(2-furoyl)amino-1H-indole as pale purple crystals.

m.p.=181°–182° C.

MS(m/e): 227(M+1)

Calculated for $C_{13}H_{10}N_2O_2$: Theory: C, 69.02; H, 4.46; N, 12.38. Found: C, 68.79; H, 4.52; N, 12.25.

B. Condensation of substituted indole with 1-ethyl-4-piperidone

To a solution of 0.868 gm (15.5 mMol) potassium hydroxide in 8 mL methanol were added 1.0 gm (4.42 mMol) 5-(2-furoyl)amino-1H-indole and 0.774 mL 1-ethyl-4-piperidone and the solution was stirred at reflux for 18 hours. The reaction mixture was cooled to ambient and then diluted with ice/water. The resultant precipitate was collected and dried under vacuum. This solid was purified by radial chromatography (2 mm silica), eluting with a gradient of dichloromethane containing 5–7.5% methanol and 0.5–1.0% ammonium hydroxide. The product was then crystallized from ethyl acetate to give 0.715 gm (48.3%) of the title compound as a bright yellow powder.

m.p.=120°–122° C.

MS(m/e): 336(M+1)

Calculated for $C_{20}H_{21}N_3O_2$: Theory: C, 71.62; H, 6.31; N, 12.53. Found: C, 71.51; H, 6.33; N, 12.73.

EXAMPLE 112

5-(2-furoyl)amino-3-(1-ethylpiperidin-4-yl)-1H-indole

To a solution of 0.780 gm (3.2 mMol) 5-amino-3-(1-ethylpiperidin-4-yl)-1H-indole in 10 mL tetrahydrofuran and 10 mL dimethylformamide were added 0.536 mL (3.85 mMol) triethylamine followed by the dropwise addition of 0.348 mL (3.5 mMol) 2-furoyl chloride. After 18 hours the reaction mixture was cooled in an ice bath. The reaction mixture was the partitioned between 100 mL ethyl acetate and 100 mL 2N sodium hydroxide. The phases were separated and the aqueous extracted again with ethyl acetate. Organic extracts were combined and washed sequentially with 2N sodium hydroxide, water and saturated aqueous sodium chloride. The remaining organics were dried over sodium sulfate and concentrated under reduced pressure. The residue was subjected to radial chromatography (2 mm silica), eluting with 100:10:1 dichloromethane:methanol:ammonium hydroxide. Fractions containing product were combined and concentrated under reduced pressure. The residue was crystallized from ethyl acetate/hexane to give 0.789 gm (73.1%) of the title compound as an off-white solid.

m.p.=178°–179° C.

MS(m/e): 338(M+1)

Calculated for $C_{20}H_{23}N_3O_2$: Theory: C, 71.19; H, 6.87; N, 12.45. Found: C, 71.44; H, 7.09; N, 12.40.

EXAMPLE 113

5-(4-fluorobenzoyl)amino-3-(1-ethylpiperidin-4-yl)-1H-indole fumarate

Following the procedure described in detail in Example 32, 1.14 gm (3.14 mMol) 5-(4-fluorobenzoyl)amino-3-(1-ethyl-1,2,3,6-tetrahydropyridin-4-yl)-1H-indole were hydrogenated to give 0.527 gm (34.8%) of the title compound as a tan powder.

m.p.=152°–155° C.

MS(m/e): 366(M+1)

Calculated for $C_{22}H_{24}N_3OF \cdot C_4H_4O_4$: Theory: C, 64.85; H, 5.86; N, 8.73. Found: C, 65.15; H, 5.95; N, 8.95.

EXAMPLE 114

5-(2-chloro-4-fluorobenzoyl)amino-3-(1-methylpiperidin-4-yl)-1H-indole

To a solution of 0.40 gm (1.04 mMol) 5-(2-chloro-4-fluorobenzoyl)amino-3-(1-methyl-1,2,3,6-tetrahydropyridin-4-yl)-1H-indole in 5.2 mL trifluoroacetic acid were added 0.208 mL (1.3 mMol) triethylsilane and the reaction mixture was stirred at ambient. After 2 hours, the reaction mixture was concentrated under reduced pressure. To the residue was added 2N sodium hydroxide and the aqueous was extracted with dichloromethane. The combined organic extracts were washed with 2N sodium hydroxide, dried over sodium sulfate and then concentrated under reduced pressure to give an orange foam. The foam was subjected to radial chromatography (2 mm silica), eluting with 100:10:1 dichloromethane:methanol: ammonium hydroxide. The residue was crystallized from ethyl acetate/ hexanes to give 0.27 gm (67.3%) of the title compound as a burnt orange powder.

MS(m/e): 385(M+)

The compounds of Examples 115–124 were prepared by the procedure described in detail in Example 42.

EXAMPLE 115

5-(methoxyacetyl)amino-3-(1-methylpiperidin-4-yl)-1H-indole

Beginning with 13 mg (0.056 mMol) 5-amino-3-(1-methylpiperidin-4-yl)-1H-indole and 6.5 mg (0.059 mMol) methoxyacetyl chloride, 14.2 mg (84%) of the title compound were recovered.

MS(m/e): 302(M$^+$)

EXAMPLE 116

5-((2-thienyl)acetyl)amino-3-(1-methylpiperidin-4-yl)-1H-indole

Beginning with 13 mg (0.056 mMol) 5-amino-3-(1-methylpiperidin-4-yl)-1H-indole and 9.6 mg (0.059 mMol) (2-thiophene)acetyl chloride, 14.1 mg (72%) of the title compound were recovered.

MS(m/e): 354(M$^+$)

EXAMPLE 117

5-(3-(methoxycarbonyl)propanoyl)amino-3-(1-methylpiperidin-4-yl)-1H-indole

Beginning with 13 mg (0.056 mMol) 5-amino-3-(1-methylpiperidin-4-yl)-1H-indole and 9.0 mg (0.059 mMol) (3-methoxy-carbonyl)propanoyl chloride, 14.1 mg (75%) of the title compound were recovered.

MS(m/e): 344(M$^+$)

EXAMPLE 118

5-(2-fluorobenzoyl)amino-3-(1-methylpiperidin-4-yl)-1H-indole

Beginning with 10 mg (0.0437 mMol) 5-amino-3-(1-methyl-piperidin-4-yl)-1H-indole and 5.4 μL (0.0458 mMol) 2-fluorobenzoyl chloride, 12.2 mg (80%) of the title compound were recovered.

MS(m/e): 351(M$^+$)

EXAMPLE 119

5-(2-methylbenzoyl)amino-3-(1-methylpiperidin-4-yl)-1H-indole

Beginning with 10 mg (0.0437 mMol) 5-amino-3-(1-methyl-piperidin-4-yl)-1H-indole and 6.0 μL (0.0458 mMol) 2-methylbenzoyl chloride, 14.3 mg (95%) of the title compound were recovered.

MS(m/e): 348(M+1)

EXAMPLE 120

5-(3-methylbenzoyl)amino-3-(1-methylpiperidin-4-yl)-1H-indole

Beginning with 13 mg (0.056 mMol) 5-amino-3-(1-methylpiperidin-4-yl)-1H-indole and 9.2 mg (0.059 mMol) 3-methylbenzoyl chloride, 17.1 mg (88%) of the title compound were recovered.

MS(m/e): 348(M$^+$)

EXAMPLE 121

5-(2-trifluoromethylbenzoyl)amino-3-(1-methylpiperidin-4-yl)-1H-indole

Beginning with 13 mg (0.056 mMol) 5-amino-3-(1-methylpiperidin-4-yl)-1H-indole and 13.0 mg (0.062 mMol) 2-trifluoromethylbenzoyl chloride, 20.3 mg 89%) of the title compound were recovered.

MS(m/e): 401(M$^+$)

EXAMPLE 122

5-(3,4-dichlorobenzoyl)amino-3-(1-methylpiperidin-4-yl)-1H-indole

Beginning with 10 mg (0.0437 mMol) 5-amino-3-(1-methyl-piperidin-4-yl)-1H-indole and 9.6 mg (0.0458 mMol) 3,4-dichlorobenzoyl chloride, 14.4 mg (82%) of the title compound were recovered.

MS(m/e): 401(M$^+$)

EXAMPLE 123

5-(2,4-dichlorobenzoyl)amino-3-(1-methylpiperidin-4-yl)-1H-indole

Beginning with 10 mg (0.0437 mMol) 5-amino-3-(1-methyl-piperidin-4-yl)-1H-indole and 6.4 μL (0.0458 mMol) 2,4-dichlorobenzoyl chloride, 12.2 mg (80%) of the title compound were recovered.

MS(m/e): 401(M$^+$)

EXAMPLE 124

5-(isoxazol-5-oyl)amino-3-(1-methylpiperidin-4-yl)-1H-indole

Beginning with 13 mg (0.056 mMol) 5-amino-3-(1-methylpiperidin-4-yl)-1H-indole and 8.21 mg (0.062 mMol) isoxazole-5-carbonyl chloride, 10.4 mg (57%) of the title compound were recovered.

MS(m/e): 325(M$^+$)

EXAMPLE 125

Alternate Synthesis of 5-(2-thienoyl)amino-3-(1-methylpiperidin-4-yl)-1H-indole oxalate To a solution of 0.615 gm (4.8 mMol) 2-thienoic acid in 10 mL dichloromethane were added 0.778 gm (4.8 mMol) N,N-carbonyldiimidazole in 2 mL dichloromethane. After 1.5 hour, a solution of 1.0 gm (4.4 mMol) 5-amino-3-(1-methylpiperidin-4-yl)-1H-indole in 15 mL dichloromethane was added and the reaction mixture stirred for 18 hours at ambient. The reaction mixture was washed sequentially with 1N sodium hydroxide, water and saturated aqueous sodium chloride. The remaining organics were dried over sodium sulfate and the volatiles removed under reduced pressure. The residual brown foam was subjected to radial chromatography (2 mm silica), eluting with a gradient of dichloromethane containing 5–7.5% methanol and 0.5% ammonium hydroxide. Fractions shown to contain product were combined and concentrated under reduced pressure. This material was dissolved in ethyl acetate/ethanol and was treated with oxalic acid to give 0.20 gm (10.7%) of the title compound as a tan solid.

m.p.=160° C.

MS(m/e): 339(M$^+$)

Calculated for $C_{19}H_{21}N_3OS.C_2H_2O_4$: Theory: C, 58.73; H, 5.40; N, 9.78. Found: C, 58.61; H, 5.54; N, 9.64.

General Procedure for the coupling of carboxylic acids with 5-amino-3-(1-methylpiperidin-4-yl)-1H-indole To a suspension of 4–5 equivalents of polymer bound 1-ethyl-3-(3-dimethylaminopropyl)carbodiimide (Desai, et al., *Tetrahedron Letters*, 34(48), 7685 (1993)) in chloroform are added 1 equivalent of 5-amino-3-(1-methylpiperidin-4-yl)-1H-indole and 2–3 equivalents of the carboxylic acid. The reaction is agitated until the reaction is complete, heat may be applied if necessary. The resin is removed by filtration and the product isolated by evaporation of solvent. This procedure is illustrated by Examples 126–178.

EXAMPLE 126

5-(1-propanoyl)amino-3-(1-methylpiperidin-4-yl)-1H-indole

Beginning with 12.0 mg (0.05 mMol) 5-amino-3-(1-methylpiperidin-4-yl)-1H-indole and 8 μL (0.1 mMol) 1-propanoic acid, 13.0 mg (91%) of the title compound were recovered.

MS(m/e): 286(M+1)

EXAMPLE 127

5-(2-methylpropanoyl)amino-3-(1-methylpiperidin-4-yl)-1H-indole

Beginning with 12.0 mg (0.05 mMol) 5-amino-3-(1-methylpiperidin-4-yl)-1H-indole and 8.8 mg (0.10 mMol) isobutyric acid, 11.8 mg (79%) of the title compound were recovered.

MS(m/e): 300(M+1)

EXAMPLE 128

5-(3-methylbutanoyl)amino-3-(1-methylpiperidin-4-yl)-1H-indole

Beginning with 12.0 mg (0.05 mMol) 5-amino-3-(1-methylpiperidin-4-yl)-1H-indole and 10.0 mg (0.10 mMol) isovaleric acid, 17.0 mg (100+%) of the title compound were recovered.

MS(m/e): 314(M$^+$)

EXAMPLE 129

5-(1-pentanoyl)amino-3-(1-methylpiperidin-4-yl)-1H-indole

Beginning with 12.0 mg (0.05 mMol) 5-amino-3-(1-methylpiperidin-4-yl)-1H-indole and 10.0 mg (0.10 mMol) pentanoic acid, 12.8 mg (82%) of the title compound were recovered.

MS(m/e): 314(M+1)

EXAMPLE 130

5-(ethoxyacetyl)amino-3-(1-methylpiperidin-4-yl)-1H-indole

Beginning with 12.0 mg (0.05 mMol) 5-amino-3-(1-methylpiperidin-4-yl)-1H-indole and 11.0 μL (0.10 mMol) ethoxyacetic acid, 15.2 mg (97%) of the title compound were recovered.

MS(m/e): 316(M+1)

EXAMPLE 131

5-(phenoxyacetyl)amino-3-(1-methylpiperidin-4-yl)-1H-indole

Beginning with 12.0 mg (0.05 mMol) 5-amino-3-(1-methylpiperidin-4-yl)-1H-indole and 15.0 mg (0.10 mMol) phenxoyacetic acid, 9.4 mg (52%) of the title compound were recovered.

MS(m/e): 364(M+1)

EXAMPLE 132

5-(diphenylacetyl)amino-3-(1-methylpiperidin-4-yl)-1H-indole

Beginning with 12.0 mg (0.05 mMol) 5-amino-3-(1-methylpiperidin-4-yl)-1H-indole and 21.0 mg (0.10 mMol) diphenylacetic acid, 14.0 mg (66%) of the title compound were recovered.

MS(m/e): 424(M+1)

EXAMPLE 133

5-(cinnamoyl)amino-3-(1-methylpiperidin-4-yl)-1H-indole

Beginning with 12.0 mg (0.05 mMol) 5-amino-3-(1-methylpiperidin-4-yl)-1H-indole and 15.0 mg (0.10 mMol) cinnamic acid, 7.2 mg (40%) of the title compound were recovered.

MS(m/e): 360(M+1)

EXAMPLE 134

5-(cyclopropanecarbonyl)amino-3-(1-methylpiperidin-4-yl)-1H-indole

Beginning with 12.0 mg (0.05 mMol) 5-amino-3-(1-methylpiperidin-4-yl)-1H-indole and 9.0 μL (0.10 mMol) cyclopropanecarboxylic acid, 11.4 mg (77%) of the title compound were recovered.

MS(m/e): 298(M+1)

EXAMPLE 135

5-(cyclobutanecarbonyl)amino-3-(1-methylpiperidin-4-yl)-1H-indole

Beginning with 12.0 mg (0.05 mMol) 5-amino-3-(1-methylpiperidin-4-yl)-1H-indole and 15.0 mg (0.10 mMol) cyclobutanecarboxylic acid, 15.0 mg (96%) of the title compound were recovered.

MS(m/e): 312(M+1)

EXAMPLE 136

5-(cyclopentanecarbonyl)amino-3-(1-methylpiperidin-4-yl)-1H-indole

Beginning with 12.0 mg (0.05 mMol) 5-amino-3-(1-methylpiperidin-4-yl)-1H-indole and 11.0 mg (0.10 mMol) cyclopentanecarboxylic acid, 16.4 mg (100+%) of the title compound were recovered.

MS(m/e): 326(M+1)

EXAMPLE 137

5-(cyclohexanecarbonyl)amino-3-(1-methylpiperidin-4-yl)-1H-indole

Beginning with 12.0 mg (0.05 mMol) 5-amino-3-(1-methylpiperidin-4-yl)-1H-indole and 13.0 mg (0.10 mMol) cyclohexanecarboxylic acid, 20.6 mg (100+%) of the title compound were recovered.

MS(m/e): 340 (M+1)

EXAMPLE 138

5-(1,2,3,4-tetrahydronaphth-1-oyl)amino-3-(1-methylpiperidin-4-yl)-1H-indole

Beginning with 12.0 mg (0.05 mMol) 5-amino-3-(1-methylpiperidin-4-yl)-1H-indole with 16.2 mg (0.10 mMol)

1,2,3,4-tetrahydro-1-naphthoic acid at 70° C., 16.2 mg (84%) of the title compound were recovered.

MS(m/e): 388(M+1)

EXAMPLE 139

5-(3-fluorobenzoyl)amino-3-(1-methylpiperidin-4-yl)-1H-indole

Beginning with 12.0 mg (0.05 mMol) 5-amino-3-(1-methylpiperidin-4-yl)-1H-indole and 21.0 mg (0.15 mMol) 3-fluorobenzoic acid, 11.8 mg (67%) of the title compound were recovered.

MS(m/e): 352(M+1)

EXAMPLE 140

5-(4-bromobenzoyl)amino-3-(1-methylpiperidin-4-yl)-1H-indole

Beginning with 20.0 mg (0.087 mMol) 5-amino-3-(1-methylpiperidin-4-yl)-1H-indole and 52.0 mg (0.131 mMol) 4-bromobenzoic acid, 27.3 mg (75.8%) of the title compound were recovered.

MS(m/e): 413(M$^+$)

EXAMPLE 141

5-(4-iodobenzoyl)amino-3-(1-methylpiperidin-4-yl)-1H-indole

Beginning with 10.0 mg (0.044 mMol) 5-amino-3-(1-methylpiperidin-4-yl)-1H-indole and 32.0 mg (0.131 mMol) 4-iodobenzoic acid, 12.0 mg (60%) of the title compound were recovered.

MS(m/e): 459(M$^+$)

EXAMPLE 142

5-(3-iodobenzoyl)amino-3-(1-methylpiperidin-4-yl)-1H-indole

Beginning with 10.0 mg (0.044 mMol) 5-amino-3-(1-methylpiperidin-4-yl)-1H-indole and 32.0 mg (0.131 mMol) 3-iodobenzoic acid, 15.9 mg (80%) of the title compound were recovered.

MS(m/e): 459(M$^+$)

EXAMPLE 143

5-(4-methylbenzoyl)amino-3-(1-methylpiperidin-4-yl)-1H-indole

Reacting 12.0 mg (0.05 mMol) 5-amino-3-(1-methylpiperidin-4-yl)-1H-indole with 14.0 mg (0.10 mMol) 4-methylbenzoic acid at 70° C., 12.0 mg (69%) of the title compound were recovered.

MS(m/e): 348(M+1)

EXAMPLE 144

5-(4-hexyloxybenzoyl)amino-3-(1-methylpiperidin-4-yl)-1H-indole

Beginning with 10.0 mg (0.044 mMol) 5-amino-3-(1-methylpiperidin-4-yl)-1H-indole and 30.0 mg (0.131 mMol) 4-hexyloxybenzoic acid, 16.8 mg (89%) of the title compound were recovered.

MS(m/e): 434(M+1)

EXAMPLE 145

5-(4-trifluoromethylbenzoyl)amino-3-(1-methylpiperidin-4-yl)-1H-indole

Beginning with 12.0 mg (0.05 mMol) 5-amino-3-(1-methylpiperidin-4-yl)-1H-indole and 29.0 mg (0.15 mMol) 4-trifluoromethylbenzoic acid, 11.6 mg (58%) of the title compound were recovered.

MS(m/e): 402(M+1)

EXAMPLE 146

5-(3-trifluoromethylbenzoyl)amino-3-(1-methylpiperidin-4-yl)-1H-indole

Beginning with 7.0 mg (0.03 mMol) 5-amino-3-(1-methylpiperidin-4-yl)-1H-indole and 17.1 mg (0.09 mMol) 3-trifluoromethylbenzoic acid, 8.7 mg (72%) of the title compound were recovered.

MS(m/e): 403(M+2)

EXAMPLE 147

5-(4-cyanobenzoyl)amino-3-(1-methylpiperidin-4-yl)-1H-indole

Beginning with 20.0 mg (0.087 mMol) 5-amino-3-(1-methylpiperidin-4-yl)-1H-indole and 38.0 mg (0.131 mMol) 4-cyanobenzoic acid, 13.5 mg (43.1%) of the title compound were recovered.

MS(m/e): 359(M+1)

EXAMPLE 148

5-(4-nitrobenzoyl)amino-3-(1-methylpiperidin-4-yl)-1H-indole

Beginning with 20.0 mg (0.087 mMol) 5-amino-3-(1-methylpiperidin-4-yl)-1H-indole and 44.0 mg (0.131 mMol) 4-nitrobenzoic acid, 13.8 mg (41.8%) of the title compound were recovered.

MS(m/e): 379(M+1)

EXAMPLE 149

5-(4-(methylthio)benzoyl)amino-3-(1-methylpiperidin-4-yl)-1H-indole

Beginning with 20.0 mg (0.087 mMol) 5-amino-3-(1-methylpiperidin-4-yl)-1H-indole and 44.0 mg (0.131 mMol) 4-(methylthio)benzoic acid, 18.9 mg (57.1%) of the title compound were recovered.

MS(m/e): 380(M+1)

EXAMPLE 150

5-(3-(dimethylamino)benzoyl)amino-3-(1-methylpiperidin-4-yl)-1H-indole

Reacting 12.0 mg (0.05 mMol) 5-amino-3-(1-methylpiperidin-4-yl)-1H-indole with 17.0 mg (0.10 mMol) 3-(dimethylamino)benzoic acid at 70° C., 12.4 mg (66%) of the title compound were recovered.

MS(m/e): 377(M+1)

EXAMPLE 151

5-(4-phenylbenzoyl)amino-3-(1-methylpiperidin-4-yl)-1H-indole

Reacting 12.0 mg (0.05 mMol) 5-amino-3-(1-methylpiperidin-4-yl)-1H-indole with 20.0 mg (0.10 mMol) 4-phenylbenzoic acid at 70° C., 10.0 mg (49%) of the title compound were recovered.

MS(m/e): 410(M+1)

EXAMPLE 152

5-(4-(acetyl)benzoyl)amino-3-(1-methylpiperidin-4-yl)-1H-indole

Beginning with 20.0 mg (0.087 mMol) 5-amino-3-(1-methylpiperidin-4-yl)-1H-indole and 44.0 mg (0.131 mMol)

4-(acetyl)benzoic acid, 16.5 mg (50.5%) of the title compound were recovered.

MS(m/e): 376(M+1)

EXAMPLE 153

5-(4-(benzoyl)benzoyl)amino-3-(1-methylpiperidin-4-yl)-1H-indole

Beginning with 10.0 mg (0.044 mMol) 5-amino-3-(1-methylpiperidin-4-yl)-1H-indole and 30.0 mg (0.131 mMol) 4-(benzoyl)benzoic acid, 14.4 mg (75%) of the title compound were recovered.

MS(m/e): 438(M+1)

EXAMPLE 154

5-(4-(methanesulfonyl)benzoyl)amino-3-(1-methylpiperidin-4-yl)-1H-indole

Beginning with 7.0 mg (0.03 mMol) 5-amino-3-(1-methylpiperidin-4-yl)-1H-indole and 18.0 mg (0.09 mMol) 4-(methanesulfonyl)benzoic acid, 7.2 mg of the title compound were recovered.

MS(m/e): 411(M$^+$)

EXAMPLE 155

5-(3,5-dichlorobenzoyl)amino-3-(1-methylpiperidin-4-yl)-1H-indole

Beginning with 7.0 mg (0.03 mMol) 5-amino-3-(1-methylpiperidin-4-yl)-1H-indole and 17.2 mg (0.09 mMol) 3,5-dichlorobenzoic acid, 10.3 mg of the title compound were recovered.

MS(m/e): 402(M$^+$)

EXAMPLE 156

5-(3,4-dimethylbenzoyl)amino-3-(1-methylpiperidin-4-yl)-1H-indole

Beginning with 10.0 mg (0.044 mMol) 5-amino-3-(1-methylpiperidin-4-yl)-1H-indole and 19.6 mg (0.131 mMol) 3,4-dimethylbenzoic acid, 12.0 mg (76%) of the title compound were recovered.

MS(m/e): 362(M+1)

EXAMPLE 157

5-(3,5-dimethylbenzoyl)amino-3-(1-methylpiperidin-4-yl)-1H-indole

Beginning with 10.0 mg (0.044 mMol) 5-amino-3-(1-methylpiperidin-4-yl)-1H-indole and 19.6 mg (0.131 mMol) 3,5-dimethylbenzoic acid, 15.0 mg (95%) of the title compound were recovered.

MS(m/e): 362(M+1)

EXAMPLE 158

5-(2,3-dimethoxybenzoyl)amino-3-(1-methylpiperidin-4-yl)-1H-indole

Beginning with 7.0 mg (0.03 mMol) 5-amino-3-(1-methylpiperidin-4-yl)-1H-indole and 16.4 mg (0.09 mMol) 2,3-dimethoxybenzoic acid, 11.4 mg (97%) of the title compound were recovered.

MS(m/e): 394(M+1)

EXAMPLE 159

5-(3-nitro-4-chlorobenzoyl)amino-3-(1-methylpiperidin-4-yl)-1H-indole

Beginning with 10.0 mg (0.044 mMol) 5-amino-3-(1-methylpiperidin-4-yl)-1H-indole and 26.4 mg (0.131 mMol) 3-nitro-4-chlorobenzoic acid, 11.4 mg (63.3%) of the title compound were recovered.

MS(m/e): 412(M$^+$)

EXAMPLE 160

5-(3,4,5-trimethoxybenzoyl)amino-3-(1-methylpiperidin-4-yl)-1H-indole

Beginning with 10.0 mg (0.044 mMol) 5-amino-3-(1-methylpiperidin-4-yl)-1H-indole and 27.8 mg (0.131 mMol) 3,4,5-trimethoxybenzoic acid, 13.8 mg (75%) of the title compound were recovered.

MS(m/e): 424(M+1)

EXAMPLE 161

5-(3,5-(di-t-butyl)-4-hydroxybenzoyl)amino-3-(1-methylpiperidin-4-yl)-1H-indole

Beginning with 10.0 mg (0.044 mMol) 5-amino-3-(1-methylpiperidin-4-yl)-1H-indole and 32.8 mg (0.131 mMol) 3,5-di(t-butyl)-4-hydroxybenzoic acid, 15.0 mg (75%) of the title compound were recovered.

MS(m/e): 462(M+1)

EXAMPLE 162

5-(pyridine-2-carbonyl)amino-3-(1-methylpiperidin-4-yl)-1H-indole

Beginning with 12.0 mg (0.05 mMol) 5-amino-3-(1-methylpiperidin-4-yl)-1H-indole and 19.0 mg (0.15 mMol pyridine-2-carboxylic acid, 14.2 mg (85%) of the title compound were recovered.

MS(m/e): 335(M+1)

EXAMPLE 163

5-(pyridine-3-carbonyl)amino-3-(1-methylpiperidin-4-yl)-1H-indole

Beginning with 7.0 mg (0.03 mMol) 5-amino-3-(1-methylpiperidin-4-yl)-1H-indole and 11.1 mg (0.09 mMol pyridine-3-carboxylic acid, 7.4 mg of the title compound were recovered.

MS(m/e): 335(M+1)

EXAMPLE 164

5-(pyridine-4-carbonyl)amino-3-(1-methylpiperidin-4-yl)-1H-indole

Beginning with 7.0 mg (0.03 mMol) 5-amino-3-(1-methylpiperidin-4-yl)-1H-indole and 11.1 mg (0.09 mMol) pyridine-4-carboxylic acid, 7.0 mg of the title compound were recovered.

MS(m/e): 335(M+1)

EXAMPLE 165

5-(6-chloropyridine-3-carbonyl)amino-3-(1-methylpiperidin-4-yl)-1H-indole

Beginning with 7.0 mg (0.03 mMol) 5-amino-3-(1-methylpiperidin-4-yl)-1H-indole and 14.2 mg (0.09 mMol) 6-chloropyridine-3-carboxylic acid, 4.4 mg (40%) of the title compound were recovered.

MS(m/e): 369(M+1)

EXAMPLE 166

5-(2-quinolinoyl amino-3-(1-methylpiperidin-4-yl)-1H-indole

Beginning with 12.0 mg (0.05 mMol) 5-amino-3-(1-methylpiperidin-4-yl)-1H-indole and 17.0 mg (0.10 mMol) 2-quinaldic acid, 17.6 mg (92%) of the title compound were recovered.

MS(m/e): 385(M+1)

EXAMPLE 167

5-(pyrazine-2-carbonyl)amino-3-(1-methylpiperidin-4-yl)-1H-indole

Beginning with 20.0 mg (0.087 mMol) 5-amino-3-(1-methylpiperidin-4-yl)-1H-indole and 32 mg (0.131 mMol) pyrazine-2-carboxylic acid, 6.9 mg (24%) of the title compound were recovered.

MS(m/e): 336(M+1)

EXAMPLE 168

5-(2-pyrroyl)amino-3-(1-methylpiperidin-4-yl)-1H-indole

Beginning with 10.0 mg (0.044 mMol) 5-amino-3-(1-methylpiperidin-4-yl)-1H-indole and 21.1 mg (0.131 mMol) pyrrole-2-carboxylic acid, 12.6 mg (78%) of the title compound were recovered.

MS(m/e): 323(M+1)

EXAMPLE 169

5-(N-methyl-2-pyrroyl)amino-3-(1-methylpiperidin-4-yl)-1H-indole

Beginning with 12.0 mg (0.05 mMol) 5-amino-3-(1-methylpiperidin-4-yl)-1H-indole and 19.0 mg (0.15 mMol) N-methylpyrrole-2-carboxylic acid, 18.0 mg (100%) of the title compound were recovered.

MS(m/e): 337(M+1)

EXAMPLE 170

5-(2-methyl-3-furoyl)amino-3-(1-methylpiperidin-4-yl)-1H-indole

Beginning with 7.0 mg (0.03 mMol) 5-amino-3-(1-methylpiperidin-4-yl)-1H-indole and 11.3 mg (0.09 mMol) 2-methyl-3-furoic acid, 0.4 mg (4%) of the title compound were recovered.

MS(m/e): 338(M+1)

EXAMPLE 171

5-(3-furoyl)amino-3-(1-methylpiperidin-4-yl)-1H-indole

Beginning with 12.0 mg (0.05 mMol) 5-amino-3-(1-methylpiperidin-4-yl)-1H-indole and 17.0 mg (0.15 mMol) 3-furoic acid, 13.8 mg (85%) of the title compound were recovered.

MS(m/e): 324(M+1)

EXAMPLE 172

5-(5-methyl-2-furoyl)amino-3-(1-methylpiperidin-4-yl)-1H-indole

Beginning with 7.0 mg (0.03 mMol) 5-amino-3-(1-methylpiperidin-4-yl)-1H-indole and 11.3 mg (0.09 mMol) 5-methyl-2-furoic acid, 8.8 mg (87%) of the title compound were recovered.

MS(m/e): 338(M+1)

EXAMPLE 173

5-(5-bromo-2-furoyl)amino-3-(1-methylpiperidin-4-yl)-1H-indole

Beginning with 10.0 mg (0.044 mMol) 5-amino-3-(1-methylpiperidin-4-yl)-1H-indole and 25.0 mg (0.131 mMol) 5-bromo-2-furoic acid, 8.4 mg (48%) of the title compound were recovered.

MS(m/e): 403(M$^+$)

EXAMPLE 174

5-(benzofuran-2-carbonyl)amino-3-(1-methylpiperidin-4-yl)-1H-indole

Beginning with 12.0 mg (0.05 mMol) 5-amino-3-(1-methylpiperidin-4-yl)-1H-indole and 24.0 mg (0.15 mMol) benzofuran-2-carboxylic acid, 15.6 mg (84%) of the title compound were recovered.

MS(m/e): 374(M+1)

EXAMPLE 175

5-(3-thienoyl)amino-3-(1-methylpiperidin-4-yl)-1H-indole

Beginning with 7.0 mg (0.03 mMol) 5-amino-3-(1-methylpiperidin-4-yl)-1H-indole and 11.5 mg (0.09 mMol) 3-thienoic acid, 9.4 mg (92%) of the title compound were recovered.

MS(m/e): 340(M+1)

EXAMPLE 176

5-(3-methyl-2-thienoyl)amino-3-(1-methylpiperidin-4-yl)-1H-indole

Beginning with 7.0 mg (0.03 mMol) 5-amino-3-(1-methylpiperidin-4-yl)-1H-indole and 12.8 mg (0.09 mMol) 3-methyl-2-thienoic acid, 9.6 mg (90%) of the title compound were recovered.

MS(m/e): 354(M+1)

EXAMPLE 177

5-(5-methyl-2-thienoyl)amino-3-(1-methylpiperidin-4-yl)-1H-indole

Beginning with 12.0 mg (0.05 mMol) 5-amino-3-(1-methylpiperidin-4-yl)-1H-indole and 21.0 mg (0.10 mMol) 5-methyl-2-thienoic acid, 13.0 mg (74%) of the title compound were recovered.

MS(m/e): 354(M+1)

EXAMPLE 178

5-(4-methoxy-3-thienoyl)amino-3-(1-methylpiperidin-4-yl)-1H-indole

Beginning with 7.0 mg (0.03 mMol) 5-amino-3-(1-methylpiperidin-4-yl)-1H-indole and 14.2 mg (0.09 mMol 4-methoxy-3-thienoic acid, 12.1 mg of the title compound were recovered.

MS(m/e): 369(M$^+$)

EXAMPLE 179

5-(1-naphthoyl)amino-3-(1-methylpiperidin-4-yl)-1H-indole hydrochloride

To a suspension of 1.2 gm (5.2 mMol) 5-amino-3-(1-methylpiperidin-4-yl)-1H-indole in 50 mL tetrahydrofuran were added 0.946 mL (6.3 mMol) 1-naphthoyl chloride dropwise. After 18 hours the reaction mixture was filtered. The recovered filtrate was dissolved in 10 mL dimethylformamide to which were added 1.5 mL (10.5 mMol) triethylamine followed by 0.8 mL (5.3 mMol) 1-naphthoyl chloride. After 18 hours the reaction mixture was partitioned between ethyl acetate and 1N sodium hydroxide. The phases were separated and the aqueous extracted again with ethyl acetate. The combined ethyl acetate extracts were then washed sequentially with 1N sodium hydroxide, water and saturated aqueous sodium chloride. The remaining organics were dried over sodium sulfate and concentrated under reduced pressure. The residue was subjected to flash chromatography, eluting with 100:10:1 dichloromethane:methanol:ammonium hydroxide. Fractions shown to contain product were combined and concentrated under reduced pressure. The residue was taken up in ethanol and treated with ethanolic hydrogen chloride. The solution was concentrated under reduced pressure and the residue crystallized from ethylacetate/ethanol to give 1.28 gm (58.2%) of the title compound as a tan powder.

m.p.=193°–203° C.

MS(m/e): 384(M+1)

Calculated for $C_{25}H_{25}N_3O \cdot HCl \cdot 0.3\ CH_3CO_2CH_2CH_3$: Theory: C, 70.50; H, 6.41; N, 9.41; Cl, 7.94. Found: C, 70.10; H, 6.41; N, 9.41; Cl, 8.34.

EXAMPLE 180

5-(2-naphthoyl)amino-3-(1-methylpiperidin-4-yl)-1H-indole

To a solution of 0.989 gm (4.31 mMol) 5-amino-3-(1-methylpiperidin-4-yl)-1H-indole in 20 mL tetrahydrofuran and 10 mL dimethylformamide were added 0.721 mL (5.2 mMol) triethylamine followed by 0.904 gm (4.74 mMol) 2-naphthoyl chloride. After 18 hours the reaction mixture was cooled in an ice bath and then diluted with 100 mL ethyl acetate followed by 50 mL 2N sodium hydroxide. The phases were separated and the aqueous extracted with ethyl acetate. The organic extracts were combined then washed sequentially with 2N sodium hydroxide, water and saturated aqueous sodium chloride. The remaining organics were dried over sodium sulfate and concentrated under reduced pressure. The residue was subjected to flash chromatography, eluting with 100:10:1 dichloromethane:methanol:ammonium hydroxide. Fractions shown to contain product were combined and concentrated under reduced pressure. The residue was precipitated from ethyl acetate/hexane to give 1.355 gm (82.1%) of the title compound as a tan powder.

m.p.=153°–155.5° C.

MS(m/e): 383(M$^+$)

Calculated for $C_{25}H_{25}N_3O$: Theory: C, 78.30; H, 6.57; N, 10.96. Found: C, 78.24; H, 6.63; N, 11.10.

EXAMPLE 181

Alternate Synthesis of 5-(2-chloro-4-fluorobenzoyl)amino-3-(1-methylpiperidin-4-yl)-1H-indole To a suspension of 0.804 gm (3.5 mMol) 5-amino-3-(1-methylpiperidin-4-yl)-1H-indole in 10 mL tetrahydrofuran and 5.0 mL dimethylformamide were added 0.586 mL (4.2 mMol) triethylamine followed by a solution of 0.744 gm (3.86 mMol) 2-chloro-4-fluorobenzoyl chloride in 5 mL tetrahydrofuran. After 18 hours the reaction mixture was diluted with ethyl acetate followed by 2N sodium hydroxide. The phases were separated and the aqueous extracted with ethyl acetate. The organic extracts were combined then washed sequentially with 2N sodium hydroxide, water and saturated aqueous sodium chloride. The remaining organics were dried over sodium sulfate and concentrated under reduced pressure. The residue was subjected to flash chromatography, eluting with 100:10:1 dichloromethane:methanol:ammonium hydroxide. Fractions shown to contain product were combined and concentrated under reduced pressure. The residue was precipitated from ethyl acetate to give 0.921 gm (68.2%) of the title compound as a light pink powder.

m.p.=159°–162° C.

MS(m/e): 385(M$^+$)

Calculated for $C_{21}H_{21}N_3OClF$: Theory: C, 65.37; H, 5.49; N, 10.89. Found: C, 65.15; H, 5.55; N, 10.74.

EXAMPLE 182

Alternate Synthesis of 5-(4-fluorobenzoyl)amino-3-(1-methylpiperidin-4-yl)-1H-indole fumarate A. Preparation of 5-(4-flurobenzoyl)amino-1H-indole To a solution of 3.96 gm (30.0 mMol) 5-amino-1H-indole in 150 mL tetrahydrofuran were added 5.6 mL triethylamine followed by a solution of 5.2 gm (33.0 mMol) 4-fluorobenzoyl chloride in 30 mL tetrahydrofuran. After 18 hours the reaction mixture was poured into water, made basic with sodium hydroxide solution, and extracted with dichloromethane. The organic extracts were combined, dried over sodium sulfate and concentrated under reduced pressure to give a purple solid. This residue was recrystallized from ethyl acetate/hexane to give 6.37 gm (84%) 5-(4-fluoro-benzoyl)amino-1H-indole as brown crystals in two crops.

m.p.=205°–207° C.

MS(m/e): 254(M$^+$)

Calculated for $C_{15}H_{11}N_2OF$: Theory: C, 70.86; H, 4.36; N, 11.02. Found: C, 70.64; H, 4.43; N, 10.73.

B. Preparation of 5-(4-fluorobenzolyl)amino-3-(1-methyl-1,2,3,6-tetrahydropyridin-4-yl)-1H-indole A solution of 2.54 gm (10 mMol) 5-(4-fluorobenzoyl) amino-1H-indole and 1.7 gm (15.0 mMol) 1-methyl-4-piperidone in 20 mL 10% methanolic potassium hydroxide was heated to reflux for 3.5 hours and then allowed to stir without heating. After 18 hours the resultant suspension was filtered, the solid washed with methanol and then dried under reduced pressure to give 2.30 gm (65.8%) 5-(4-fluorobenzoyl)-amino-3-(1-methyl-1,2,3,6-tetrahydropyridin-4-yl)-1H-indole as a tan powder.

m.p.=187.5°–189.5° C.

MS(m/e): 349(M$^+$)

Calculated for $C_{21}H_{20}N_3OF$: Theory: C, 72.19; H, 5.77; N, 12.03. Found: C, 72.36; H, 5.87; N, 12.01.

C. Hydrogenation of 5-(4-fluorobenzoyl)amino-3-(1-methyl-1,2,3,6-tetrahydropyridin-4-yl)-1H-indole To a solution of 0.84 gm (2.4 mMol) 5-(4-fluorobenzoyl)-amino-3-(1-methyl-1,2,3,6-tetrahydropyridin-4-yl)-1H-indole in 100 mL methanol were added 0.25 gm 5% palladium on carbon and the mixture stirred under a hydrogen atmosphere maintained with a hydrogen filled balloon. After 15 hours the mixture was filtered and the filtrate concentrated under reduced pressure. The residual light yellow glass was then subjected to Florisil™ chromatography, eluting with 4:1 dichloromethane:methanol containing a trace of ammonium hydroxide. Fractions shown to contain product were combined and concentrated under reduced pressure. The residue was dissolved in ethyl acetate and this solution treated with a saturated solution of fumaric acid in methanol. The solvent was decanted from the precipitate which was recrystallized from ethyl acetate/methanol to give 0.377 gm (33.6%) of the title compound as colorless needles in two crops.

m.p.=155°–158° C. (dec.)

MS(m/e): 351(M⁺)

Calculated for $C_{21}H_{22}N_3OF \cdot C_4H_4O_4$: Theory: C, 64.23; H, 5.61; N, 8.99. Found: C, 64.50; H, 5.58; N, 8.78.

EXAMPLE 183

5-((4-fluorobenzoyl)-N-methyl)amino-3-(1,2,3,6-tetrahydropyridin-4-yl)-1H-indole fumarate To a solution of 0.59 gm (2.45 mMol) 5-methylamino-3-(1,2,3,6-tetrahydropyridin-4-yl)-1H-indole in 20 mL dimethylformamide were added 0.409 mL (2.9 mMol) triethylamine followed by 0.318 mL (2.7 mMol) 4-fluorobenzoyl chloride. After 3 hours the reaction mixture was diluted with 100 mL 2N sodium hydroxide followed by 100 mL ethyl acetate. The phases were separated and the aqueous extracted with ethyl acetate. The organic extracts were combined and washed sequentially with water and saturated aqueous sodium chloride. The remaining organics were dried over sodium sulfate and concentrated under reduced pressure. The residue was subjected to flash chromatography, eluting with a gradient of dichloromethane containing 0–5% methanol and 0–0.5% ammonium hydroxide. Fractions shown to contain product were combined and concentrated under reduced pressure. Fumarate salt was formed in and crystallized from ethyl acetate/ethanol to give 0.868 gm (73.9%) of the title compound as a tan powder.

m.p.=203°–206° C. (dec.)

MS(m/e): 363(M⁺)

Calculated for $C_{22}H_{22}N_3OF \cdot C_4H_4O_4$: Theory: C, 65.13; H, 5.47; N, 8.76. Found: C, 65.43; H, 5.73; N, 8.92.

EXAMPLE 184

5-(2-tetrahydrofuranoyl)-3-(1-ethylpiperidin-4-yl)-1H-indole oxalate

To a solution of 0.52 gm (1.55 mMol) 5-(2-furoyl)amino-3-(1-ethyl-1,2,3,6-tetrahydropyridin-4-yl)-1H-indole in 50 mL ethanol and 25 mL tetrahydrofuran were added 0.13 gm 5% palladium on carbon and the mixture hydrogenated at ambient temperature at an initial hydrogen pressure of 60 p.s.i. After 24 hours the reaction mixture was filtered and concentrated under reduced pressure. The residue was purified by radial chromatography (2 mm Silica), eluting with 100:5:1 dichloromethane:methanol:ammonium hydroxide. Fractions shown to contain product were combined and concentrated under reduced pressure. The residue was dissolved in ethyl acetate and treated with an equivalent of oxalic acid. The solid which formed was filtered, washed with ethyl acetate and dried under reduced pressure to give 0.32 gm (47.9%) of the title compound as a white powder.

m.p.=103°–105° C.

MS(m/e): 341(M⁺1)

Calculated for: $C_{20}H_{27}N_3O_2 \cdot C_2H_2O_4$: Theory: C, 61.24; H, 6.77; N, 9.74. Found: C, 61.42; H, 6.80; N, 9.65.

EXAMPLE 185

5-methanesulfonylamino-3-(1,2,3,6-pyridin-4-yl)-1H-indole hydrochloride

To a solution of 1.47 gm (26.2 mMol) potassium hydroxide in 10 mL methanol were added 1.0 gm (4.76 mMol) 5-methanesulfonylamino-1H-indole in 5 mL methanol followed by 1.1 gm (7.1 mMol) 4-piperidone hydrochloride monohydrate. The resulting suspension was stirred at reflux for 18 hours. The reaction mixture was then concentrated under reduced pressure. The residual oil was then dissolved in water and the pH of the solution adjusted to 8.0 with 5.0N hydrochloric acid. The solution was saturated with sodium chloride and then extracted with dichloromethane. The organic phases were combined and concentrated under reduced pressure. The residual solid was crystallized from methanol/water to give 0.815 gm (52.2%) of the title compound as yellow needles. m.p.>250° C.

MS(m/e): 291(M⁺)

Calculated for: $C_{14}H_{17}N_3SO_2$—HCl: Theory: C, 51.29; H, 5.53; N, 12.82. Found: C, 51.53; H, 5.55; N, 12.73.

EXAMPLE 186

5-(4-fluorobenzoyl)amino-3-(1,2,3,6-tetrahydropyridin-4-yl)-1H-indole

To a solution of 5.8 gm (90 mMol) potassium hydroxide in 75 mL methanol were added 9.22 gm (60 mMol) 4-piperidone hydrochloride monohydrate followed by 7.8 gm (30 mMol) 5-(4-fluorobenzoyl)amino-3-(piperidin-4-yl)-1H-indole (Example 182A). This solution was stirred at reflux for 18 hours. The reaction mixture was cooled to ambient and then poured slowly into 150 mL water, maintaining the temperature of the solution at about 20° C. The resulting precipitate was filtered and recrystallized from ethanol to give 4.72 gm (47.2%) of the title compound as tan crystals. 0.725 gm of the material were crystallized again from ethanol to provide 0.241 gm light yellow crystals for analysis.

m.p.=241° C. (dec.)

MS(m/e): 335(M⁺)

Calculated for: $C_{20}H_{18}N_3OF$: Theory: C, 71.63; H, 5.41; N, 12.53. Found: C, 71.85; H, 5.50; N, 12.61.

EXAMPLE 187

5-(4-fluorobenzoyl)amino-3-(piperidin-4-yl)-1H-indole

Following the procedure described in detail in Example 30, 3.93 gm (11.7 mMol) 5-(4-fluorobenzoyl)amino-3-(1,2,3,6-tetrahydropyridin-4-yl)-1H-indole were hydrogenated to give 1.83 gm (49%) of the title compound as colorless crystals.

m.p.=229°–230° C. (methanol)

MS(m/e): 337(M⁺)

Calculated for: $C_{20}H_{20}N_3OF$: Theory: C, 71.20; H, 5.98; N, 12.45. Found: C, 71.46; H, 6.17; N, 12.40.

General Procedure for the Coupling of Amines with Indole 5-carboxylic acids

A mixture of 15 mg (0.058 mMol) 5-carboxy-3-(1-methyl-1,2,5,6-tetrahydropyridin-4-yl)-1H-indole, 18 mg (0.088 mMol) dicyclohexylcabodiimide, 12 mg (0.088 mMol) hydroxybenztriazole, and 1.5 equivalents of an appropriate amine in 2 mL dimethylformamide are heated at 75° C. for 18 hours. The reaction is allowed to cool and is then loaded onto a VARIAN BOND ELUT SCX™ (Varian, Harbor City, Calif., U.S.A.) ion exchange column (3 mL/0.5 gm). The column is washed with 6 mL methanol and then the desired compound is stripped from the column by eluting with 2M ammonium hydroxide in methanol. This eluant is concentrated under reduced pressure and the residue dissolved in 2 mL dichloromethane. To this solution is added 0.118 gm (0.118 mMol) of a polystyrene bound isocyanate resin and the mixture agitated for 18 hours. The reaction mixture is filtered and concentrated under reduced pressure to provide the amides of the invention. If desired, the compound may be further purified by loading onto a VARIAN BOND ELUT SAX™ (Varian, Harbor City, Calif., U.S.A.) ion exchange column (10 mL/0.5 gm). The desired compound is stripped from the column by eluting with methanol and concentrating the eluant under reduced pressure. The compounds of Examples 188–202 were prepared by this procedure.

EXAMPLE 188

N-[(pyridin-2-yl)methyl]-5-carboxamido-3-(1-methyl-1,2,5,6-tetrahydropyridin-4-yl)-1H-indole Using 2-aminomethylpyridine, 5.2 mg (26%) of the title compound was recovered.
MS(m/e): 337(M+1)

EXAMPLE 189

N-[(pyridin-3-yl)methyl]-5-carboxamido-3-(1-methyl-1,2,5,6-tetrahydropyridin-4-yl)-1H-indole Using 3-aminomethylpyridine, 8.3 mg (42%) of the title compound was recovered.
MS(m/e): 337(M+1)

EXAMPLE 190

N-[(pyridin-4-yl)methyl]-5-carboxamido-3-(1-methyl-1,2,5,6-tetrahydropyridin-4-yl)-1H-indole Using 4-aminomethylpyridine, 7.9 mg (40%) of the title compound was recovered.
MS(m/e): 337(M+1)

EXAMPLE 191

N-[(fur-2-yl)methyl]-5-carboxamido-3-(1-methyl-1,2,5,6-tetrahydropyridin-4-yl)-1H-indole Using 2-aminomethylfuran, 8.0 mg (51%) of the title compound was recovered.
MS(m/e): 335(M$^+$)

EXAMPLE 192

N-[(tetrahydrofur-2-yl)methyl]-5-carboxamido-3-(1-methyl-1,2,5,6-tetrahydropyridin-4-yl)-1H-indole Using 2-aminomethyltetrahydrofuran, 3.8 mg (20%) of the title compound was recovered.
MS(m/e): 340(M+1)

EXAMPLE 193

5-(pyrrolidin-1yl)carbonyl-3-(1-methyl-1,2,5,6-tetrahydropyridin-4-yl)-1H-indole Using pyrrolidine, 7.1 mg (39%) of the title compound was recovered.
MS(m/e): 309(M$^+$)

EXAMPLE 194

5-(piperidin-1yl)carbonyl-3-(1-methyl-1,2,5,6-tetrahydropyridin-4-yl)-1H-indole

Using piperidine, 9.7 mg (51%) of the title compound was recovered.
MS(m/e): 323(M$^+$)

EXAMPLE 195

5-(morpholin-1yl)carbonyl-3-(1-methyl-1,2,5,6-tetrahydropyridin-4-yl)-1H-indole

Using morpholine, 7.2 mg (38%) of the title compound was recovered.
MS(m/e): 325(M$^+$)

EXAMPLE 196

5-(thiomorpholin-1yl)carbonyl-3-(1-methyl-1,2,5,6-tetrahydropyridin-4-yl)-1H-indole Using thiomorpholine, 11.2 mg (56%) of the title compound was recovered.
MS(m/e): 341(M$^+$)

EXAMPLE 197

5-(4-hydroxypiperidin-1yl)carbonyl-3-(1-methyl-1,2,5,6-tetrahydropyridin-4-yl)-1H-indole Using 4-hydroxypiperidine, 3.6 mg (18%) of the title compound was recovered.
MS(m/e): 340(M+1)

EXAMPLE 198

5-(3-hydroxymethylpiperidin-1yl)carbonyl-3-(1-methyl-1,2,5,6-tetrahydropyridin-4-yl)-1H-indole Using 3-hydroxymethylpiperidine, 10.1 mg (49%) of the title compound was recovered.
MS(m/e): 353(M$^+$)

EXAMPLE 199

5-(3-(N,N-diethylcarboxamido)piperidin-1yl) carbonyl-3-(1-methyl-1,2,5,6-tetrahydropyridin-4-yl)-1H-indole Using 3-(N,N-diethylcarboxamido)piperidine, 11.0 mg (44%) of the title compound was recovered.
MS(m/e): 422(M$^+$)

EXAMPLE 200

5-(4-cyclopentylpiperazin-1yl)carbonyl-3-(1-methyl-1,2,5,6-tetrahydropyridin-4-yl)-1H-indole Using 4-cyclopentylpiperazine, 8.7 mg (38%) of the title compound was recovered.
MS(m/e): 393(M+1)

EXAMPLE 201

5-(4-(2-methoxyethyl)piperazin-1yl)carbonyl-3-(1-methyl-1,2,5,6-tetrahydropyridin-4-yl)-1H-indole Using 4-(2-methoxyethyl)piperazine, 9.6 mg (43%) of the title compound was recovered.
MS(m/e): 383(M+1)

EXAMPLE 202

5-(4-(pyridin-2-yl)piperazin-1yl)carbonyl-3-(1-methyl-1,2,5,6-tetrahydropyridin-4-yl)-1H-indole Using 4-(pyridin-2-yl)piperazine, 8.6 mg (36%) of the title compound was recovered.
MS(m/e): 402(M+1)

To demonstrate the use of the compounds of this invention in the treatment of migraine, their ability to bind to the 5-HT$_{1F}$ receptor subtype was determined. The ability of the compounds of this invention to bind to the 5-HT$_{1F}$ receptor subtype was measured essentially as described in N. Adham, et al., *Proceedings of the National Academy of Sciences (USA)*, 90, 408–412 (1993).

Membrane Preparation: Membranes were prepared from transfected Ltk-cells which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40.000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford (*Anal. Biochem.*, 72, 248–254 (1976)).

Radioligand Bindina: [$^3$H-5-HT] binding was performed using slight modifications of the 5-HT$_{1D}$ assay conditions reported by Herrick-Davis and Titeler (*J. Neurochem.*, 50, 1624–1631 (1988)) with the omission of masking ligands. Radioligand binding studies were achieved at 37° C. in a total volume of 250 μL of buffer (50 mM Tris, 10 mM MgCl$_2$, 0.2 mM EDTA, 10 μM pargyline, 0.1% ascorbate, pH=7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 6–12 concentrations of compound. Incubation times were 30 minutes for both saturation and displacement studies based upon initial investigations which determined equilibrium binding conditions. Nonspecific binding was defined in the presence of 10 μM 5-HT. Binding was initiated by the addition of 50 μL membrane homogenates (10–20 μg). The reaction was terminated by rapid filtration through presoaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL ReadiSafe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio). IC$_{50}$ values were converted to K$_i$ values using the Cheng-Prusoff equation (*Biochem. Pharmacol.*, 22, 3099–3108 (1973). All experiments were performed in triplicate. Representative compounds of this invention were found to have affinity for the 5-HT$_{1F}$ receptor as measured by the procedure described supra.

As was reported by R. L. Wainshank, et al., WO$_{93/14201}$, the 5-HT$_{1F}$ receptor is functionally coupled to a G-protein as measured by the ability of serotonin and serotonergic drugs to inhibit forskolin stimulated cAMP production in NIH$_3$T3 cells transfected with the 5-HT$_{1F}$ receptor. Adenylate cyclase activity was determined using standard techniques. A maximal effect is achieved by serotonin. An Emax is determined by dividing the inhibition of a test compound by the maximal effect and determining a percent inhibition. (N. Adham, et al., supra,; R. L. Wainshank, et al., *Proceedings of the National Academy of Sciences (USA)*, 89,3630–3634 (1992)), and the references cited therein.

Measurement of cAMP formation

Transfected NIH3T3 cells (estimated Bmax from one point competition studies=488 fmol/mg of protein) were incubated in DMEM, 5 mM theophylline, 10 mM HEPES (4-[2-hydroxyethyl]-1-piperazineethanesulfonic acid) and 10 μM pargyline for 20 minutes at 37° C., 5% CO$_2$. Drug dose-effect curves were then conducted by adding 6 different final concentrations of drug, followed immediately by the addition of forskolin (10 μM). Subsequently, the cells were incubated for an additional 10 minutes at 37° C., 5% CO$_2$. The medium was aspirated and the reaction was stopped by the addition of 100 mM HCl. To demonstrate competitive antagonism, a dose-response curve for 5-HT was measured in parallel, using a fixed dose of methiothepin (0.32 The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software. All of the compounds shown to have affinity for the 5-HT$_{1F}$ receptor were tested and found to be agonists at the 5-HT$_{1F}$ receptor in the cAMP assay.

The discovery that the pain associated with migraine and associated disorders is inhibited by activation of the 5-HT$_{1F}$ receptor by administration of 5-HT$_{1F}$ agonists required the analysis of data from diverse assays of pharmacological activity. To establish that the 5-HT$_{1F}$ receptor subtype is responsible for mediating neurogenic meningeal extravasation which leads to the pain of migraine, the binding affinity of a panel of compounds to serotonin receptors was measured first, using standard procedures. For example, the ability of a compound to bind to the 5-HT$_{1F}$ receptor subtype was performed as described supra. For comparison purposes, the binding affinities of compounds to the 5-HT$_{1D\alpha}$, 5-HT$_{1D\beta}$, and 5-HT$_{1E}$ receptors were also determined as described supra, except that different cloned receptors were employed in place of the 5-HT$_{1F}$ receptor clone employed therein. The same panel was then tested in the cAMP assay to determine their agonist or antagonist character. Finally, the ability of these compounds to inhibit neuronal protein extravasation, a functional assay for migraine pain, was measured.

The panel of compounds used in this study represents distinct structural classes of compounds which were shown to exhibit a wide range of affinities for the serotonin receptors assayed. Additionally, the panel compounds were shown to have a wide efficacy range in the neuronal protein extravasation assay as well. The panel of compounds selected for this study are described below.

Compound I

3-[2-(dimethylamino) ethyl]-N-methyl-1H-indole-5- methanesulfonamide butane-1, 4-dioate (1:1)

(Sumatriptan succinate)

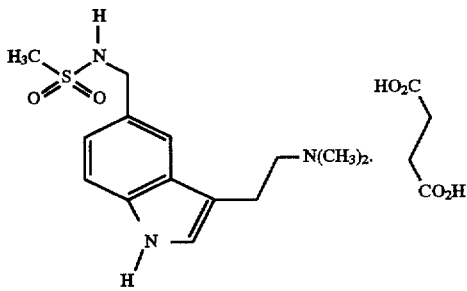

Sumatriptan succinate is commercially available as Imitrex™ or may be prepared as described in U.S. Pat. No. 5,037,845, issued Aug. 6, 1991, which is herein incorporated by reference.

Compound II 5-fluoro-3-<1-<2-<1-methyl-1H-pyrazol-4-yl>ethyl>-4- piperidinyl>1H-indole hydrochloride

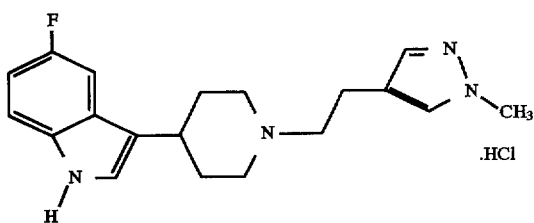

Compound II is available by the following procedure.

2-(1-methyl-3-pyrazolo)-1-ethanol

To a mixture of 200 gm (2.85 mole) 2,3-dihydrofuran and 800 mL (4.81 mole) triethylorthoformate were added 0.8 mL (6.5 mMol) boron trifluoride diethyl etherate dropwise. After an initial exotherm the reaction mixture was allowed to stir at ambient temperature for four days. To the reaction mixture was then added 4.0 gm potassium carbonate and the reaction mixture was distilled under 6.0 mm Hg. Fractions distilling between 60° C. and 130° C. were collected to give 261.64 gm (42.1%) of a light yellow oil.

MS(m/e): 219(M$^+$)

To a solution of 87.2 gm (0.40 mole) of the previously prepared yellow oil in 787 mL 1N HCl were added 21.3 mL (0.40 mole) methyl hydrazine and the reaction mixture was stirred at reflux for four hours. The reaction mixture was cooled to ambient temperature and the volatiles were removed under reduced pressure. The residual oil was treated with 2N NaOH until basic and the aqueous extracted well with dichloromethane. The combined organic extracts were dried over sodium sulfate and concentrated under reduced pressure to give 32.15 gm (64.5%) of the title compound as a brown oil.

MS(m/e): 126(M$^+$)

$^1$H-NMR(DMSO-d$_6$): δ7.45 (s, 1H); 7.25 (s, 1H); 4.65 (t, 1H); 3.75 (s,3H); 3.55 (m, 2H); 2.55 (t, 2H).

1-meth-4-(2-methanesulfulfonyloxyethyl)pyrazole

To a solution of 16.0 gm (127 mMol) 2-(1-methyl-3-pyrazolo)-1-ethanol and 27 mL (193 mMol) triethylamine in 550 mL tetrahydrofuran were added 10.8 mL (140 mMol) methanesulfonyl chloride with icebath cooling. Once the addition was complete, the reaction mixture was stirred at ambient for 4 hours. The volatiles were then removed under reduced pressure and the residue partitioned between water and dichloromethane. The organic phase was washed with water followed by saturated aqueous sodium chloride and the remaining organics dried over sodium sulfate. The solvent was removed under reduced pressure to give a crude yield of 28.4 gm of the title compound as a brown oil. The product was used without further purification.

5-fluoro-3-[1,2,3,6-tetrahydro-4-pyridyl]-1H-indole

To a solution of 74 gm potassium hydroxide in 673 mL methanol were added 10.0 gm (74 mMol) 5-fluoroindole and 23.3 gm (151 mMol) 4-piperidone.HCl.H$_2$O. The reaction mixture was stirred at reflux for 18 hours. The reaction mixture was diluted with 1.3 L of water and the resulting precipitate recovered by filtration and dried under reduced pressure to give 10.75 gm (67.2%) of 5-fluoro-3-[1,2,5,6-tetrahydro-4-pyridyl]-1H-indole as a yellow solid.

5-fluoro-3-(4-piperidinyl)-1H-indole

To a solution of 10.75 gm (50 mMol) 5-fluoro-3-[1,2,5,6-tetrahydro-4-pyridyl]-1H-indole in 500 mL ethanol were added 2.0 gm 5% palladium on carbon and the reaction mixture hydrogenated at ambient temperature for 18 hours at an initial hydrogen pressure of 60 p.s.i. The reaction mixture was then filtered through a pad of celite and the filtrate concentrated under reduced pressure to give an off-white solid. The solid was recrystallized from methanol to give 8.31 gm (76.2%) of the title compound as a colorless solid.

m.p.=229°–230° C.

MS(m/e): 218(M$^+$)

Calculated for C$_{13}$H$_{15}$N$_2$F: Theory: C, 71.53; H, 6.93; N, 12.83. Found: C, 71.81; H, 7.02; N, 12.80.

Alkylation

To a solution of 2.0 gm (9.2 mMol) 5-fluoro-3-(4-piperidinyl)-1H-indole and 2.4 gm (23 mMol) sodium carbonate in 50 mL dimethylformamide were added 1.87 gm (9.2 mMol) 1-methyl-4-(2-methanesulfonyloxyethyl) pyrazole in 5 mL dimethylformamide. The reaction mixture was stirred at 100° C. for 18 hours. The reaction mixture was cooled to ambient and the solvent removed under reduced pressure. The residue was partitioned between dichloromethane and water and the phases separated. The organic phase was washed well with water followed by saturated aqueous sodium chloride. The remaining organic phase was dried over sodium sulfate and concentrated under reduced pressure. The residual oil was subjected to silica gel chromatography, eluting with 20:1 dichloromethane:methanol. Fractions shown to contain the desired compound were combined and concentrated under reduced pressure to give a yellow oil. The oil was converted to the hydrochloride salt and was crystallized from ethyl acetate/methanol. 1.61 gm (51.1%) of Compound II were recovered as colorless crystals.

m.p.=239° C.

MS(m/e): 326(M$^+$)

Calculated for C$_{19}$H$_{23}$N$_4$F.HCl: Theory: C, 62.89; H, 6.67; N, 15.44. Found: C, 62.80; H, 6.85; N, 15.40.

Compound III 5-hydroxy-3-(4-piperidinyl)-1H-indole oxalate

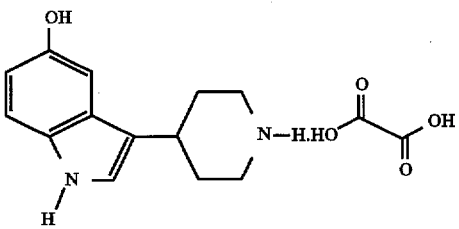

Compound III is available by the following procedure.

5-benzyloxy-3-[1,2,5,6-tetrahydro-4-pyridinyl]-1H-indole

Starting with 5.0 gm (22 mMol) 5-benzyloxyindole and 6.88 gm (45 mMol) 4-piperidone.HCl.H$_2$O, 6.53 gm (97.6%) of 5-benzyloxy-3-[1,2,5,6-tetrahydro-4-pyridinyl]-1H-indole were recovered as a light yellow solid by the procedure described in Preparation I. The material was used in the subsequent step without further purification.

Hydrogenation/Hydrogenolysis

To a solution of 1.23 gm (4 mMol) 5-benzyloxy-3-[1,2,5,6-tetrahydro-4-pyridinyl]-1H-indole in 50 mL 1:1 tetrahydrofuran:ethanol were added 0.3 gm 5% palladium on carbon and the reaction mixture hydrogenated at ambient temperature for 18 hours with an initial hydrogen pressure of 60 p.s.i. The reaction mixture was then filtered through a celite pad and the filtrate concentrated under reduced pressure. The residue was converted to the oxalate salt and 0.98 gm (80.0%) of Compound III were recovered as a brown foam.

m.p.=67° C.

MS(m/e): 216(M$^+$)

Calculated for C$_{13}$H$_{16}$N$_2$O.C$_2$H$_2$O$_4$: Theory: C, 58.81; H, 5.92; N, 9.14. Found: C, 58.70; H, 5.95; N, 9.39.

Compound IV

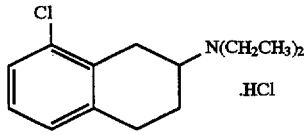

Compound IV is available by the following procedure.

8-chloro-2-tetralone

A mixture of 30.0 gm (0.176 mole) of o-chlorophenylacetic acid and 40.0 mL of thionyl chloride was stirred at ambient temperature for 18 hours. The volatiles were then removed in vacuo to give 32.76 gm (99.0 %) of o-chlorophenylacetyl chloride as a transparent, pale yellow, mobile liquid.

NMR(CDCl$_3$): 7.5–7.1 (m, 4H), 4.2 (s, 2H).

To a slurry of 46.5 gm (0.348 mole) AlCl$_3$ in 400 mL dichloromethane at −78° C. was added a solution of 32.76 gm (0.174 mole) of the previously prepared o-chlorophenylacetyl chloride in 100 mL dichloromethane dropwise over 1 hour. The dry ice/acetone bath then was replaced with an ice/water bath and ethylene was bubbled into the reaction mixture during which time the temperature rose to 15° C. The ethylene addition was discontinued at the end of the exotherm and the reaction mixture was stirred at about 5° C. for 4 hours. Ice was then added to the reaction mixture to destroy aluminum complexes. Upon termination of the exotherm, the reaction mixture was diluted with 500 mL of water and stirred vigorously until all solids had dissolved. The phases were separated and the organic phase was washed with 3×400 mL 1N hydrochloric acid and 2×400 mL saturated aqueous sodium bicarbonate. The remaining organic phase was then dried over sodium sulfate and concentrated in vacuo to give a pale orange residue. The residue was dissolved in 1:1 hexane:diethyl ether and was poured over a flash silica column which was then eluted with 1:1 hexane:diethyl ether to give a light yellow residue which was crystallized from 4:1 hexane:diethyl ether to give 10.55 gm of the title compound.

NMR(CDCl$_3$): 7.5–7.2 (m, 3H), 3.7 (s, 2H), 3.3–3.0 (t, J=7 Hz, 2H), 2.8–2.4 (t, J=7 Hz, 2H).

MS: 180(60), 165(9), 138(100), 117(52), 115(50), 103(48), 89(20), 76(25), 74(18), 63(30), 57(9), 52(28), 51(20), 42(6), 39(32).

IR(nujol mull): 2950 cm$^{-1}$, 2927 cm$^{-1}$, 1708 cm$^{-1}$, 1464 cm$^{-1}$, 1450 cm$^{-1}$, 1169 cm$^{-1}$, 1141 cm$^{-1}$.

Reductive Amination

To a solution of 0.5 gm (2.78 mMol) 8-chloro-2-tetralone in 25 mL cyclohexane were added 1.4 mL (13.9 mMol) diethylamine followed by 0.1 gm p-toluenesulfonic acid monohydrate. The reaction mixture was then heated at reflux with constant water removal (Dean-Stark Trap) for 18 hours. The reaction mixture was then cooled to ambient and the volatiles removed under reduced pressure. The residue was then dissolved in 15 mL methanol to which were then added 1.5 mL acetic acid followed by the portionwise addition of 0.5 gm sodium borohydride. The reaction mixture was then stirred for 1 hour at ambient.

The reaction mixture was then diluted with 20 mL 10% HCl and stirred for an additional hour. The mixture was then extracted with diethyl ether and the remaining aqueous phase was poured over ice, made basic with ammonium hydroxide and extracted well with dichloromethane. These extracts were combined, dried over sodium sulfate and concentrated under reduced pressure. The residue was redissolved in dichloromethane and subjected to chromatography over basic alumina, eluting with dichloromethane. Fractions shown to contain product were combined and concentrated under reduced pressure. The residual oil was dissolved in diethyl ether and the solution saturated with hydrogen chloride. The viscous residue was crystallized from acetone/diethyl ether to give 0.20 gm (23.2%) of Compound IV as colorless crystals.

m.p.=158°–159° C.

MS(m/e): 273

Calculated for C$_{14}$H$_{21}$NCl.HCl: Theory: C, 61.32; H, 7.72; N, 5.11. Found: C, 61.62; H, 7.94; N, 5.03.

Compound V 6-hydroxy-3-dimethylamino-1,2,3,4-tetrahydrocarbazole

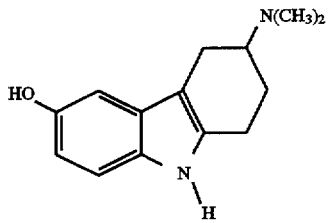

Compound V is available by the following procedure.

4-dimethylamino-1-cyclohexanone ethylene ketal

To a solution of 5.0 gm (32 mMol) 1,4-cyclohexanedione mono-ethylene ketal and 10.80 gm (240 mMol) dimethylamine were added 2.0 mL acetic acid and the mixture was stirred at 0° C. for 1.5 hours. To this solution were then added 3.62 gm (58 mMol) sodium cyanoborohydride and the reaction stirred for an additional hour at ambient. The pH of the reaction mixture was adjusted to ~7 with 16 mL acetic acid and stirred 18 hours at ambient. The volatiles were removed under reduced pressure and the residue dissolved in cold 5% tartaric acid solution and then the aqueous phase was made basic with 5N sodium hydroxide. This aqueous phase was extracted well with dichloromethane. These organic extracts were combined and concentrated under reduced pressure to give 5.04 gm (85% of the title compound as an oil.

4-dimethylamino-1-cyclohexanone 4.96 gm (26.8 mMol) 4-dimethylamino-1-cyclohexanone ethylene ketal were dissolved in 50 mL formic acid and the solution stirred at reflux for 18 hours. The reaction mixture was then cooled to ambient and the volatiles removed under reduced pressure to give 3.78 gm (100%) of the title compound.

6-benzyloxy-3-dimethylamino-1,2,3,4-tetrahydrocarbazole

To a solution of 3.78 gm (26.8 mMol) 4-dimethylamino-1-cyclohexanone and 6.69 gm (26.8 mMol) 4-benzyloxyphenylhydrazine hydrochloride in 50 mL ethanol were added 2.17 mL (26.8 mMol)pyridine. To this solution were added 5×10 mL portions of water and the reaction mixture then stored at 0° C. for 18 hours. The reaction mixture was then diluted with an additional 50 mL of water and the mixture extracted well with dichloromethane. The combined organic extracts were dried over sodium sulfate and the volatiles removed under reduced pressure. The residual oil was subjected to flash silica gel chromatography, eluting with 9:1 chloroform:methanol. Fractions shown to contain the desired product were combined and concentrated under reduced pressure to give 2.14 gm (24.9%) of the title compound.

Hydrogenolysis

To a solution of 2.14 gm (6.7 mMol) 6-benzyloxy-3-dimethylamino-1,2,3,4-tetrahydrocarbazole in 50 mL ethanol were added 0.20 gm 10% palladium on carbon and the reaction mixture was hydrogenated at ambient temperature with an initial hydrogen pressure of 40 p.s.i. After 5 hours an additional charge of 0.20 gm 10% palladium on carbon were added and the reaction mixture repressurized with hydrogen to 40 p.s.i. for 4 hours. The reaction mixture was then filtered through a pad of celite and the filtrate concentrated under reduced pressure. The residue was subjected to Florisil chromatography, eluting with 9:1 chloroform:methanol. Fractions shown to contain the desired compound were combined and concentrated under reduced pressure. The residue was again subjected to Florisil chromatography, eluting with a gradient consisting of chloroform containing 2–10% methanol. Fractions shown to contain product were combined and concentrated under reduced pressure to give Compound V as a crystalline solid.

MS(m/e): 230($M^+$)

Calculated for $C_{14}H_{18}N_2O$: Theory: C, 73.01; H, 7.88; N, 12.16. Found: C, 72.75; H, 7.83; N, 11.97.

Binding Assays

The binding affinities of compounds for various serotonin receptors were determined essentially as described above except that different cloned receptors are employed in place of the 5-$HT_{1F}$ receptor clone employed therein. The results of these binding experiments are summarized in Table I.

TABLE I

BINDING TO SEROTONIN (5-$HT_1$) RECEPTOR SUBTYPES ($K_i$ nM)

| Compound | 5-$HT_{1D\alpha}$ | 5-$HT_{1D\beta}$ | 5-$HT_{1E}$ | 5-$HT_{1F}$ |
|---|---|---|---|---|
| I | 4.8 | 9.6 | 2520.0 | 25.7 |
| II | 21.7 | 53.6 | 50.3 | 2.5 |
| III | 163.2 | 196.5 | 3.9 | 22.0 |
| IV | 13.5 | 145.3 | 813.0 | 129.2 |
| V | 791.0 | 1683.0 | 73.6 | 10.3 | cAMP Formation

All of the compounds of the panel were tested in the cAMP formation assay described supra and all were found to be agonists of the 5-$HT_{1F}$ receptor.

Protein Extravasation

Harlan Sprague-Dawley rats (225–325 g) or guinea pigs from Charles River Laboratories (225–325 g) were anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes were drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes (Rhodes Medical Systems, Inc.) were lowered through the holes in both hemispheres to a depth of 9 mm (rats) or 10.5 mm (guinea pigs) from dura.

The femoral vein was exposed and a dose of the test compound was injected intravenously (1 mL/kg). Approximately 7 minutes later, a 50 mg/kg dose of Evans Blue, a fluorescent dye, was also injected intravenously. The Evans Blue complexed with proteins in the blood and functioned as a marker for protein extravasation. Exactly 10 minutes post-injection of the test compound, the left trigeminal ganglion was stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals were killed and exsanguinated with 20 mL of saline. The top of the skull was removed to facilitate the collection of the dural membranes. The membrane samples were removed from both hemispheres, rinsed with water, and spread flat on microscopic slides. Once dried, the tissues were cover-slipped with a 70% glycerol/water solution.

A fluorescence microscope (Zeiss) equipped with a grating monochromator and a spectrophotometer was used to quantify the amount of Evans Blue dye in each sample. An excitation wavelength of approximately 535 nm was utilized and the emission intensity at 600 nm was determined. The microscope was equipped with a motorized stage and also interfaced with a personal computer. This facilitated the computer-controlled movement of the stage with fluorescence measurements at 25 points (500 µm steps) on each dural sample. The mean and standard deviation of the measurements was determined by the computer.

The extravasation induced by the electrical stimulation of the trigeminal ganglion was an ipsilateral effect (i.e. occurs only on the side of the dura in which the trigeminal ganglion was stimulated). This allows the other (unstimulated) half of the dura to be used as a control. The ratio of the amount of extravasation in the dura from the stimulated side compared to the unstimulated side dura was calculated. Saline controls yielded a ratio of approximately 2.0 in rats and 1.8 in guinea pigs. In contrast, a compound which effectively prevented the extravasation in the dura from the stimulated side would have a ratio of approximately 1.0. A dose-response curve was generated and the dose that inhibited the extravasation by 50% (ID50) was approximated. This data is presented in Table II.

TABLE II

Inhibition of Protein Extravasation ($ID_{50}$ mMol/kg)

| Compound | i.v. $ID_{50}$ (mMol/kg) |
| --- | --- |
| I | $2.6 \times 10^{-8}$ |
| II | $8.6 \times 10^{-10}$ |
| III | $8.9 \times 10^{-9}$ |
| IV | $1.2 \times 10^{-7}$ |
| V | $8.7 \times 10^{-9}$ |

To determine the relationship of binding at various serotonin receptors to inhibition of neuronal protein extravasation, the binding affinity of all of the compounds to each of the $5\text{-HT}_{1D\alpha}$, $5\text{-HT}_{1D\beta}$, $5\text{-HT}_{1E}$ and $5\text{-HT}_{1F}$ receptors was plotted against their $ID_{50}$ in the protein extravasation model. A linear regression analysis was performed on each set of data and a correlation factor, $R^2$, calculated. The results of this analysis are summarized in Table III.

TABLE III

Correlation Factor ($R^2$) for Specific $5\text{-HT}_1$ Subtype Binding Affinity vs Inhibition of Protein Extravasation

| $5\text{-HT}_1$ Subtype | Correlation Factor ($R^2$) |
| --- | --- |
| $5\text{-HT}_{1D\alpha}$ | 0.07 |
| $5\text{-HT}_{1D\beta}$ | 0.001 |
| $5\text{-HT}_{1E}$ | 0.31 |
| $5\text{-HT}_{1F}$ | 0.94 |

An ideally linear relationship would generate a correlation factor of 1.0, indicating a cause and effect relationship between the two variables. The experimentally determined correlation factor between inhibition of neuronal protein extravasation and $5\text{-HT}_{1F}$ binding affinity is 0.94. This nearly ideal dependence of the $ID_{50}$ in the protein extravasation model on binding affinity to the $5\text{-HT}_{1F}$ receptor clearly demonstrates that the $5\text{-HT}_{1F}$ receptor mediates the inhibition of protein extravasation resulting from stimulation of the trigeminal ganglia.

Sumatriptan exhibits low bioavailability and relatively short duration of action. Its affinity for a number of serotonin receptor subtypes gives rise to undesirable side effects, particularly vasoconstriction, which severely limits its utility in the treatment of migraine. The compounds of this invention, however, are highly bioavailable through several routes of administration including, but not limited to, oral, buccal, intravenous, subcutaneous, intranasal, intraocular, transdermal, rectal and by inhalation. They exhibit a rapid onset and long duration of action, typically requiring only a single dose per day to maintain therapeutic levels. Since compounds of this invention are potent agonists of the $5\text{-HT}_{1F}$ receptor, extremely low doses are required to maintain therapeutic levels. Additionally, due to the high selectivity of compounds of this invention for the $5\text{-HT}_{1F}$ receptor, complications due to vasoconstriction are avoided. Compounds of this invention also inhibit protein extravasation if administered prior or subsequent to stimulation of the trigeminal ganglia, suggesting they may be administered prior to an incipient migraine attack to prevent pain, or during a migraine attack to alleviate pain.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, buccal, rectal, intranasal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.001 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.0001 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
| --- | --- |
| Compound of Example 30 | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Compound of Example 129 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Compound of Example 142 | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Compound of Example 41 | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
| --- | --- |
| Compound of Example 51 | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
| --- | --- |
| Compound of Example 98 | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
| --- | --- |
| Compound of Example 99 | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
| --- | --- |
| Compound of Example 105 | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
| --- | --- |
| Compound of Example 106 | 250.0 mg |
| Isotonic saline | 1000 ml |

Formulation Example 10

A topical formulation may be prepared as follows:

| Ingredient | Quantity |
| --- | --- |
| Compound of Example 118 | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
| --- | --- |
| Compound of Example 88 | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:
1. A compound of Formula I:

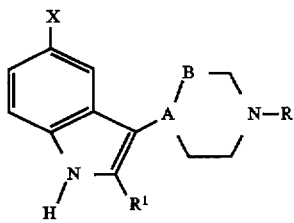

in which

A—B is —CH—CH$_2$— or —C=CH—;

R is H or C$_1$-C$_6$ alkyl;

R$^1$ is H or C$_1$-C$_4$ alkyl;

X is —C(O)NR$^4$R$^{15}$, —NR$^5$R$^6$, —NR$^7$SO$_2$R$^8$, —NHC(Q)NR$^{10}$R$^{11}$, —NHC(O)OR$^{12}$ or —NR$^{13}$C(O)R$^{14}$;

where

Q is O, or S;

R$^4$ is heteroaryl, substituted heteroaryl, heteroaryl(C$_1$-C$_4$ alkyl), or substituted heteroaryl(C$_1$-C$_4$ alkyl);

R$^4$ and R$^{15}$ taken together with the nitrogen atom form a pyrrolidine, piperidine, substituted piperidine, piperazine, 4-substituted piperazine, morpholine or thiomorpholine ring;

R$^5$ and R$^6$ are both trifluoromethanesulfonyl;

R$^7$ is H or C$_1$-C$_4$ alkyl;

R$^8$ is phenyl, substituted phenyl, or di(C$_1$-C$_4$ alkyl) amino;

R$^{10}$ and R$^{11}$ are independently selected from the group consisting of C$_1$-C$_6$ alkyl, C$_3$-C$_6$ alkenyl, C$_3$-C$_8$ cycloalkyl, phenyl, substituted phenyl, phenyl(C$_1$-C$_4$ alkylene), phenyl(C$_1$-C$_4$ alkylene) substituted in the phenyl ring, ((C$_1$-C$_4$ alkyl or C$_1$-C$_4$ alkoxycarbonyl substituted)C$_1$-C$_4$ alkyl)phenyl, C$_1$-C$_4$ alkyl α-substituted with C$_1$-C$_4$ alkoxycarbonyl; or R$^{10}$ and R$^{11}$ taken together with the nitrogen atom form a pyrrolidine, piperidine, piperazine, 4-substituted piperazine, morpholine or thiomorpholine ring;

R$^{12}$ is C$_1$-C$_6$ alkyl, C$_3$-C$_6$ alkenyl, phenyl, substituted phenyl, C$_3$-C$_8$ cycloalkyl, C$_1$-C$_4$ alkyl ω-substituted with C$_1$-C$_4$ alkoxy;

R$^{13}$ is H or C$_1$-C$_4$ alkyl;

R$^{14}$ is C$_1$-C$_{10}$ alkyl substituted with from one to three substituents selected from the group consisting of hydroxy, C$_1$-C$_4$ alkoxy, halo, aryloxy, C$_1$-C$_4$ alkoxycarbonyl and heteroaryloxy, C$_2$-C$_{10}$ alkenyl, C$_2$-C$_{10}$ alkynyl, C$_3$-C$_8$ cycloalkyl, phenyl, substituted phenyl, naphthyl, phenyl(C$_1$-C$_4$ alkylene), phenyl(C$_1$-C$_4$ alkylene) substituted on the phenyl ring, 2-phenylethylen-1yl, diphenylmethyl, benzofused C$_4$-C$_8$ cycloalkyl, C$_1$-C$_4$ alkylene w-substituted with C$_3$-C$_6$ cycloalkyl, or a heterocycle;

R$^{15}$ is H or C$_1$-C$_6$ alkyl;

and pharmaceutically acceptable acid addition salts and solvates thereof.

2. A compound of claim 1, in which A—B is —C=CH—.

3. A compound of claim 1, in which A—B is —CH—CH$_2$—.

4. A compound of claim 1, in which R$^1$ is H.

5. A pharmaceutical formulation which comprises, in association with a pharmaceutically acceptable carrier, diluent or excipient, a compound of claim 1.

6. A pharmaceutical formulation of claim 5, in which A—B is —C=CH—.

7. A pharmaceutical formulation of claim 5, in which A—B is —CH—CH$_2$—.

8. A pharmaceutical formulation of claim 5, in which R is H.

9. A method for the activation of 5-HT$_{1F}$ receptors in mammals, comprising administering to a mammal in need of such activation an effective amount of a compound of claim 1.

10. A method of claim 9 where the mammal is a human.

11. A method for the inhibition of neuronal protein extravasation, comprising administering to a mammal in need thereof an effective amount of a compound of claim 1.

12. A method of claim 11 where the mammal is a human.

13. A compound of claim 1, in which X is —NR$^{13}$C(O)R$^{14}$.

14. A compound of claim 13 which is 5-(4-fluorobenzoyl)amino-3-(1-methylpiperidin-4-yl)-1H-indole and pharmaceutically acceptable acid addition salts and solvates thereof.

15. A compound of claim 14 which is 5-(4-fluorobenzoyl)amino-3-(1-methylpiperidin-4-yl)-1H-indole hydrochloride.

16. A pharmaceutical formulation of claim 5, in which X is —NR$^{13}$C(O)R$^{14}$.

17. A pharmaceutical formulation of claim 16, in which the compound is 5-(4-fluorobenzoyl)amino-3-(1-methylpiperidin-4-yl)-1H-indole and pharmaceutically acceptable acid addition salts and solvates thereof.

18. A pharmaceutical formulation of claim 16, in which the compound is 5-(4-fluorobenzoyl)amino-3-(1-methylpiperidin-4-yl)-1H-indole hydrochloride.

19. A method for the treatment of migraine, comprising administering to a mammal in need of such treatment an effective amount of a compound of claim 1.

20. A method of claim 19 where the mammal is human.

21. A method of claim 19, in which X is —NR$^{13}$C(O)R$^{14}$.

22. A method of claim 21 where the compound is 5-(4-fluorobenzoyl)amino-3-(1-methylpiperidin-4-yl)-1H-indole and pharmaceutically acceptable acid addition salts and solvates thereof.

23. A method of claim 21 where the compound is 5-(4-fluorobenzoyl)amino-3-(1-methylpiperidin-4-yl)-1H-indole hydrochloride.

24. A method for the prevention of migraine, comprising administering prophylactically to a mammal subject to a migraine, an effective amount of a compound of claim 1.

25. A method of claim 24 where the mammal is human.

26. A method of claim 24, in which X is —NR$^{13}$C(O)R$^{14}$.

27. A method of claim 26 where the compound is 5-(4-fluorobenzoyl)amino-3-(1-methylpiperidin-4-yl)-1H-indole and pharmaceutically acceptable acid addition salts and solvates thereof.

28. A method of claim 26 where the compound is 5-(4-fluorobenzoyl)amino-3-(1-methylpiperidin-4-yl)-1H-indole hydrochloride.

* * * * *